(12) United States Patent
Lovejoy et al.

(10) Patent No.: US 9,718,857 B2
(45) Date of Patent: *Aug. 1, 2017

(54) METHOD FOR REGULATING NEURITE GROWTH

(76) Inventors: David Lovejoy, Stouffville (CA); Arij Al Chawaf, North York (CA)

( * ) Notice: Subject to any disclaimer, the term of this patent is extended or adjusted under 35 U.S.C. 154(b) by 339 days.

This patent is subject to a terminal disclaimer.

(21) Appl. No.: 13/527,414

(22) Filed: Jun. 19, 2012

(65) Prior Publication Data

US 2014/0011744 A1    Jan. 9, 2014

Related U.S. Application Data

(63) Continuation of application No. 11/706,375, filed on Feb. 15, 2007, now abandoned, which is a continuation-in-part of application No. 10/510,959, filed as application No. PCT/CA03/00622 on May 2, 2003, now Pat. No. 8,088,889.

(60) Provisional application No. 60/376,879, filed on May 2, 2002, provisional application No. 60/377,231, filed on May 3, 2002, provisional application No. 60/424,016, filed on Nov. 6, 2002, provisional application No. 60/773,309, filed on Feb. 15, 2006, provisional application No. 60/783,821, filed on Mar. 21, 2006.

(51) Int. Cl.
  *C07K 14/70* (2006.01)
  *C07K 2/00* (2006.01)
  *C07K 14/705* (2006.01)

(52) U.S. Cl.
  CPC .............. *C07K 2/00* (2013.01); *C07K 14/705* (2013.01)

(58) Field of Classification Search
  None
  See application file for complete search history.

(56) References Cited

PUBLICATIONS

Ng and Henikoff, Annu Rev Genomics Hum Genet, 7:61-80, 2006.*
Wang et al., Brain Res Mol Brain Res, 133(2):253-265, Feb. 2005.*
Minet et al., J Cell Science, 112: 2019-2032, 1999.*

* cited by examiner

*Primary Examiner* — Kimberly A. Ballard
*Assistant Examiner* — Stacey MacFarlane
(74) *Attorney, Agent, or Firm* — Gowling WLG (Canada) LLP; Anita Nador

(57) ABSTRACT

This invention relates to a method of inhibiting neuronal cell death, including protecting neuronal cells from cell death and the effects of stress, such as high or low pH, comprising administering to the cells an effective amount of Teneurin C-terminal Associated Peptide (TCAP). The invention provides the use of TCAP to prevent and/or treat a number of brain conditions, such as hypoxia-ischemia and brain alkalosis or various brain or spinal cord injuries due to physical or physiological stresses. In one aspect the invention provides a use of TCAP to increase β-tubulin, β-actin levels in neuronal cells and/or to increase fasciculation among neuronal cells, in culture or in tissue. In another aspect, the invention provides a method of treating various pH induced neuronal conditions.

13 Claims, 19 Drawing Sheets

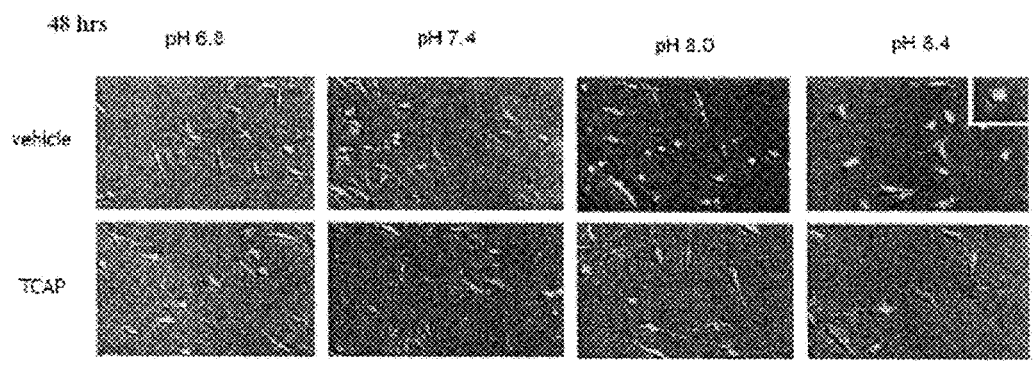
FIGURE 1A
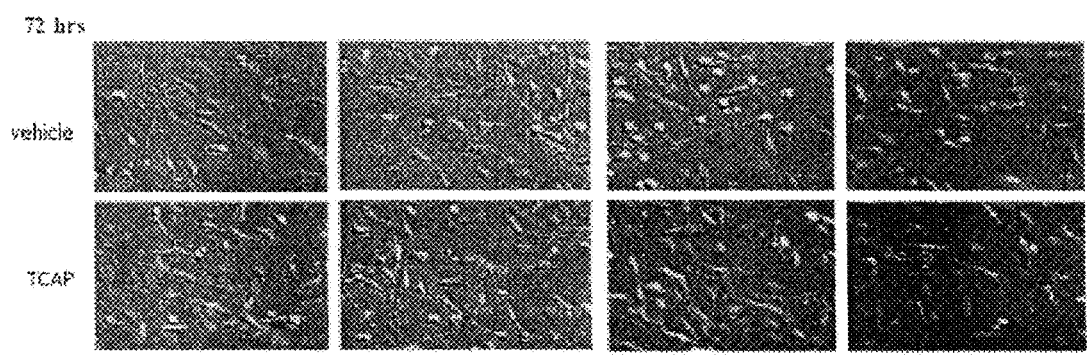
FIGURE 1B
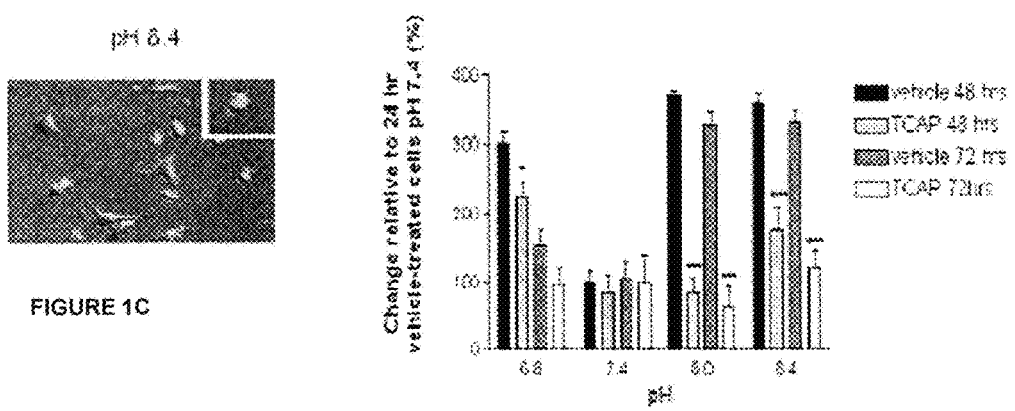
FIGURE 1C
FIGURE 1D

FIGURE 2A
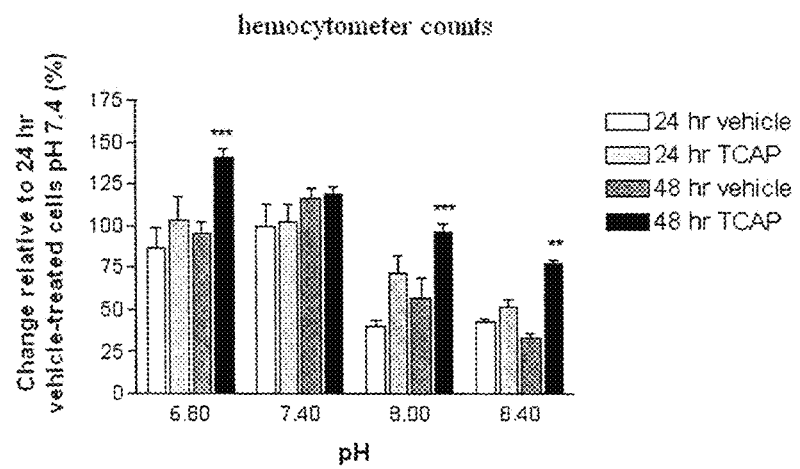
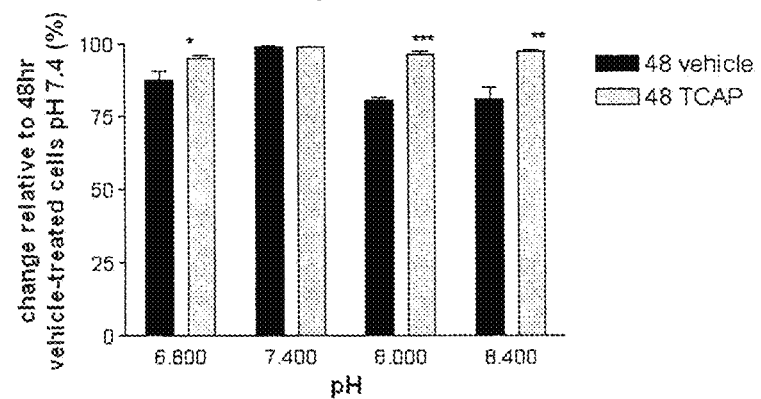
FIGURE 2B

A

B

C

SEQUENCE LISTING

<160> NUMBER OF SEQ ID NOS: 136

<210> SEQ ID NO 1
<211> LENGTH: 1490
<212> TYPE: DNA
<213> ORGANISM: Artificial Sequence
<220> FEATURE:
<223> OTHER INFORMATION: Rainbow Trout Ten M3 carboxy termini'

<400> SEQUENCE: 1

| | | | | | | |
|---|---|---|---|---|---|---|
| tccatctcgg | gggtgcaaca | ggaagtgacc | cggcaagcca | aggctttcct | gtccttcgag | 60 |
| aggatgccgg | agatccagct | gagccgccgg | cgctccaacc | gggagaaacc | ctggctgtgg | 120 |
| ttcgccaccg | ccaagtctct | gatcggtaag | ggtgtcatgt | tggcggtgac | gcagggccgt | 180 |
| gtggtcacca | acgctctgaa | catcgccaac | gaggactgca | tcaaggtcgc | cgccgtcctc | 240 |
| aacaatgcgt | tctacctgga | ggacctgcac | ttcacggtgg | agggacgcga | cacgcactac | 300 |
| ttcatcaaga | ccagcctccc | ggagagcgac | ctgggagcgc | tgaggctgac | aagcgggagg | 360 |
| aagtcgctga | agaacggaag | tcaacgtgac | tgtgtcccag | tccaccaccg | tggtgaacgg | 420 |
| cagaaccggc | gcttcgccga | cgtggagctg | cagtacggcg | ctctagcgct | ccacgtgcgc | 480 |
| tatggcatga | ctctggacga | ggagaaggcg | cgtgtgctgg | agcaggccag | gcagaaggcg | 540 |
| ttgtcgagtg | cctggtccag | ggagcaacaa | cgggtgaggg | aggggagga | ggggtgagg | 600 |
| ctgtggacgg | aggggagaa | gaggcagctg | ctgagcggga | ggaaggttct | gggctacgac | 660 |
| gggtactacg | tcctctccat | agagcagtac | cccgagctag | cagactccgc | taacaacatc | 720 |
| cagttcctca | ggcagagcga | aatagggaag | aggtaacaga | cagaatcctc | ggcactggcc | 780 |
| gccaaagaga | ctacccctc | caaatcctgc | ccccaacct | ccctcgcctc | cccctttc | 840 |
| tctaaaaagg | gggagggtcc | aggctagtgc | tgtgtttagc | gccgactagc | tgaaacaaac | 900 |
| agtaaaatgt | agaatatctt | aaactgaact | atacctaata | ctaccactgt | ggggcctgaa | 960 |
| aatcaaacaa | aacggctcca | actgacgcaa | atgtttgtcc | catgtgctat | acagcgttga | 1020 |
| atggactgtg | gactctcttg | aaaagagaga | aaaaaagtc | aaaactctcg | gtttgtgaaa | 1080 |
| ggagaaaaaa | acgttttttt | tttttttaaa | tagacttcct | gaatttgctt | tcggaaaaaa | 1140 |
| tattttaaaa | agaaagaaga | aatgtgttta | catacgcata | acactacaac | acgtctggac | 1200 |
| taatagaaga | aaagccttct | ggtttcttac | acaggacaac | gtctataatc | tgattctaca | 1260 |
| tcctgacgac | tgacctttga | ttgacctttg | cgtactgaaa | aaggtagtgt | tgttgttcgc | 1320 |
| agtaggacca | tgggtctcca | atggtggtaa | ctagacagtt | aaaaccactt | gttgaaacca | 1380 |
| cttgcttgtt | cttctgcttt | tctttccaaa | agggacaaaa | cagctcccac | caagtgactt | 1440 |
| ctttaccaat | actagatcaa | agtgggacgt | tttgggctcg | tgccgaattc | | 1490 |

<210> SEQ ID NO 2
<211> LENGTH: 756
<212> TYPE: DNA

<213> ORGANISM: Artificial Sequence
<220> FEATURE:
<223> OTHER INFORMATION: Rainbow Trout Ten M3 coding sequence of carboxy termini of Ten M3

<400> SEQUENCE: 2

```
tccatctcgg gggtgcaaca ggaagtgacc cggcaagcca aggctttcct gtccttcgag      60
aggatgccgg agatccagct gagccgccgg cgctccaacc gggagaaacc ctggctgtgg     120
ttcgccaccg ccaagtctct gatcggtaag ggtgtcatgt tggcggtgac gcagggccgt     180
gtggtcacca acgctctgaa catcgccaac gaggactgca tcaaggtcgc cgccgtcctc     240
aacaatgcgt tctacctgga ggacctgcac ttcacggtgg agggacgcga cacgcactac     300
ttcatcaaga ccagcctccc ggagagcgac ctgggagcgc tgaggctgac aagcgggagg     360
aagtcgctgg agaacggaag tcaacgtgac tgtgtcccag tccaccaccg tggtgaacgg     420
cagaaccggc gcttcgccga cgtggagctg cagtacggcg ctctagcgct ccacgtgcgc     480
tatggcatga ctctggacga ggagaaggcg cgtgtgctgg agcaggccag gcagaaggcg     540
ttgtcgagtg cctggtccag ggagcaacaa cgggtgaggg aggggaggga gggggtgagg     600
ctgtggacgg aggggagaa gaggcagctg ctgagcggga ggaaggttct gggctacgac     660
gggtactacg tcctctccat agagcagtac cccgagctag cagactccgc taacaacatc     720
cagttcctca ggcagagcga aatagggaag aggtaa                               756
```

<210> SEQ ID NO 3
<211> LENGTH: 251
<212> TYPE: PRT
<213> ORGANISM: Artificial Sequence
<220> FEATURE:
<223> OTHER INFORMATION: Rainbow Trout Ten M3 carboxy termini of Ten M3

<400> SEQUENCE: 3

```
Ser Ile Ser Gly Val Gln Gln Glu Val Thr Arg Gln Ala Lys Ala Phe
1               5                   10                  15

Leu Ser Phe Glu Arg Met Pro Glu Ile Gln Leu Ser Arg Arg Arg Ser
            20                  25                  30

Asn Arg Glu Lys Pro Trp Leu Trp Phe Ala Thr Ala Lys Ser Leu Ile
        35                  40                  45

Gly Lys Gly Val Met Leu Ala Val Thr Gln Gly Arg Val Val Thr Asn
    50                  55                  60

Ala Leu Asn Ile Ala Asn Glu Asp Cys Ile Lys Val Ala Ala Val Leu
65                  70                  75                  80

Asn Asn Ala Phe Tyr Leu Glu Asp Leu His Phe Thr Val Glu Gly Arg
                85                  90                  95

Asp Thr His Tyr Phe Ile Lys Thr Ser Leu Pro Glu Ser Asp Leu Gly
            100                 105                 110

Ala Leu Arg Leu Thr Ser Gly Arg Lys Ser Leu Glu Asn Gly Val Asn
        115                 120                 125

Val Thr Val Ser Gln Ser Thr Thr Val Val Asn Gly Arg Thr Arg Arg
    130                 135                 140

Phe Ala Asp Val Glu Leu Gln Tyr Gly Ala Leu Ala Leu His Val Arg
145                 150                 155                 160

Tyr Gly Met Thr Leu Asp Glu Glu Lys Ala Arg Val Leu Glu Gln Ala
                165                 170                 175

Arg Gln Lys Ala Leu Ser Ser Ala Trp Ser Arg Glu Gln Gln Arg Val
            180                 185                 190
```

```
Arg Glu Gly Glu Glu Gly Val Arg Leu Trp Thr Gly Glu Lys Arg
            195                 200                 205

Gln Leu Leu Ser Gly Arg Lys Val Leu Gly Tyr Asp Gly Tyr Tyr Val
210                 215                 220

Leu Ser Ile Glu Gln Tyr Pro Glu Leu Ala Asp Ser Ala Asn Asn Ile
225                 230                 235                 240

Gln Phe Leu Arg Gln Ser Glu Ile Gly Lys Arg
            245                 250

<210> SEQ ID NO 4
<211> LENGTH: 252
<212> TYPE: PRT
<213> ORGANISM: Artificial Sequence
<220> FEATURE:
<223> OTHER INFORMATION: Mouse Ten M1

<400> SEQUENCE: 4

Met Ile Leu Gly Ile Gln Cys Glu Leu Gln Lys Gln Leu Arg Asn Phe
1               5                   10                  15

Ile Ser Leu Asp Gln Leu Pro Met Thr Pro Gln Tyr Asn Glu Gly Arg
            20                  25                  30

Cys Leu Glu Gly Gly Lys Gln Pro Arg Phe Ala Ala Val Pro Ser Val
        35                  40                  45

Phe Gly Lys Gly Ile Lys Phe Ala Ile Lys Glu Gly Ile Val Thr Ala
    50                  55                  60

Asp Ile Ile Gly Val Ala Asn Glu Asp Ser Arg Arg Leu Ala Ala Ile
65                  70                  75                  80

Leu Asn Asn Ala His Tyr Leu Glu Asn Leu His Phe Thr Ile Glu Gly
                85                  90                  95

Arg Asp Thr His Tyr Phe Ile Lys Leu Gly Ser Leu Glu Glu Asp Leu
            100                 105                 110

Val Leu Ile Gly Asn Thr Gly Gly Arg Arg Ile Leu Glu Asn Gly Val
        115                 120                 125

Asn Val Thr Val Ser Gln Met Thr Ser Val Leu Asn Gly Arg Thr Arg
    130                 135                 140

Arg Phe Ala Asp Ile Gln Leu Gln His Gly Ala Leu Cys Phe Asn Ile
145                 150                 155                 160

Arg Tyr Gly Thr Thr Val Glu Glu Glu Lys Asn His Val Leu Glu Met
                165                 170                 175

Ala Arg Gln Arg Ala Val Ala Gln Ala Trp Thr Gln Glu Gln Arg Arg
            180                 185                 190

Leu Gln Glu Gly Glu Glu Gly Thr Arg Val Trp Thr Gly Glu Glu Lys
        195                 200                 205

Gln Gln Leu Leu Gly Thr Gly Arg Val Gln Gly Tyr Asp Gly Tyr Phe
    210                 215                 220

Val Leu Ser Val Glu Gln Tyr Leu Glu Leu Ser Asp Ser Ala Asn Asn
225                 230                 235                 240

Ile His Phe Met Arg Gln Ser Glu Ile Gly Arg Arg
                245                 250

<210> SEQ ID NO 5
<211> LENGTH: 253
<212> TYPE: PRT
<213> ORGANISM: Artificial Sequence
<220> FEATURE:
<223> OTHER INFORMATION: Mouse Ten M2

<400> SEQUENCE: 5
```

-continued

```
Leu Ile Thr Gly Val Gln Gln Thr Thr Glu Arg His Asn Gln Ala Phe
1               5                   10                  15

Leu Ala Leu Glu Gly Gln Val Ile Thr Lys Lys Leu His Ala Ser Ile
            20                  25                  30

Arg Glu Lys Ala Gly His Trp Phe Ala Thr Thr Thr Pro Ile Ile Gly
            35                  40                  45

Lys Gly Ile Met Phe Ala Ile Lys Glu Gly Arg Val Thr Thr Gly Val
        50                  55                  60

Ser Ser Ile Ala Ser Glu Asp Ser Arg Lys Val Ala Ser Val Leu Asn
65                  70                  75                  80

Asn Ala Tyr Tyr Leu Asp Lys Met His Tyr Ser Ile Glu Gly Lys Asp
                85                  90                  95

Thr His Tyr Phe Val Lys Ile Gly Ala Ala Asp Gly Asp Leu Val Thr
            100                 105                 110

Leu Gly Thr Thr Ile Gly Arg Lys Val Leu Glu Ser Gly Val Asn Val
        115                 120                 125

Thr Val Ser Gln Pro Thr Leu Leu Val Asn Gly Arg Thr Arg Arg Phe
130                 135                 140

Thr Asn Ile Glu Phe Gln Tyr Ser Thr Leu Leu Ser Ile Arg Tyr
145                 150                 155                 160

Gly Leu Thr Pro Asp Thr Leu Asp Glu Glu Lys Ala Arg Val Leu Asp
                165                 170                 175

Gln Ala Gly Gln Arg Ala Leu Gly Thr Ala Trp Ala Lys Glu Gln Gln
            180                 185                 190

Lys Ala Arg Asp Gly Arg Glu Gly Ser Arg Leu Trp Thr Glu Gly Glu
        195                 200                 205

Lys Gln Gln Leu Leu Ser Thr Gly Arg Val Gln Gly Tyr Glu Gly Tyr
    210                 215                 220

Tyr Val Leu Pro Val Glu Gln Tyr Pro Glu Leu Ala Asp Ser Ser Ser
225                 230                 235                 240

Asn Ile Gln Phe Leu Arg Gln Asn Glu Met Gly Lys Arg
                245                 250
```

<210> SEQ ID NO 6
<211> LENGTH: 251
<212> TYPE: PRT
<213> ORGANISM: Artificial Sequence
<220> FEATURE:
<223> OTHER INFORMATION: Mouse Ten M3

<400> SEQUENCE: 6

```
Pro Ile Phe Gly Val Gln Gln Gln Val Ala Arg Gln Ala Lys Ala Phe
1               5                   10                  15

Leu Ser Leu Gly Lys Met Ala Glu Gln Val Ser Arg Arg Lys Ala
            20                  25                  30

Gly Ala Glu Gln Ser Trp Leu Trp Phe Ala Thr Val Lys Ser Leu Ile
            35                  40                  45

Gly Lys Gly Val Met Leu Ala Val Ser Gln Gly Arg Val Gln Thr Asn
        50                  55                  60

Val Leu Asn Ile Ala Asn Glu Asp Cys Ile Lys Val Ala Ala Val Leu
65                  70                  75                  80

Asn Asn Ala Phe Tyr Leu Glu Asn Leu His Phe Thr Ile Glu Gly Lys
                85                  90                  95

Asp Thr His Tyr Phe Ile Lys Thr Thr Thr Pro Glu Ser Asp Leu Gly
            100                 105                 110
```

```
Thr Leu Arg Leu Thr Ser Gly Arg Lys Ala Leu Glu Asn Gly Ile Asn
        115                 120                 125

Val Thr Val Ser Gln Ser Thr Thr Val Val Asn Gly Arg Thr Arg Arg
    130                 135                 140

Phe Ala Asp Val Glu Met Gln Phe Gly Ala Leu Ala Leu His Val Arg
145                 150                 155                 160

Tyr Gly Met Thr Leu Asp Glu Glu Lys Ala Arg Ile Leu Glu Gln Ala
                165                 170                 175

Arg Gln Arg Ala Leu Ala Arg Ala Trp Ala Arg Glu Gln Gln Arg Val
            180                 185                 190

Arg Asp Gly Glu Glu Gly Ala Arg Leu Trp Thr Glu Gly Glu Lys Arg
        195                 200                 205

Gln Leu Leu Ser Ala Gly Lys Val Gln Gly Tyr Asp Gly Tyr Tyr Val
    210                 215                 220

Leu Ser Val Glu Gln Tyr Pro Glu Leu Ala Asp Ser Ala Asn Asn Ile
225                 230                 235                 240

Gln Phe Leu Arg Gln Ser Glu Ile Gly Lys Arg
                245                 250

<210> SEQ ID NO 7
<211> LENGTH: 243
<212> TYPE: PRT
<213> ORGANISM: Artificial Sequence
<220> FEATURE:
<223> OTHER INFORMATION: Mouse Ten M4

<400> SEQUENCE: 7

Ser Ile Leu Gly Val Gln Cys Glu Val Gln Lys Gln Leu Lys Ala Phe
1               5                   10                  15

Val Thr Leu Glu Arg Phe Asp Gln Leu Tyr Gly Ser Thr Ile Thr Ser
            20                  25                  30

Cys Gln Gln Ala Pro Glu Thr Lys Lys Phe Ala Ser Ser Gly Ser Ile
        35                  40                  45

Phe Gly Lys Gly Val Lys Phe Ala Leu Lys Asp Gly Arg Val Thr Thr
    50                  55                  60

Asp Ile Ile Ser Val Ala Asn Glu Asp Gly Arg Arg Ile Ala Ala Ile
65                  70                  75                  80

Leu Asn Asn Ala His Tyr Leu Glu Asn Leu His Phe Thr Ile Asp Gly
                85                  90                  95

Val Asp Thr His Tyr Phe Val Lys Pro Gly Pro Ser Glu Gly Asp Leu
            100                 105                 110

Ala Ile Leu Gly Leu Ser Gly Gly Arg Arg Thr Leu Glu Asn Gly Val
        115                 120                 125

Asn Val Thr Val Ser Gln Ile Asn Thr Met Leu Ile Gln Leu Gln Tyr
    130                 135                 140

Arg Ala Leu Cys Leu Asn Thr Arg Tyr Gly Thr Thr Val Asp Glu Glu
145                 150                 155                 160

Lys Val Arg Val Leu Glu Leu Ala Arg Gln Arg Ala Val Arg Gln Ala
                165                 170                 175

Trp Ala Arg Glu Gln Gln Arg Leu Arg Glu Gly Glu Glu Gly Leu Arg
            180                 185                 190

Ala Trp Thr Asp Gly Glu Lys Gln Gln Val Leu Asn Thr Gly Arg Val
        195                 200                 205

Gln Gly Tyr Asp Gly Phe Phe Val Thr Ser Val Glu Gln Tyr Pro Glu
    210                 215                 220
```

```
Leu Ser Asp Ser Ala Asn Asn Ile His Phe Met Arg Gln Ser Glu Met
225                 230                 235                 240

Gly Arg Arg

<210> SEQ ID NO 8
<211> LENGTH: 252
<212> TYPE: PRT
<213> ORGANISM: Artificial Sequence
<220> FEATURE:
<223> OTHER INFORMATION: Human Ten M1

<400> SEQUENCE: 8

Thr Ile Leu Gly Ile Gln Cys Glu Leu Gln Lys Gln Leu Arg Asn Phe
1               5                   10                  15

Ile Ser Leu Asp Gln Leu Pro Met Thr Pro Arg Tyr Asn Asp Gly Arg
                20                  25                  30

Cys Leu Glu Gly Gly Lys Gln Pro Arg Phe Ala Ala Val Pro Ser Val
            35                  40                  45

Phe Gly Lys Gly Ile Lys Phe Ala Ile Lys Asp Gly Ile Val Thr Ala
    50                  55                  60

Asp Ile Ile Gly Val Ala Asn Glu Asp Ser Arg Arg Leu Ala Ala Ile
65                  70                  75                  80

Leu Asn Asn Ala His Tyr Leu Glu Asn Leu His Phe Thr Ile Glu Gly
                85                  90                  95

Arg Asp Thr His Tyr Phe Ile Lys Leu Gly Ser Leu Glu Glu Asp Leu
                100                 105                 110

Val Leu Ile Gly Asn Thr Gly Gly Arg Arg Ile Leu Glu Asn Gly Val
            115                 120                 125

Asn Val Thr Val Ser Gln Met Thr Ser Val Leu Asn Gly Arg Thr Arg
130                 135                 140

Arg Phe Ala Asp Ile Gln Leu Gln His Gly Ala Leu Cys Phe Asn Ile
145                 150                 155                 160

Arg Tyr Gly Thr Thr Val Glu Glu Lys Asn His Val Leu Glu Ile
                165                 170                 175

Ala Arg Gln Arg Ala Val Ala Gln Ala Trp Thr Lys Glu Gln Arg Arg
            180                 185                 190

Leu Gln Glu Gly Glu Glu Gly Ile Arg Ala Trp Thr Glu Gly Glu Lys
        195                 200                 205

Gln Gln Leu Leu Ser Thr Gly Arg Val Gln Gly Tyr Asp Gly Tyr Phe
    210                 215                 220

Val Leu Ser Val Glu Gln Tyr Leu Glu Leu Ser Asp Ser Ala Asn Asn
225                 230                 235                 240

Ile His Phe Met Arg Gln Ser Glu Ile Gly Arg Arg
                245                 250

<210> SEQ ID NO 9
<211> LENGTH: 253
<212> TYPE: PRT
<213> ORGANISM: Artificial Sequence
<220> FEATURE:
<223> OTHER INFORMATION: Human Ten M2

<400> SEQUENCE: 9

Leu Ile Thr Gly Val Gln Gln Thr Thr Glu Arg His Asn Gln Ala Phe
1               5                   10                  15

Met Ala Leu Glu Gly Gln Val Ile Thr Lys Lys Leu His Ala Ser Ile
                20                  25                  30
```

```
Arg Glu Lys Ala Gly His Trp Phe Ala Thr Thr Pro Ile Ile Gly
        35                  40                  45

Lys Gly Ile Met Phe Ala Ile Lys Glu Gly Arg Val Thr Thr Gly Val
 50                  55                  60

Ser Ser Ile Ala Ser Glu Asp Ser Arg Lys Val Ala Ser Val Leu Asn
 65                  70                  75                  80

Asn Ala Tyr Tyr Leu Asp Lys Met His Tyr Ser Ile Glu Gly Lys Asp
                 85                  90                  95

Thr His Tyr Phe Val Lys Ile Gly Ser Ala Asp Gly Asp Leu Val Thr
            100                 105                 110

Leu Gly Thr Thr Ile Gly Arg Lys Val Leu Glu Ser Gly Val Asn Val
        115                 120                 125

Thr Val Ser Gln Pro Thr Leu Leu Val Asn Gly Arg Thr Arg Arg Phe
130                 135                 140

Thr Asn Ile Glu Phe Gln Tyr Ser Thr Leu Leu Ser Ile Arg Tyr
145                 150                 155                 160

Gly Leu Thr Pro Asp Thr Leu Asp Glu Glu Lys Ala Arg Val Leu Asp
                165                 170                 175

Gln Ala Arg Gln Arg Ala Leu Gly Thr Ala Trp Ala Lys Glu Gln Gln
            180                 185                 190

Lys Ala Arg Asp Gly Arg Glu Gly Ser Arg Leu Trp Thr Glu Gly Glu
        195                 200                 205

Lys Gln Gln Leu Leu Ser Thr Gly Arg Val Gln Gly Tyr Glu Gly Tyr
    210                 215                 220

Tyr Val Leu Pro Val Glu Gln Tyr Pro Glu Leu Ala Asp Ser Ser Ser
225                 230                 235                 240

Asn Ile Gln Phe Leu Arg Gln Asn Glu Met Gly Lys Arg
                245                 250

<210> SEQ ID NO 10
<211> LENGTH: 251
<212> TYPE: PRT
<213> ORGANISM: Artificial Sequence
<220> FEATURE:
<223> OTHER INFORMATION: Human Ten M3

<400> SEQUENCE: 10

Pro Ile Phe Gly Val Gln Gln Val Ala Arg Gln Ala Lys Ala Phe
1               5                   10                  15

Leu Ser Leu Gly Lys Met Ala Glu Val Gln Val Ser Arg Arg Arg Ala
            20                  25                  30

Gly Gly Ala Gln Ser Trp Leu Trp Phe Ala Thr Val Lys Ser Leu Ile
        35                  40                  45

Gly Lys Gly Val Met Leu Ala Val Ser Gln Gly Arg Val Gln Thr Asn
 50                  55                  60

Val Leu Asn Ile Ala Asn Glu Asp Cys Ile Lys Val Ala Ala Val Leu
 65                  70                  75                  80

Asn Asn Ala Phe Tyr Leu Glu Asn Leu His Phe Thr Ile Glu Gly Lys
                 85                  90                  95

Asp Thr His Tyr Phe Ile Lys Thr Thr Thr Pro Glu Ser Asp Leu Gly
            100                 105                 110

Thr Leu Arg Leu Thr Ser Gly Arg Lys Ala Leu Glu Asn Gly Ile Asn
        115                 120                 125

Val Thr Val Ser Gln Ser Thr Val Val Asn Gly Arg Thr Arg Arg
130                 135                 140
```

```
Phe Ala Asp Val Glu Met Gln Phe Gly Ala Leu Ala Leu His Val Arg
145                 150                 155                 160

Tyr Gly Met Thr Leu Asp Glu Glu Lys Ala Arg Ile Leu Glu Gln Ala
            165                 170                 175

Arg Gln Arg Ala Leu Ala Arg Ala Trp Ala Arg Glu Gln Gln Arg Val
        180                 185                 190

Arg Asp Gly Glu Glu Gly Ala Arg Leu Trp Thr Glu Gly Lys Arg
            195                 200                 205

Gln Leu Leu Ser Ala Gly Lys Val Gln Gly Tyr Asp Gly Tyr Tyr Val
        210                 215                 220

Leu Ser Val Glu Gln Tyr Pro Glu Leu Ala Asp Ser Ala Asn Asn Ile
225                 230                 235                 240

Gln Phe Leu Arg Gln Ser Glu Ile Gly Arg Arg
                245                 250

<210> SEQ ID NO 11
<211> LENGTH: 252
<212> TYPE: PRT
<213> ORGANISM: Artificial Sequence
<220> FEATURE:
<223> OTHER INFORMATION: Human Ten M4

<400> SEQUENCE: 11

Ser Ile Leu Gly Val Gln Cys Glu Val Gln Lys Gln Leu Lys Ala Phe
1               5                   10                  15

Val Thr Leu Glu Arg Phe Asp Gln Leu Tyr Gly Ser Thr Ile Thr Ser
            20                  25                  30

Cys Leu Gln Ala Pro Lys Thr Lys Lys Phe Ala Ser Ser Gly Ser Val
        35                  40                  45

Phe Gly Lys Gly Val Lys Phe Ala Leu Lys Asp Gly Arg Val Thr Thr
    50                  55                  60

Asp Ile Ile Ser Val Ala Asn Glu Asp Gly Arg Arg Val Ala Ala Ile
65                  70                  75                  80

Leu Asn His Ala His Tyr Leu Glu Asn Leu His Phe Thr Ile Asp Gly
                85                  90                  95

Val Asp Thr His Tyr Phe Val Lys Pro Gly Pro Ser Glu Gly Asp Leu
            100                 105                 110

Ala Ile Leu Gly Leu Ser Gly Gly Arg Arg Thr Leu Glu Asn Gly Val
        115                 120                 125

Asn Val Thr Val Ser Gln Ile Asn Thr Val Leu Ser Gly Arg Thr Arg
    130                 135                 140

Arg Tyr Thr Asp Ile Gln Leu Gln Tyr Gly Ala Leu Cys Leu Asn Thr
145                 150                 155                 160

Arg Tyr Gly Thr Thr Leu Asp Glu Glu Lys Ala Arg Val Leu Glu Leu
                165                 170                 175

Ala Arg Gln Arg Ala Val Arg Gln Ala Trp Ala Arg Glu Gln Gln Arg
            180                 185                 190

Leu Arg Glu Gly Glu Glu Gly Leu Arg Ala Trp Thr Glu Gly Glu Lys
        195                 200                 205

Gln Gln Val Leu Ser Thr Gly Arg Val Gln Gly Tyr Asp Gly Phe Phe
    210                 215                 220

Val Ile Ser Val Glu Gln Tyr Pro Glu Leu Ser Asp Ser Ala Asn Asn
225                 230                 235                 240

Ile His Phe Met Arg Gln Ser Glu Met Gly Arg Arg
                245                 250
```

```
<210> SEQ ID NO 12
<211> LENGTH: 252
<212> TYPE: PRT
<213> ORGANISM: Artificial Sequence
<220> FEATURE:
<223> OTHER INFORMATION: Zebrafish Ten M3

<400> SEQUENCE: 12

Ser Ile Ser Gly Val Gln Gln Glu Val Met Arg Gln Ala Lys Ala Phe
1               5                   10                  15

Leu Ser Phe Glu Arg Met Pro Glu Ile Gln Leu Ser Arg Arg Arg Ser
            20                  25                  30

Ser Arg Glu Lys Pro Trp Leu Trp Phe Ala Thr Val Lys Ser Leu Ile
        35                  40                  45

Gly Lys Gly Val Met Leu Ala Ile Thr Ser Lys Gly Gln Val Ala Thr
    50                  55                  60

Asn Ala Leu Asn Ile Ala Asn Glu Asp Cys Ile Lys Val Val Thr Val
65                  70                  75                  80

Leu Asn Asn Ala Phe Tyr Leu Glu Asp Leu His Phe Thr Val Glu Gly
                85                  90                  95

Arg Asp Thr His Tyr Phe Ile Lys Thr Ser Leu Pro Glu Ser Asp Leu
            100                 105                 110

Gly Ala Leu Arg Leu Thr Ser Gly Arg Lys Ser Leu Glu Asn Gly Val
        115                 120                 125

Asn Val Thr Val Ser Gln Ser Thr Thr Val Val Asn Gly Arg Thr Arg
    130                 135                 140

Arg Phe Ala Asp Val Glu Leu Gln Tyr Gly Ala Leu Ala Leu His Val
145                 150                 155                 160

Arg Tyr Gly Met Thr Leu Asp Glu Glu Lys Ala Arg Val Leu Glu Gln
                165                 170                 175

Ala Arg Gln Arg Ala Leu Ser Ser Ala Trp Ala Arg Glu Gln Gln Arg
            180                 185                 190

Val Arg Asp Gly Glu Glu Gly Val Arg Leu Trp Thr Glu Gly Glu Lys
        195                 200                 205

Arg Gln Leu Leu Ser Ser Gly Lys Val Leu Gly Tyr Asp Gly Tyr Tyr
    210                 215                 220

Val Leu Ser Val Glu Gln Tyr Pro Glu Leu Ala Asp Ser Ala Asn Asn
225                 230                 235                 240

Val Gln Phe Leu Arg Gln Ser Glu Ile Gly Lys Arg
                245                 250

<210> SEQ ID NO 13
<211> LENGTH: 40
<212> TYPE: PRT
<213> ORGANISM: Artificial Sequence
<220> FEATURE:
<223> OTHER INFORMATION: Rainbow Trout TCAP3 (40a.a.)

<400> SEQUENCE: 13

Gln Leu Leu Ser Gly Arg Lys Val Leu Gly Tyr Asp Gly Tyr Tyr Val
1               5                   10                  15

Leu Ser Ile Glu Gln Tyr Pro Glu Leu Ala Asp Ser Ala Asn Asn Ile
            20                  25                  30

Gln Phe Leu Arg Gln Ser Glu Ile
        35                  40
```

```
<210> SEQ ID NO 14
<211> LENGTH: 41
<212> TYPE: PRT
<213> ORGANISM: Artificial Sequence
<220> FEATURE:
<223> OTHER INFORMATION: Rainbow Trout TCAP 3 (41a.a.)

<400> SEQUENCE: 14

Arg Gln Leu Leu Ser Gly Arg Lys Val Leu Gly Tyr Asp Gly Tyr Tyr
 1               5                  10                  15

Val Leu Ser Ile Glu Gln Tyr Pro Glu Leu Ala Asp Ser Ala Asn Asn
            20                  25                  30

Ile Gln Phe Leu Arg Gln Ser Glu Ile
        35                  40

<210> SEQ ID NO 15
<211> LENGTH: 43
<212> TYPE: PRT
<213> ORGANISM: Artificial Sequence
<220> FEATURE:
<223> OTHER INFORMATION: Rainbow Trout preTCAP3 (43 a.a.)

<400> SEQUENCE: 15

Gln Leu Leu Ser Gly Arg Lys Val Leu Gly Tyr Asp Gly Tyr Tyr Val
 1               5                  10                  15

Leu Ser Ile Glu Gln Tyr Pro Glu Leu Ala Asp Ser Ala Asn Asn Ile
            20                  25                  30

Gln Phe Leu Arg Gln Ser Glu Ile Gly Lys Arg
        35                  40

<210> SEQ ID NO 16
<211> LENGTH: 44
<212> TYPE: PRT
<213> ORGANISM: Artificial Sequence
<220> FEATURE:
<223> OTHER INFORMATION: Rainbow Trout preTCAP3 (44 a.a.)

<400> SEQUENCE: 16

Arg Gln Leu Leu Ser Gly Arg Lys Val Leu Gly Tyr Asp Gly Tyr Tyr
 1               5                  10                  15

Val Leu Ser Ile Glu Gln Tyr Pro Glu Leu Ala Asp Ser Ala Asn Asn
            20                  25                  30

Ile Gln Phe Leu Arg Gln Ser Glu Ile Gly Lys Arg
        35                  40

<210> SEQ ID NO 17
<211> LENGTH: 120
<212> TYPE: DNA
<213> ORGANISM: Artificial Sequence
<220> FEATURE:
<223> OTHER INFORMATION: Rainbow Trout TCAP3 (120 n.a.)

<400> SEQUENCE: 17
cagctgctga gcgggaggaa ggttctgggc tacgacgggt actacgtcct ctccatagag      60
cagtaccccg agctagcaga ctccgctaac aacatccagt tcctcaggca gagcgaaata     120

<210> SEQ ID NO 18
<211> LENGTH: 123
<212> TYPE: DNA
<213> ORGANISM: Artificial Sequence
<220> FEATURE:
<223> OTHER INFORMATION: Rainbow Trout TCAP3 (123 n.a.)

<400> SEQUENCE: 18
```

-continued

```
aggcagctgc tgagcgggag gaaggttctg ggctacgacg ggtactacgt cctctccata    60
gagcagtacc ccgagctagc agactccgct aacaacatcc agttcctcag gcagagcgaa   120
ata                                                                 123
```

<210> SEQ ID NO 19
<211> LENGTH: 129
<212> TYPE: DNA
<213> ORGANISM: Artificial Sequence
<220> FEATURE:
<223> OTHER INFORMATION: Rainbow Trout preTCAP3 (129 n.a.)

<400> SEQUENCE: 19

```
cagctgctga gcgggaggaa ggttctgggc tacgacgggt actacgtcct ctccatagag    60
cagtaccccg agctagcaga ctccgctaac aacatccagt tcctcaggca gagcgaaata   120
gggaagagg                                                           129
```

<210> SEQ ID NO 20
<211> LENGTH: 132
<212> TYPE: DNA
<213> ORGANISM: Artificial Sequence
<220> FEATURE:
<223> OTHER INFORMATION: Rainbow Trout preTCAP3 (132 n.a.)

<400> SEQUENCE: 20

```
aggcagctgc tgagcgggag gaaggttctg ggctacgacg ggtactacgt cctctccata    60
gagcagtacc ccgagctagc agactccgct aacaacatcc agttcctcag gcagagcgaa   120
atagggaaga gg                                                       132
```

<210> SEQ ID NO 21
<211> LENGTH: 40
<212> TYPE: PRT
<213> ORGANISM: Artificial Sequence
<220> FEATURE:
<223> OTHER INFORMATION: Zebrafish TCAP3 (40 a.a.)

<400> SEQUENCE: 21

```
Gln Leu Leu Ser Ser Gly Lys Val Leu Gly Tyr Asp Gly Tyr Tyr Val
1               5                   10                  15

Leu Ser Val Glu Gln Tyr Pro Glu Leu Ala Asp Ser Ala Asn Asn Val
            20                  25                  30

Gln Phe Leu Arg Gln Ser Glu Ile
        35                  40
```

<210> SEQ ID NO 22
<211> LENGTH: 41
<212> TYPE: PRT
<213> ORGANISM: Artificial Sequence
<220> FEATURE:
<223> OTHER INFORMATION: Zebrafish TCAP3 (41 a.a.)

<400> SEQUENCE: 22

```
Arg Gln Leu Leu Ser Ser Gly Lys Val Leu Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Val Gln Phe Leu Arg Gln Ser Glu Ile
        35                  40
```

<210> SEQ ID NO 23

```
<211> LENGTH: 43
<212> TYPE: PRT
<213> ORGANISM: Artificial Sequence
<220> FEATURE:
<223> OTHER INFORMATION: Zebrafish preTCAP3 (43 a.a.)

<400> SEQUENCE: 23

Gln Leu Leu Ser Ser Gly Lys Val Leu Gly Tyr Asp Gly Tyr Tyr Val
1               5                   10                  15

Leu Ser Val Glu Gln Tyr Pro Glu Leu Ala Asp Ser Ala Asn Asn Val
            20                  25                  30

Gln Phe Leu Arg Gln Ser Glu Ile Gly Lys Arg
        35                  40

<210> SEQ ID NO 24
<211> LENGTH: 44
<212> TYPE: PRT
<213> ORGANISM: Artificial Sequence
<220> FEATURE:
<223> OTHER INFORMATION: Zebrafish preTCAP3 (44 a.a.)

<400> SEQUENCE: 24

Arg Gln Leu Leu Ser Ser Gly Lys Val Leu Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Val Gln Phe Leu Arg Gln Ser Glu Ile Gly Lys Arg
        35                  40

<210> SEQ ID NO 25
<211> LENGTH: 120
<212> TYPE: DNA
<213> ORGANISM: Artificial Sequence
<220> FEATURE:
<223> OTHER INFORMATION: Zebrafish TCAP3 (120 n.a.)

<400> SEQUENCE: 25
cagttgctca gctctgggaa ggtgctgggt tacgatggtt actatgtact atcagtggag      60 caatacccctg aactggccga cagtgccaac aatgtccagt tcttgaggca gagtgagata    120

<210> SEQ ID NO 26
<211> LENGTH: 123
<212> TYPE: DNA
<213> ORGANISM: Artificial Sequence
<220> FEATURE:
<223> OTHER INFORMATION: Zebrafish TCAP3 (123 n.a.)

<400> SEQUENCE: 26
aggcagttgc tcagctctgg gaaggtgctg ggttacgatg gttactatgt actatcagtg      60
gagcaatacc ctgaactggc cgacagtgcc aacaatgtcc agttcttgag gcagagtgag    120
ata                                                                   123

<210> SEQ ID NO 27
<211> LENGTH: 129
<212> TYPE: DNA
<213> ORGANISM: Artificial Sequence
<220> FEATURE:
<223> OTHER INFORMATION: Zebrafish TCAP3 (129 n.a.)

<400> SEQUENCE: 27
cagttgctca gctctgggaa ggtgctgggt tacgatggtt actatgtact atcagtggag      60 caatacccctg aactggccga cagtgccaac aatgtccagt tcttgaggca gagtgagata    120
```

-continued

```
gggaagagg                                                              129

<210> SEQ ID NO 28
<211> LENGTH: 132
<212> TYPE: DNA
<213> ORGANISM: Artificial Sequence
<220> FEATURE:
<223> OTHER INFORMATION: Zebrafish preTCAP3 (132 n.a.)

<400> SEQUENCE: 28
aggcagttgc tcagctctgg gaaggtgctg ggttacgatg gttactatgt actatcagtg      60
gagcaatacc ctgaactggc cgacagtgcc aacaatgtcc agttcttgag cagagtgag     120 atagggaaga gg                                                         132

<210> SEQ ID NO 29
<211> LENGTH: 40
<212> TYPE: PRT
<213> ORGANISM: Artificial Sequence
<220> FEATURE:
<223> OTHER INFORMATION: Zebrafish TCAP4 (40 a.a.)

<400> SEQUENCE: 29

Gln Leu Leu Ser Ser Gly Arg Val Gln Gly Tyr Glu Gly Phe Tyr Ile
1               5                   10                  15

Val Ser Val Asp Gln Phe Pro Glu Leu Thr Asp Asn Ile Asn Asn Val
            20                  25                  30

His Phe Trp Arg Gln Thr Glu Met
        35                  40

<210> SEQ ID NO 30
<211> LENGTH: 41
<212> TYPE: PRT
<213> ORGANISM: Artificial Sequence
<220> FEATURE:
<223> OTHER INFORMATION: Zebrafish TCAP4 (41 a.a.)

<400> SEQUENCE: 30

Gln Gln Leu Leu Ser Ser Gly Arg Val Gln Gly Tyr Glu Gly Phe Tyr
1               5                   10                  15

Ile Val Ser Val Asp Gln Phe Pro Glu Leu Thr Asp Asn Ile Asn Asn
            20                  25                  30

Val His Phe Trp Arg Gln Thr Glu Met
        35                  40

<210> SEQ ID NO 31
<211> LENGTH: 43
<212> TYPE: PRT
<213> ORGANISM: Artificial Sequence
<220> FEATURE:
<223> OTHER INFORMATION: Zebrafish preTCAP4 (43 a.a.)

<400> SEQUENCE: 31

Gln Leu Leu Ser Ser Gly Arg Val Gln Gly Tyr Glu Gly Phe Tyr Ile
1               5                   10                  15

Val Ser Val Asp Gln Phe Pro Glu Leu Thr Asp Asn Ile Asn Asn Val
            20                  25                  30

His Phe Trp Arg Gln Thr Glu Met Gly Arg Arg
        35                  40

<210> SEQ ID NO 32
<211> LENGTH: 44
```

```
<212> TYPE: PRT
<213> ORGANISM: Artificial Sequence
<220> FEATURE:
<223> OTHER INFORMATION: Zebrafish preTCAP4 (44 a.a.)

<400> SEQUENCE: 32

Gln Gln Leu Leu Ser Ser Gly Arg Val Gln Gly Tyr Glu Gly Phe Tyr
1               5                   10                  15

Ile Val Ser Val Asp Gln Phe Pro Glu Leu Thr Asp Asn Ile Asn Asn
            20                  25                  30

Val His Phe Trp Arg Gln Thr Glu Met Gly Arg Arg
        35                  40

<210> SEQ ID NO 33
<211> LENGTH: 120
<212> TYPE: DNA
<213> ORGANISM: Artificial Sequence
<220> FEATURE:
<223> OTHER INFORMATION: Zebrafish TCAP4 (120 n.a.)

<400> SEQUENCE: 33
cagctcctaa gctctggacg tgtacagggc tacgaaggct tctacatagt atcagtcgac      60
cagttcccag agttgactga caacataaat aacgtccatt tctggcgaca gactgagatg     120

<210> SEQ ID NO 34
<211> LENGTH: 123
<212> TYPE: DNA
<213> ORGANISM: Artificial Sequence
<220> FEATURE:
<223> OTHER INFORMATION: Zebrafish TCAP4 (123 n.a.)

<400> SEQUENCE: 34
cagcagctcc taagctctgg acgtgtacag ggctacgaag gcttctacat agtatcagtc      60
gaccagttcc cagagttgac tgacaacata aataacgtcc atttctggcg acagactgag     120
atg                                                                   123

<210> SEQ ID NO 35
<211> LENGTH: 129
<212> TYPE: DNA
<213> ORGANISM: Artificial Sequence
<220> FEATURE:
<223> OTHER INFORMATION: Zebrafish preTCAP4 (129 n.a.)

<400> SEQUENCE: 35
cagctcctaa gctctggacg tgtacagggc tacgaaggct tctacatagt atcagtcgac      60
cagttcccag agttgactga caacataaat aacgtccatt tctggcgaca gactgagatg     120
ggacgcagg                                                             129

<210> SEQ ID NO 36
<211> LENGTH: 132
<212> TYPE: DNA
<213> ORGANISM: Artificial Sequence
<220> FEATURE:
<223> OTHER INFORMATION: Zebrafish preTCAP4 (132 n.a.)

<400> SEQUENCE: 36
cagcagctcc taagctctgg acgtgtacag ggctacgaag gcttctacat agtatcagtc      60
gaccagttcc cagagttgac tgacaacata aataacgtcc atttctggcg acagactgag     120
atgggacgca gg                                                         132
```

-continued

```
<210> SEQ ID NO 37
<211> LENGTH: 40
<212> TYPE: PRT
<213> ORGANISM: Artificial Sequence
<220> FEATURE:
<223> OTHER INFORMATION: Mouse TCAP1 (40 a.a.)

<400> SEQUENCE: 37

Gln Leu Leu Gly Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile
        35                  40

<210> SEQ ID NO 38
<211> LENGTH: 41
<212> TYPE: PRT
<213> ORGANISM: Artificial Sequence
<220> FEATURE:
<223> OTHER INFORMATION: Mouse TCAP1 (41 a.a.)

<400> SEQUENCE: 38

Gln Gln Leu Leu Gly Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile
        35                  40

<210> SEQ ID NO 39
<211> LENGTH: 43
<212> TYPE: PRT
<213> ORGANISM: Artificial Sequence
<220> FEATURE:
<223> OTHER INFORMATION: Mouse preTCAP1 (43 a.a.)

<400> SEQUENCE: 39

Gln Leu Leu Gly Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile Gly Arg Arg
        35                  40

<210> SEQ ID NO 40
<211> LENGTH: 44
<212> TYPE: PRT
<213> ORGANISM: Artificial Sequence
<220> FEATURE:
<223> OTHER INFORMATION: Mouse preTCAP1 (44 a.a.)

<400> SEQUENCE: 40

Gln Gln Leu Leu Gly Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile Gly Arg Arg
        35                  40

<210> SEQ ID NO 41
<211> LENGTH: 120
<212> TYPE: DNA
```

```
<213> ORGANISM: Artificial Sequence
<220> FEATURE:
<223> OTHER INFORMATION: Mouse TCAP1 (120 n.a.)

<400> SEQUENCE: 41
cagcttttgg gcaccgggag ggtgcagggg tatgatgggt attttgtctt gtctgttgag      60
cagtatttag aactttcaga cagtgccaac aatattcact tcatgagaca gagtgaaata     120

<210> SEQ ID NO 42
<211> LENGTH: 123
<212> TYPE: DNA
<213> ORGANISM: Artificial Sequence
<220> FEATURE:
<223> OTHER INFORMATION: Mouse TCAP1 (123 n.a.)

<400> SEQUENCE: 42
cagcagcttt tgggcaccgg gagggtgcag gggtatgatg gtattttgt cttgtctgtt      60 gagcagtatt tagaactttc agacagtgcc aacaatattc acttcatgag acagagtgaa     120
ata                                                                   123

<210> SEQ ID NO 43
<211> LENGTH: 129
<212> TYPE: DNA
<213> ORGANISM: Artificial Sequence
<220> FEATURE:
<223> OTHER INFORMATION: Mouse preTCAP1 (129 n.a.)

<400> SEQUENCE: 43
cagcttttgg gcaccgggag ggtgcagggg tatgatgggt attttgtctt gtctgttgag      60
cagtatttag aactttcaga cagtgccaac aatattcact tcatgagaca gagtgaaata     120
ggcaggagg                                                             129

<210> SEQ ID NO 44
<211> LENGTH: 132
<212> TYPE: DNA
<213> ORGANISM: Artificial Sequence
<220> FEATURE:
<223> OTHER INFORMATION: Mouse preTCAP1 (132 n.a.)

<400> SEQUENCE: 44
cagcagcttt tgggcaccgg gagggtgcag gggtatgatg gtattttgt cttgtctgtt       60 gagcagtatt tagaactttc agacagtgcc aacaatattc acttcatgag acagagtgaa     120
ataggcagga gg                                                         132

<210> SEQ ID NO 45
<211> LENGTH: 40
<212> TYPE: PRT
<213> ORGANISM: Artificial Sequence
<220> FEATURE:
<223> OTHER INFORMATION: Mouse TCAP2 (40 a.a.)

<400> SEQUENCE: 45

Gln Leu Leu Ser Thr Gly Arg Val Gln Gly Tyr Glu Gly Tyr Tyr Val
1               5                   10                  15

Leu Pro Val Glu Gln Tyr Pro Glu Leu Ala Asp Ser Ser Ser Asn Ile
            20                  25                  30

Gln Phe Leu Arg Gln Asn Glu Ile
        35                  40

<210> SEQ ID NO 46
```

```
<211> LENGTH: 41
<212> TYPE: PRT
<213> ORGANISM: Artificial Sequence
<220> FEATURE:
<223> OTHER INFORMATION: Mouse TCAP2 (41 a.a.)

<400> SEQUENCE: 46

Gln Gln Leu Leu Ser Thr Gly Arg Val Gln Gly Tyr Glu Gly Tyr Tyr
1               5                   10                  15

Val Leu Pro Val Glu Gln Tyr Pro Glu Leu Ala Asp Ser Ser Ser Asn
            20                  25                  30

Ile Gln Phe Leu Arg Gln Asn Glu Met
        35                  40

<210> SEQ ID NO 47
<211> LENGTH: 43
<212> TYPE: PRT
<213> ORGANISM: Artificial Sequence
<220> FEATURE:
<223> OTHER INFORMATION: Mouse preTCAP2 (43 a.a)

<400> SEQUENCE: 47

Gln Leu Leu Ser Thr Gly Arg Val Gln Gly Tyr Glu Gly Tyr Tyr Val
1               5                   10                  15

Leu Pro Val Glu Gln Tyr Pro Glu Leu Ala Asp Ser Ser Ser Asn Ile
            20                  25                  30

Gln Phe Leu Arg Gln Asn Glu Met Gly Lys Arg
        35                  40

<210> SEQ ID NO 48
<211> LENGTH: 44
<212> TYPE: PRT
<213> ORGANISM: Artificial Sequence
<220> FEATURE:
<223> OTHER INFORMATION: Mouse preTCAP2 (44 a.a.)

<400> SEQUENCE: 48

Gln Gln Leu Leu Ser Thr Gly Arg Val Gln Gly Tyr Glu Gly Tyr Tyr
1               5                   10                  15

Val Leu Pro Val Glu Gln Tyr Pro Glu Leu Ala Asp Ser Ser Ser Asn
            20                  25                  30

Ile Gln Phe Leu Arg Gln Asn Glu Met Gly Lys Arg
        35                  40

<210> SEQ ID NO 49
<211> LENGTH: 120
<212> TYPE: DNA
<213> ORGANISM: Artificial Sequence
<220> FEATURE:
<223> OTHER INFORMATION: Mouse TCAP2 (120 n.a.)

<400> SEQUENCE: 49
caactcctga gcacgggacg ggtacaaggt tatgagggct attacgtact tccggtggaa      60
cagtacccgg agctggcaga cagtagcagc aacatccagt tcttaagaca gaatgagagg     120

<210> SEQ ID NO 50
<211> LENGTH: 123
<212> TYPE: DNA
<213> ORGANISM: Artificial Sequence
<220> FEATURE:
<223> OTHER INFORMATION: Mouse TCAP 2 (123 n.a.)

<400> SEQUENCE: 50
```

```
cagcaactcc tgagcacggg acgggtacaa ggttatgagg gctattacgt acttccggtg    60
gaacagtacc cggagctggc agacagtagc agcaacatcc agttcttaag acagaatgag  120
atg                                                                123
```

<210> SEQ ID NO 51
<211> LENGTH: 129
<212> TYPE: DNA
<213> ORGANISM: Artificial Sequence
<220> FEATURE:
<223> OTHER INFORMATION: Mouse preTCAP2 (129 n.a.)

<400> SEQUENCE: 51

```
caactcctga gcacgggacg ggtacaaggt tatgagggct attacgtact tccggtggaa    60
cagtacccgg agctggcaga cagtagcagc aacatccagt tcttaagaca gaatgagatg  120
ggaaagagg                                                          129
```

<210> SEQ ID NO 52
<211> LENGTH: 132
<212> TYPE: DNA
<213> ORGANISM: Artificial Sequence
<220> FEATURE:
<223> OTHER INFORMATION: Mouse preTCAP2 (132 n.a.)

<400> SEQUENCE: 52

```
cagcaactcc tgagcacggg acgggtacaa ggttatgagg gctattacgt acttccggtg    60
gaacagtacc cggagctggc agacagtagc agcaacatcc agttcttaag acagaatgag  120
atgggaaaga gg                                                      132
```

<210> SEQ ID NO 53
<211> LENGTH: 40
<212> TYPE: PRT
<213> ORGANISM: Artificial Sequence
<220> FEATURE:
<223> OTHER INFORMATION: Mouse TCAP3 (40 a.a.)

<400> SEQUENCE: 53

```
Gln Leu Leu Ser Ala Gly Lys Val Gln Gly Tyr Asp Gly Tyr Tyr Val
1               5                  10                  15

Leu Ser Val Glu Gln Tyr Pro Glu Leu Ala Asp Ser Ala Asn Asn Ile
            20                  25                  30

Gln Phe Leu Arg Gln Ser Glu Ile
        35                  40
```

<210> SEQ ID NO 54
<211> LENGTH: 41
<212> TYPE: PRT
<213> ORGANISM: Artificial Sequence
<220> FEATURE:
<223> OTHER INFORMATION: Mouse TCAP3 (41 a..a)

<400> SEQUENCE: 54

```
Arg Gln Leu Leu Ser Ala Gly Lys Val Gln Gly Tyr Asp Gly Tyr Tyr
1               5                  10                  15

Val Leu Ser Val Glu Gln Tyr Pro Glu Leu Ala Asp Ser Ala Asn Asn
            20                  25                  30

Ile Gln Phe Leu Arg Gln Ser Glu Ile
        35                  40
```

<210> SEQ ID NO 55
<211> LENGTH: 43

```
<212> TYPE: PRT
<213> ORGANISM: Artificial Sequence
<220> FEATURE:
<223> OTHER INFORMATION: Mouse preTCAP3 (43 a.a.)

<400> SEQUENCE: 55

Gln Leu Leu Ser Ala Gly Lys Val Gln Gly Tyr Asp Gly Tyr Tyr Val
1               5                   10                  15

Leu Ser Val Glu Gln Tyr Pro Glu Leu Ala Asp Ser Ala Asn Asn Ile
            20                  25                  30

Gln Phe Leu Arg Gln Ser Glu Ile Gly Lys Arg
        35                  40

<210> SEQ ID NO 56
<211> LENGTH: 44
<212> TYPE: PRT
<213> ORGANISM: Artificial Sequence
<220> FEATURE:
<223> OTHER INFORMATION: Mouse preTCAP3 (44 a.a.)

<400> SEQUENCE: 56

Arg Gln Leu Leu Ser Ala Gly Lys Val Gln Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Ile Gln Phe Leu Arg Gln Ser Glu Ile Gly Lys Arg
        35                  40

<210> SEQ ID NO 57
<211> LENGTH: 120
<212> TYPE: DNA
<213> ORGANISM: Artificial Sequence
<220> FEATURE:
<223> OTHER INFORMATION: Mouse TCAP3 (120 n.a.)

<400> SEQUENCE: 57
cagctgctga gcgctggcaa ggtgcagggc tacgatgggt actacgtact gtcggtggag      60
cagtaccccg agctggctga cagtgccaac aacatccagt tcttgcgaca aagtgagatc     120

<210> SEQ ID NO 58
<211> LENGTH: 123
<212> TYPE: DNA
<213> ORGANISM: Artificial Sequence
<220> FEATURE:
<223> OTHER INFORMATION: Mouse TCAP3 (123 n.a.)

<400> SEQUENCE: 58
cggcagctgc tgagcgctgg caaggtgcag ggctacgatg gtactacgt actgtcggtg       60 gagcagtacc ccgagctggc tgacagtgcc aacaacatcc agttcttgcg acaaagtgag    120
atc                                                                  123

<210> SEQ ID NO 59
<211> LENGTH: 129
<212> TYPE: DNA
<213> ORGANISM: Artificial Sequence
<220> FEATURE:
<223> OTHER INFORMATION: Mouse preTCAP3 (129 n.a.)

<400> SEQUENCE: 59
cagctgctga gcgctggcaa ggtgcagggc tacgatgggt actacgtact gtcggtggag      60
cagtaccccg agctggctga cagtgccaac aacatccagt tcttgcgaca aagtgagatc    120
```

```
ggcaagagg                                                              129

<210> SEQ ID NO 60
<211> LENGTH: 132
<212> TYPE: DNA
<213> ORGANISM: Artificial Sequence
<220> FEATURE:
<223> OTHER INFORMATION: Mouse preTCAP3 (132 n.a.)

<400> SEQUENCE: 60
cggcagctgc tgagcgctgg caaggtgcag ggctacgatg gtactacgt  actgtcggtg      60 gagcagtacc ccgagctggc tgacagtgcc aacaacatcc agttcttgcg acaaagtgag     120
atcggcaaga gg                                                         132

<210> SEQ ID NO 61
<211> LENGTH: 40
<212> TYPE: PRT
<213> ORGANISM: Artificial Sequence
<220> FEATURE:
<223> OTHER INFORMATION: Mouse TCAP4 (40 a.a.)

<400> SEQUENCE: 61

Gln Val Leu Asn Thr Gly Arg Val Gln Gly Tyr Asp Gly Phe Phe Val
1               5                   10                  15

Thr Ser Val Glu Gln Tyr Pro Glu Leu Ser Asp Ser Ala Asn Asn Ile
            20                  25                  30

His Phe Met Arg Gln Ser Glu Met
        35                  40

<210> SEQ ID NO 62
<211> LENGTH: 41
<212> TYPE: PRT
<213> ORGANISM: Artificial Sequence
<220> FEATURE:
<223> OTHER INFORMATION: Mouse TCAP4 (41 a.a.)

<400> SEQUENCE: 62

Gln Gln Val Leu Asn Thr Gly Arg Val Gln Gly Tyr Asp Gly Phe Phe
1               5                   10                  15

Val Thr Ser Val Glu Gln Tyr Pro Glu Leu Ser Asp Ser Ala Asn Asn
            20                  25                  30

Ile His Phe Met Arg Gln Ser Glu Met
        35                  40

<210> SEQ ID NO 63
<211> LENGTH: 43
<212> TYPE: PRT
<213> ORGANISM: Artificial Sequence
<220> FEATURE:
<223> OTHER INFORMATION: Mouse preTCAP4 (43 a.a.)

<400> SEQUENCE: 63

Gln Val Leu Asn Thr Gly Arg Val Gln Gly Tyr Asp Gly Phe Phe Val
1               5                   10                  15

Thr Ser Val Glu Gln Tyr Pro Glu Leu Ser Asp Ser Ala Asn Asn Ile
            20                  25                  30

His Phe Met Arg Gln Ser Glu Met Gly Arg Arg
        35                  40

<210> SEQ ID NO 64
<211> LENGTH: 44
<212> TYPE: PRT
```

```
<213> ORGANISM: Artificial Sequence
<220> FEATURE:
<223> OTHER INFORMATION: Mouse preTCAP4 (44 a.a.)

<400> SEQUENCE: 64

Gln Gln Val Leu Asn Thr Gly Arg Val Gln Gly Tyr Asp Gly Phe Phe
1               5                   10                  15

Val Thr Ser Val Glu Gln Tyr Pro Glu Leu Ser Asp Ser Ala Asn Asn
                20                  25                  30

Ile His Phe Met Arg Gln Ser Glu Met Gly Arg Arg
            35                  40

<210> SEQ ID NO 65
<211> LENGTH: 120
<212> TYPE: DNA
<213> ORGANISM: Artificial Sequence
<220> FEATURE:
<223> OTHER INFORMATION: Mouse TCAP4 (120 n.a.)

<400> SEQUENCE: 65
caggtgctga acacggggcg ggtgcaaggc tacgacggct tctttgtgac ctcggtcgag      60
cagtacccag aactgtcaga cagcgccaac aatatccact tcatgagaca gagcgagatg    120

<210> SEQ ID NO 66
<211> LENGTH: 123
<212> TYPE: DNA
<213> ORGANISM: Artificial Sequence
<220> FEATURE:
<223> OTHER INFORMATION: Mouse TCAP4 (123 n.a.)

<400> SEQUENCE: 66
cagcaggtgc tgaacacggg gcgggtgcaa ggctacgacg gcttctttgt gacctcggtc      60
gagcagtacc cagaactgtc agacagcgcc aacaatatcc acttcatgag acagagcgag    120
atg                                                                  123

<210> SEQ ID NO 67
<211> LENGTH: 129
<212> TYPE: DNA
<213> ORGANISM: Artificial Sequence
<220> FEATURE:
<223> OTHER INFORMATION: Mouse preTCAP4 (129 n.a.)

<400> SEQUENCE: 67
caggtgctga acacggggcg ggtgcaaggc tacgacggct tctttgtgac ctcggtcgag      60
cagtacccag aactgtcaga cagcgccaac aatatccact tcatgagaca gagcgagatg    120
ggccgaagg                                                            129

<210> SEQ ID NO 68
<211> LENGTH: 132
<212> TYPE: DNA
<213> ORGANISM: Artificial Sequence
<220> FEATURE:
<223> OTHER INFORMATION: Mouse preTCAP4 (132 n.a.)

<400> SEQUENCE: 68
cagcaggtgc tgaacacggg gcgggtgcaa ggctacgacg gcttctttgt gacctcggtc      60
gagcagtacc cagaactgtc agacagcgcc aacaatatcc acttcatgag acagagcgag    120
atgggccgaa gg                                                        132

<210> SEQ ID NO 69
```

-continued

```
<211> LENGTH: 40
<212> TYPE: PRT
<213> ORGANISM: Artificial Sequence
<220> FEATURE:
<223> OTHER INFORMATION: Human TCAP1 (40 a.a.)

<400> SEQUENCE: 69

Gln Leu Leu Ser Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile
        35                  40

<210> SEQ ID NO 70
<211> LENGTH: 41
<212> TYPE: PRT
<213> ORGANISM: Artificial Sequence
<220> FEATURE:
<223> OTHER INFORMATION: Human TCAP1 (41 a.a.)

<400> SEQUENCE: 70

Gln Gln Leu Leu Ser Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile
        35                  40

<210> SEQ ID NO 71
<211> LENGTH: 43
<212> TYPE: PRT
<213> ORGANISM: Artificial Sequence
<220> FEATURE:
<223> OTHER INFORMATION: Human preTCAP1 (43 a.a.)

<400> SEQUENCE: 71

Gln Leu Leu Ser Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile Gly Arg Arg
        35                  40

<210> SEQ ID NO 72
<211> LENGTH: 44
<212> TYPE: PRT
<213> ORGANISM: Artificial Sequence
<220> FEATURE:
<223> OTHER INFORMATION: Human preTCAP1 (44 a.a.)

<400> SEQUENCE: 72

Gln Gln Leu Leu Ser Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile Gly Arg Arg
        35                  40

<210> SEQ ID NO 73
<211> LENGTH: 120
<212> TYPE: DNA
<213> ORGANISM: Artificial Sequence
```

<220> FEATURE:
<223> OTHER INFORMATION: Human TCAP1 (120 n.a.)

<400> SEQUENCE: 73
cagcttttga gcactgggcg ggtacaaggt tacgatgggt attttgtttt gtctgttgag    60
cagtatttag aactttctga cagtgccaat aatattcact ttatgagaca gagcgaaata   120

<210> SEQ ID NO 74
<211> LENGTH: 123
<212> TYPE: DNA
<213> ORGANISM: Artificial Sequence
<220> FEATURE:
<223> OTHER INFORMATION: Human TCAP1 (123 n.a.)

<400> SEQUENCE: 74
cagcagcttt tgagcactgg gcgggtacaa ggttacgatg gtattttgt tttgtctgtt     60 gagcagtatt tagaactttc tgacagtgcc aataatattc actttatgag acagagcgaa  120
ata                                                                123

<210> SEQ ID NO 75
<211> LENGTH: 129
<212> TYPE: DNA
<213> ORGANISM: Artificial Sequence
<220> FEATURE:
<223> OTHER INFORMATION: Human preTCAP1 (129 n.a.)

<400> SEQUENCE: 75
cagcttttga gcactgggcg ggtacaaggt tacgatgggt attttgtttt gtctgttgag    60
cagtatttag aactttctga cagtgccaat aatattcact ttatgagaca gagcgaaata   120
ggcaggagg                                                          129

<210> SEQ ID NO 76
<211> LENGTH: 132
<212> TYPE: DNA
<213> ORGANISM: Artificial Sequence
<220> FEATURE:
<223> OTHER INFORMATION: Human preTCAP1 (132 n.a.)

<400> SEQUENCE: 76
cagcagcttt tgagcactgg gcgggtacaa ggttacgatg gtattttgt tttgtctgtt     60 gagcagtatt tagaactttc tgacagtgcc aataatattc actttatgag acagagcgaa  120
ataggcagga gg                                                      132

<210> SEQ ID NO 77
<211> LENGTH: 40
<212> TYPE: PRT
<213> ORGANISM: Artificial Sequence
<220> FEATURE:
<223> OTHER INFORMATION: Human TCAP2 (40 a.a.)

<400> SEQUENCE: 77

Gln Leu Leu Ser Thr Gly Arg Val Gln Gly Tyr Glu Gly Tyr Tyr Val
1               5                   10                  15

Leu Pro Val Glu Gln Tyr Pro Glu Leu Ala Asp Ser Ser Ser Asn Ile
            20                  25                  30

Gln Phe Leu Arg Gln Asn Glu Met
        35                  40

<210> SEQ ID NO 78
<211> LENGTH: 41

<212> TYPE: PRT
<213> ORGANISM: Artificial Sequence
<220> FEATURE:
<223> OTHER INFORMATION: Human preTCAP2 (41 a.a.)

<400> SEQUENCE: 78

Gln Gln Leu Leu Ser Thr Gly Arg Val Gln Gly Tyr Glu Gly Tyr Tyr
1               5                   10                  15

Val Leu Pro Val Glu Gln Tyr Pro Glu Leu Ala Asp Ser Ser Ser Asn
            20                  25                  30

Ile Gln Phe Leu Arg Gln Asn Glu Met
        35                  40

<210> SEQ ID NO 79
<211> LENGTH: 43
<212> TYPE: PRT
<213> ORGANISM: Artificial Sequence
<220> FEATURE:
<223> OTHER INFORMATION: Human preTCAP2 (43 a.a.)

<400> SEQUENCE: 79

Gln Leu Leu Ser Thr Gly Arg Val Gln Gly Tyr Glu Gly Tyr Tyr Val
1               5                   10                  15

Leu Pro Val Glu Gln Tyr Pro Glu Leu Ala Asp Ser Ser Ser Asn Ile
            20                  25                  30

Gln Phe Leu Arg Gln Asn Glu Met Gly Lys Arg
        35                  40

<210> SEQ ID NO 80
<211> LENGTH: 44
<212> TYPE: PRT
<213> ORGANISM: Artificial Sequence
<220> FEATURE:
<223> OTHER INFORMATION: Human preTCAP2 (44 a.a.)

<400> SEQUENCE: 80

Gln Gln Leu Leu Ser Thr Gly Arg Val Gln Gly Tyr Glu Gly Tyr Tyr
1               5                   10                  15

Val Leu Pro Val Glu Gln Tyr Pro Glu Leu Ala Asp Ser Ser Ser Asn
            20                  25                  30

Ile Gln Phe Leu Arg Gln Asn Glu Met Gly Lys Arg
        35                  40

<210> SEQ ID NO 81
<211> LENGTH: 120
<212> TYPE: DNA
<213> ORGANISM: Artificial Sequence
<220> FEATURE:
<223> OTHER INFORMATION: Human TCAP2 (120 n.a.)

<400> SEQUENCE: 81
cagcttctga gcaccgggcg cgtgcaaggg tacgagggat attacgtgct tcccgtggag      60
caatacccag agcttgcaga cagtagcagc aacatccagt ttttaagaca gaatgagatg     120

<210> SEQ ID NO 82
<211> LENGTH: 123
<212> TYPE: DNA
<213> ORGANISM: Artificial Sequence
<220> FEATURE:
<223> OTHER INFORMATION: Human TCAP2 (123 n.a.)

<400> SEQUENCE: 82
cagcagcttc tgagcaccgg gcgcgtgcaa gggtacgagg gatattacgt gcttcccgtg      60

```
gagcaatacc cagagcttgc agacagtagc agcaacatcc agttttaag acagaatgag    120 atg                                                                 123

<210> SEQ ID NO 83
<211> LENGTH: 129
<212> TYPE: DNA
<213> ORGANISM: Artificial Sequence
<220> FEATURE:
<223> OTHER INFORMATION: Human preTCAP2 (129 n.a.)

<400> SEQUENCE: 83
cagcttctga gcaccgggcg cgtgcaaggg tacgagggat attacgtgct tcccgtggag    60
caatacccag agcttgcaga cagtagcagc aacatccagt ttttaagaca gaatgagatg   120
ggaaagagg                                                           129

<210> SEQ ID NO 84
<211> LENGTH: 132
<212> TYPE: DNA
<213> ORGANISM: Artificial Sequence
<220> FEATURE:
<223> OTHER INFORMATION: Human preTCAP2 (132 n.a.)

<400> SEQUENCE: 84
cagcagcttc tgagcaccgg gcgcgtgcaa gggtacgagg gatattacgt gcttcccgtg    60
gagcaatacc cagagcttgc agacagtagc agcaacatcc agttttaag acagaatgag   120 atgggaaaga gg                                                       132

<210> SEQ ID NO 85
<211> LENGTH: 40
<212> TYPE: PRT
<213> ORGANISM: Artificial Sequence
<220> FEATURE:
<223> OTHER INFORMATION: Human TCAP3 (40 a.a.)

<400> SEQUENCE: 85

Gln Leu Leu Ser Ala Gly Lys Val Gln Gly Tyr Asp Gly Tyr Tyr Val
1               5                   10                  15

Leu Ser Val Glu Gln Tyr Pro Glu Leu Ala Asp Ser Ala Asn Asn Ile
            20                  25                  30

Gln Phe Leu Arg Gln Ser Glu Ile
        35                  40

<210> SEQ ID NO 86
<211> LENGTH: 41
<212> TYPE: PRT
<213> ORGANISM: Artificial Sequence
<220> FEATURE:
<223> OTHER INFORMATION: Human TCAP3 (41 a.a.)

<400> SEQUENCE: 86

Arg Gln Leu Leu Ser Ala Gly Lys Val Gln Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Ile Gln Phe Leu Arg Gln Ser Glu Ile
        35                  40

<210> SEQ ID NO 87
<211> LENGTH: 43
<212> TYPE: PRT
```

<213> ORGANISM: Artificial Sequence
<220> FEATURE:
<223> OTHER INFORMATION: Human preTCAP3 (43 a.a.)

<400> SEQUENCE: 87

```
Gln Leu Leu Ser Ala Gly Lys Val Gln Gly Tyr Asp Gly Tyr Tyr Val
1               5                   10                  15

Leu Ser Val Glu Gln Tyr Pro Glu Leu Ala Asp Ser Ala Asn Asn Ile
            20                  25                  30

Gln Phe Leu Arg Gln Ser Glu Ile Gly Arg Arg
        35                  40
```

<210> SEQ ID NO 88
<211> LENGTH: 44
<212> TYPE: PRT
<213> ORGANISM: Artificial Sequence
<220> FEATURE:
<223> OTHER INFORMATION: Human preTCAP3 (44 a.a.)

<400> SEQUENCE: 88

```
Arg Gln Leu Leu Ser Ala Gly Lys Val Gln Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Ile Gln Phe Leu Arg Gln Ser Glu Ile Gly Arg Arg
        35                  40
```

<210> SEQ ID NO 89
<211> LENGTH: 120
<212> TYPE: DNA
<213> ORGANISM: Artificial Sequence
<220> FEATURE:
<223> OTHER INFORMATION: Human TCAP3 (120 n.a.)

<400> SEQUENCE: 89

```
cagctgctga gcgccggcaa ggtgcagggc tacgacgggt actacgtact ctcggtggag      60
cagtaccccg agctggccga cagcgccaac aacatccagt tcctgcggca gagcgagatc     120
```

<210> SEQ ID NO 90
<211> LENGTH: 123
<212> TYPE: DNA
<213> ORGANISM: Artificial Sequence
<220> FEATURE:
<223> OTHER INFORMATION: Human TCAP3 (123 n.a.)

<400> SEQUENCE: 90

```
cggcagctgc tgagcgccgg caaggtgcag ggctacgacg gtactacgt actctcggtg       60 gagcagtacc ccgagctggc cgacagcgcc aacaacatcc agttcctgcg cagagcgag     120 atc                                                                   123
```

<210> SEQ ID NO 91
<211> LENGTH: 129
<212> TYPE: DNA
<213> ORGANISM: Artificial Sequence
<220> FEATURE:
<223> OTHER INFORMATION: Human preTCAP (129 n.a.)

<400> SEQUENCE: 91

```
cagctgctga gcgccggcaa ggtgcagggc tacgacgggt actacgtact ctcggtggag      60
cagtaccccg agctggccga cagcgccaac aacatccagt tcctgcggca gagcgagatc     120
ggcaggagg                                                             129
```

<210> SEQ ID NO 92
<211> LENGTH: 132
<212> TYPE: DNA
<213> ORGANISM: Artificial Sequence
<220> FEATURE:
<223> OTHER INFORMATION: Human preTCAP3 (132 n.a.)

<400> SEQUENCE: 92

```
cggcagctgc tgagcgccgg caaggtgcag ggctacgacg ggtactacgt actctcggtg      60
gagcagtacc ccgagctggc cgacagcgcc aacaacatcc agttcctgcg gcagagcgag     120
atcggcagga gg                                                         132
```

<210> SEQ ID NO 93
<211> LENGTH: 40
<212> TYPE: PRT
<213> ORGANISM: Artificial Sequence
<220> FEATURE:
<223> OTHER INFORMATION: Human TCAP4 (40 a.a.)

<400> SEQUENCE: 93

```
Gln Val Leu Ser Thr Gly Arg Val Gln Gly Tyr Asp Gly Phe Phe Val
1               5                   10                  15

Ile Ser Val Glu Gln Tyr Pro Glu Leu Ser Asp Ser Ala Asn Asn Ile
            20                  25                  30

His Phe Met Arg Gln Ser Glu Met
        35                  40
```

<210> SEQ ID NO 94
<211> LENGTH: 41
<212> TYPE: PRT
<213> ORGANISM: Artificial Sequence
<220> FEATURE:
<223> OTHER INFORMATION: Human TCAP4 (41 a.a.)

<400> SEQUENCE: 94

```
Gln Gln Val Leu Ser Thr Gly Arg Val Gln Gly Tyr Asp Gly Phe Phe
1               5                   10                  15

Val Ile Ser Val Glu Gln Tyr Pro Glu Leu Ser Asp Ser Ala Asn Asn
            20                  25                  30

Ile His Phe Met Arg Gln Ser Glu Met
        35                  40
```

<210> SEQ ID NO 95
<211> LENGTH: 43
<212> TYPE: PRT
<213> ORGANISM: Artificial Sequence
<220> FEATURE:
<223> OTHER INFORMATION: Human preTCAP4 (43 a..a)

<400> SEQUENCE: 95

```
Gln Val Leu Ser Thr Gly Arg Val Gln Gly Tyr Asp Gly Phe Phe Val
1               5                   10                  15

Ile Ser Val Glu Gln Tyr Pro Glu Leu Ser Asp Ser Ala Asn Asn Ile
            20                  25                  30

His Phe Met Arg Gln Ser Glu Met Gly Arg Arg
        35                  40
```

<210> SEQ ID NO 96
<211> LENGTH: 44
<212> TYPE: PRT
<213> ORGANISM: Artificial Sequence
<220> FEATURE:
<223> OTHER INFORMATION: Human preTCAP4 (44 a.a.)

<400> SEQUENCE: 96

Gln Gln Val Leu Ser Thr Gly Arg Val Gln Gly Tyr Asp Gly Phe Phe
1               5                   10                  15

Val Ile Ser Val Glu Gln Tyr Pro Glu Leu Ser Asp Ser Ala Asn Asn
            20                  25                  30

Ile His Phe Met Arg Gln Ser Glu Met Gly Arg Arg
        35                  40

<210> SEQ ID NO 97
<211> LENGTH: 120
<212> TYPE: DNA
<213> ORGANISM: Artificial Sequence
<220> FEATURE:
<223> OTHER INFORMATION: Human TCAP4 (120 n.a.)

<400> SEQUENCE: 97
caggtgctga gcacagggcg ggtgcaaggc tacgacggct ttttcgtgat ctctgtcgag      60
cagtacccag aactgtcaga cagcgccaac aacatccact tcatgagaca gagcgagatg     120

<210> SEQ ID NO 98
<211> LENGTH: 123
<212> TYPE: DNA
<213> ORGANISM: Artificial Sequence
<220> FEATURE:
<223> OTHER INFORMATION: Human TCAP4 (123 n.a.)

<400> SEQUENCE: 98
cagcaggtgc tgagcacagg gcgggtgcaa ggctacgacg gcttttcgt gatctctgtc      60 gagcagtacc cagaactgtc agacagcgcc aacaacatcc acttcatgag acagagcgag    120
atg                                                                  123

<210> SEQ ID NO 99
<211> LENGTH: 129
<212> TYPE: DNA
<213> ORGANISM: Artificial Sequence
<220> FEATURE:
<223> OTHER INFORMATION: Human preTCAP4 (129 n.a.)

<400> SEQUENCE: 99
caggtgctga gcacagggcg ggtgcaaggc tacgacggct ttttcgtgat ctctgtcgag      60
cagtacccag aactgtcaga cagcgccaac aacatccact tcatgagaca gagcgagatg     120
ggccggagg                                                            129

<210> SEQ ID NO 100
<211> LENGTH: 132
<212> TYPE: DNA
<213> ORGANISM: Artificial Sequence
<220> FEATURE:
<223> OTHER INFORMATION: Human preTCAP4 (132 n.a.)

<400> SEQUENCE: 100
cagcaggtgc tgagcacagg gcgggtgcaa ggctacgacg gcttttcgt gatctctgtc      60 gagcagtacc cagaactgtc agacagcgcc aacaacatcc acttcatgag acagagcgag    120
atgggccgga gg                                                        132

<210> SEQ ID NO 101
<211> LENGTH: 41

```
<212> TYPE: PRT
<213> ORGANISM: Artificial Sequence
<220> FEATURE:
<223> OTHER INFORMATION: G. gallus TCAP-1

<400> SEQUENCE: 101

Gln Gln Leu Leu Asn Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile
            35                  40

<210> SEQ ID NO 102
<211> LENGTH: 41
<212> TYPE: PRT
<213> ORGANISM: Artificial Sequence
<220> FEATURE:
<223> OTHER INFORMATION: Zebrafish TCAP-4

<400> SEQUENCE: 102

Gln Gln Leu Leu Ser Ser Gly Arg Val Gln Gly Tyr Glu Gly Phe Tyr
1               5                   10                  15

Ile Val Ser Val Asp Gln Phe Pro Glu Leu Thr Asp Asn Ile Asn Asn
            20                  25                  30

Val His Phe Trp Arg Gln Thr Glu Met
            35                  40

<210> SEQ ID NO 103
<211> LENGTH: 37
<212> TYPE: PRT
<213> ORGANISM: Artificial Sequence
<220> FEATURE:
<223> OTHER INFORMATION: D. melanogaster Ten-m gene product

<400> SEQUENCE: 103

Glu Leu Val Gln His Gly Asp Val Asp Gly Trp Asn Gly Asp Ile His
1               5                   10                  15

Ser Ile His Lys Tyr Pro Gln Leu Ala Asp Pro Gly Asn Val Ala Phe
            20                  25                  30

Gln Arg Asp Ala Lys
        35

<210> SEQ ID NO 104
<211> LENGTH: 41
<212> TYPE: PRT
<213> ORGANISM: Artificial Sequence
<220> FEATURE:
<223> OTHER INFORMATION: Human CRF TCAP like region

<400> SEQUENCE: 104

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
            35                  40

<210> SEQ ID NO 105
<211> LENGTH: 40
<212> TYPE: PRT
<213> ORGANISM: Artificial Sequence
<220> FEATURE:
```

<223> OTHER INFORMATION: Human urocortin TCAP-like region

<400> SEQUENCE: 105

Asp Asn Pro Ser Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 106
<211> LENGTH: 38
<212> TYPE: PRT
<213> ORGANISM: Artificial Sequence
<220> FEATURE:
<223> OTHER INFORMATION: Human urocortin 2 TCAP-like region

<400> SEQUENCE: 106

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 107
<211> LENGTH: 38
<212> TYPE: PRT
<213> ORGANISM: Artificial Sequence
<220> FEATURE:
<223> OTHER INFORMATION: Human urocortin 3 TCAP=like region

<400> SEQUENCE: 107

Phe Thr Leu Ser Leu Asp Val Pro Thr Asn Ile Met Asn Leu Leu Phe
1               5                   10                  15

Asn Ile Ala Lys Ala Lys Asn Leu Arg Ala Gln Ala Ala Ala Asn Ala
            20                  25                  30

His Leu Met Ala Gln Ile
        35

<210> SEQ ID NO 108
<211> LENGTH: 46
<212> TYPE: PRT
<213> ORGANISM: Artificial Sequence
<220> FEATURE:
<223> OTHER INFORMATION: L. migratoria DP

<400> SEQUENCE: 108

Met Gly Met Gly Pro Ser Leu Ser Ile Val Asn Pro Met Asp Val Leu
1               5                   10                  15

Arg Gln Arg Leu Leu Leu Glu Ile Ala Arg Arg Arg Leu Arg Asp Ala
            20                  25                  30

Glu Glu Gln Ile Lys Ala Asn Lys Asp Phe Leu Gln Gln Ile
        35                  40                  45

<210> SEQ ID NO 109
<211> LENGTH: 46
<212> TYPE: PRT
<213> ORGANISM: Artificial Sequence
<220> FEATURE:
<223> OTHER INFORMATION: A. domesticus DP

<400> SEQUENCE: 109

Thr Gly Ala Gln Ser Leu Ser Ile Val Ala Pro Leu Asp Val Leu Arg
1               5                   10                  15

Gln Arg Leu Met Asn Glu Leu Asn Arg Arg Met Arg Glu Leu Gln
            20                  25                  30

Gly Ser Arg Ile Gln Gln Asn Arg Gln Leu Leu Thr Ser Ile
        35                  40                  45

<210> SEQ ID NO 110
<211> LENGTH: 39
<212> TYPE: PRT
<213> ORGANISM: Artificial Sequence
<220> FEATURE:
<223> OTHER INFORMATION: T. molitor DP

<400> SEQUENCE: 110

Ser Pro Thr Ile Ser Ile Thr Ala Pro Ile Asp Val Leu Arg Lys Thr
1               5                   10                  15

Trp Glu Gln Glu Arg Ala Arg Lys Gln Met Val Ala Gln Asn Asn Arg
            20                  25                  30

Glu Phe Leu Asn Ser Leu Asn
        35

<210> SEQ ID NO 111
<211> LENGTH: 41
<212> TYPE: PRT
<213> ORGANISM: Artificial Sequence
<220> FEATURE:
<223> OTHER INFORMATION: M. sexta DP-1

<400> SEQUENCE: 111

Arg Met Pro Ser Leu Ser Ile Asp Leu Pro Met Ser Val Leu Arg Gln
1               5                   10                  15

Lys Leu Ser Leu Glu Lys Glu Arg Lys Val His Ala Leu Arg Ala Ala
            20                  25                  30

Ala Asn Arg Asn Phe Leu Asn Asp Ile
        35                  40

<210> SEQ ID NO 112
<211> LENGTH: 30
<212> TYPE: PRT
<213> ORGANISM: Artificial Sequence
<220> FEATURE:
<223> OTHER INFORMATION: M. sexta DP-II

<400> SEQUENCE: 112

Ser Leu Ser Val Asn Pro Ala Val Asp Ile Leu Gln His Arg Tyr Met
1               5                   10                  15

Glu Lys Val Ala Gln Asn Asn Arg Asn Phe Leu Asn Arg Val
            20                  25                  30

<210> SEQ ID NO 113
<211> LENGTH: 45
<212> TYPE: PRT
<213> ORGANISM: Artificial Sequence
<220> FEATURE:
<223> OTHER INFORMATION: P. Americana

<400> SEQUENCE: 113

Thr Gly Ser Gly Pro Ser Leu Ser Ile Val Asn Pro Leu Asp Val Leu
1               5                   10                  15

Arg Gln Arg Leu Leu Leu Glu Ile Ala Arg Arg Arg Met Arg Gln Ser
            20                  25                  30

Gln Asp Gln Ile Gln Asn Arg Glu Ile Leu Gln Thr Ile
        35                  40                  45

<210> SEQ ID NO 114
<211> LENGTH: 41
<212> TYPE: PRT
<213> ORGANISM: Artificial Sequence
<220> FEATURE:
<223> OTHER INFORMATION: O. keta CRP

<400> SEQUENCE: 114

Ser Asp Asp Pro Pro Ile Ser Leu Asp Leu Thr Phe His Met Leu Arg
1               5                   10                  15

Gln Met Asn Glu Met Ser Arg Ala Glu Gln Leu Gln Gln Gln Ala His
            20                  25                  30

Ser Asn Arg Lys Met Met Glu Ile Phe
        35                  40

<210> SEQ ID NO 115
<211> LENGTH: 40
<212> TYPE: PRT
<213> ORGANISM: Artificial Sequence
<220> FEATURE:
<223> OTHER INFORMATION: R. norvegicus

<400> SEQUENCE: 115

Asp Asp Pro Pro Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 116
<211> LENGTH: 37
<212> TYPE: PRT
<213> ORGANISM: Artificial Sequence
<220> FEATURE:
<223> OTHER INFORMATION: P. sauvageii

<400> SEQUENCE: 116

Gln Gly Pro Pro Ile Ser Ile Asp Leu Ser Leu Glu Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu
        35

<210> SEQ ID NO 117
<211> LENGTH: 41
<212> TYPE: PRT
<213> ORGANISM: Artificial Sequence
<220> FEATURE:
<223> OTHER INFORMATION: C. carpio US

<400> SEQUENCE: 117

Asn Asp Asp Pro Pro Ile Ser Ile Asp Leu Thr Phe His Leu Leu Arg
1               5                   10                  15

Asn Met Ile Glu Met Ala Arg Asn Glu Asn Gln Arg Glu Gln Ala Gly
            20                  25                  30

Leu Asn Arg Lys Tyr Leu Asp Glu Val
        35                  40

```
<210> SEQ ID NO 118
<211> LENGTH: 38
<212> TYPE: PRT
<213> ORGANISM: Artificial Sequence
<220> FEATURE:
<223> OTHER INFORMATION: M. Musculus UCN2

<400> SEQUENCE: 118

Val Ile Leu Ser Leu Asp Val Pro Ile Gly Leu Leu Arg Ile Leu Leu
1               5                   10                  15

Glu Gln Ala Arg Tyr Lys Ala Ala Arg Asn Gln Ala Ala Thr Asn Ala
            20                  25                  30

Gln Ile Leu Ala His Val
        35

<210> SEQ ID NO 119
<211> LENGTH: 38
<212> TYPE: PRT
<213> ORGANISM: Artificial Sequence
<220> FEATURE:
<223> OTHER INFORMATION: R. dano UCN2

<400> SEQUENCE: 119

Leu Thr Leu Ser Leu Asp Val Pro Thr Asn Ile Met Asn Val Leu Phe
1               5                   10                  15

Asp Val Ala Lys Ala Lys Asn Leu Arg Ala Lys Ala Ala Glu Asn Ala
            20                  25                  30

Arg Leu Leu Ala His Ile
        35

<210> SEQ ID NO 120
<211> LENGTH: 305
<212> TYPE: DNA
<213> ORGANISM: Artificial Sequence
<220> FEATURE:
<223> OTHER INFORMATION: Hamster 305bp urocortin cDNA probe examples
      "cloning mRNA"

<400> SEQUENCE: 120
attcaccgcc gctcgggatc tgagcctgca ggcgagcggc agcgacggga agaccttccg      60
ctgtccatcg acctcacatt ccacctgcta cggaccctgc tggagatggc ccggacacag     120
agccaacgcg agcgagcaga gcagaaccga atcatactca acgcggtggg caagtgatcg     180
gcccggtgtg ggaccccaaa aggctcgacc ctttccccta cctacccggg gctgaagtc     240 acgcgaccga agtcggctta gtcccgcggt gcagcgcctc ccagagttac cctgaacaat    300
cccgc                                                                305

<210> SEQ ID NO 121
<211> LENGTH: 24
<212> TYPE: DNA
<213> ORGANISM: Artificial Sequence
<220> FEATURE:
<223> OTHER INFORMATION: TCAP1 fwd primer

<400> SEQUENCE: 121
acgtcagtgt tgatgggagg acta                                            24

<210> SEQ ID NO 122
<211> LENGTH: 27
<212> TYPE: DNA
<213> ORGANISM: Artificial Sequence
```

```
<220> FEATURE:
<223> OTHER INFORMATION: TCAP1 rvs primer

<400> SEQUENCE: 122
cctcctgcct atttcactct gtctcat                                              27

<210> SEQ ID NO 123
<211> LENGTH: 25
<212> TYPE: DNA
<213> ORGANISM: Artificial Sequence
<220> FEATURE:
<223> OTHER INFORMATION: TCAP2 Fwd primer

<400> SEQUENCE: 123
tcgagggcaa ggacacacac tactt                                                25

<210> SEQ ID NO 124
<211> LENGTH: 26
<212> TYPE: DNA
<213> ORGANISM: Artificial Sequence
<220> FEATURE:
<223> OTHER INFORMATION: TCAP2 rvs primer

<400> SEQUENCE: 124
aagaactgga tgttgctgct actgtc                                               26

<210> SEQ ID NO 125
<211> LENGTH: 25
<212> TYPE: DNA
<213> ORGANISM: Artificial Sequence
<220> FEATURE:
<223> OTHER INFORMATION: TCAP3 fwd primer

<400> SEQUENCE: 125
caacaacgcc ttctacctgg agaac                                                25

<210> SEQ ID NO 126
<211> LENGTH: 21
<212> TYPE: DNA
<213> ORGANISM: Artificial Sequence
<220> FEATURE:
<223> OTHER INFORMATION: TCAP3 rvs primer

<400> SEQUENCE: 126
tgttgttggc actgtcagcc a                                                    21

<210> SEQ ID NO 127
<211> LENGTH: 23
<212> TYPE: DNA
<213> ORGANISM: Artificial Sequence
<220> FEATURE:
<223> OTHER INFORMATION: TCAP4 fwd primer

<400> SEQUENCE: 127
tttgcctcca gtggttccat ctt                                                  23

<210> SEQ ID NO 128
<211> LENGTH: 24
<212> TYPE: DNA
<213> ORGANISM: Artificial Sequence
<220> FEATURE:
<223> OTHER INFORMATION: TCAP4 rvs primer

<400> SEQUENCE: 128
tggatattgt tggcgctgtc tgac                                                 24
```

```
<210> SEQ ID NO 129
<211> LENGTH: 6
<212> TYPE: PRT
<213> ORGANISM: Artificial Sequence
<220> FEATURE:
<223> OTHER INFORMATION: Conserved motif between CRF and TCAP I/L S X X
      (X)-L/V at amino terminus
<220> FEATURE:
<221> NAME/KEY: MISC_FEATURE
<222> LOCATION: (1)..(1)
<223> OTHER INFORMATION: X=I or L
<220> FEATURE:
<221> NAME/KEY: MISC_FEATURE
<222> LOCATION: (3)..(3)
<223> OTHER INFORMATION: X=T or A
<220> FEATURE:
<221> NAME/KEY: MISC_FEATURE
<222> LOCATION: (4)..(4)
<223> OTHER INFORMATION: X=L, I or G
<220> FEATURE:
<221> NAME/KEY: MISC_FEATURE
<222> LOCATION: (5)..(5)
<223> OTHER INFORMATION: X=D, R or K
<220> FEATURE:
<221> NAME/KEY: MISC_FEATURE
<222> LOCATION: (6)..(6)
<223> OTHER INFORMATION: X=L or V

<400> SEQUENCE: 129

Xaa Ser Xaa Xaa Xaa Xaa
1               5

<210> SEQ ID NO 130
<211> LENGTH: 4
<212> TYPE: PRT
<213> ORGANISM: Artificial Sequence
<220> FEATURE:
<223> OTHER INFORMATION: Conserved motif between CRF and TCAP - In
      middle L/V-L/I-X-V/aliphatic residue
<220> FEATURE:
<221> NAME/KEY: MISC_FEATURE
<222> LOCATION: (1)..(1)
<223> OTHER INFORMATION: X=V or L
<220> FEATURE:
<221> NAME/KEY: MISC_FEATURE
<222> LOCATION: (4)..(4)
<223> OTHER INFORMATION: X=M, L Q, I or V
<220> FEATURE:
<221> NAME/KEY: MISC_FEATURE
<222> LOCATION: (2)..(2)
<223> OTHER INFORMATION: X=L, I or F
<220> FEATURE:
<221> NAME/KEY: MISC_FEATURE
<222> LOCATION: (3)..(3)
<223> OTHER INFORMATION: X=E, N, S or P

<400> SEQUENCE: 130

Xaa Xaa Xaa Xaa
1

<210> SEQ ID NO 131
<211> LENGTH: 4
<212> TYPE: PRT
<213> ORGANISM: Artificial Sequence
<220> FEATURE:
<223> OTHER INFORMATION: Conserved motif between CRF and TCAP
      N/I/A-H/basic residue -I/L/F/-aliphatic at carboxy terminus
<220> FEATURE:
<221> NAME/KEY: MISC_FEATURE
<222> LOCATION: (2)..(2)
<223> OTHER INFORMATION: X=R, A or I
<220> FEATURE:
<221> NAME/KEY: MISC_FEATURE
<222> LOCATION: (3)..(3)
```

```
<223> OTHER INFORMATION: X=H or basic residues, K, I, R or Q
<220> FEATURE:
<221> NAME/KEY: MISC_FEATURE
<222> LOCATION: (4)..(4)
<223> OTHER INFORMATION: X=I, L or F

<400> SEQUENCE: 131

Asn Xaa Xaa Xaa
 1

<210> SEQ ID NO 132
<211> LENGTH: 8964
<212> TYPE: DNA
<213> ORGANISM: Mus musculus
<220> FEATURE:
<221> NAME/KEY: exon
<222> LOCATION: (50)..(8197)
<223> OTHER INFORMATION:

<400> SEQUENCE: 132
```

| | | |
|---|---|---|
| aagttctaag aagccggacc gatgtgcaca gagaaggaat gaaggaagt atg gat gtg<br>                                                                    Met Asp Val<br>                                                                     1 | | 58 |
| aag gaa cgc agg cct tac tgc tcc ttg acc aag agc aga cgg gaa aag<br>Lys Glu Arg Arg Pro Tyr Cys Ser Leu Thr Lys Ser Arg Arg Glu Lys<br>  5                  10                  15 | | 106 |
| gaa agg cgc tat aca aat tcg tcc gcg gac aat gag gag tgt agg gtc<br>Glu Arg Arg Tyr Thr Asn Ser Ser Ala Asp Asn Glu Glu Cys Arg Val<br>20                  25                  30                  35 | | 154 |
| ccc acg cag aag tcc tat agt tcc agt gaa acc ttg aaa gct ttc gat<br>Pro Thr Gln Lys Ser Tyr Ser Ser Ser Glu Thr Leu Lys Ala Phe Asp<br>                 40                  45                  50 | | 202 |
| cat gat tat tca cgg ctg ctt tat gga aac aga gta aag gat ttg gtc<br>His Asp Tyr Ser Arg Leu Leu Tyr Gly Asn Arg Val Lys Asp Leu Val<br>             55                  60                  65 | | 250 |
| cac aga gaa gcc gac gag tat act aga caa gga cag aat ttt acc cta<br>His Arg Glu Ala Asp Glu Tyr Thr Arg Gln Gly Gln Asn Phe Thr Leu<br>         70                  75                  80 | | 298 |
| agg cag tta gga gtg tgt gaa tcc gca act cga aga gga gtg gca ttc<br>Arg Gln Leu Gly Val Cys Glu Ser Ala Thr Arg Arg Gly Val Ala Phe<br>     85                  90                  95 | | 346 |
| tgt gcg gaa atg ggg ctc cct cac aga ggt tac tcc atc agt gca ggg<br>Cys Ala Glu Met Gly Leu Pro His Arg Gly Tyr Ser Ile Ser Ala Gly<br>100                 105                 110                 115 | | 394 |
| tca gat gcg gat acg gaa aac gaa gca gtg atg tcc cct gag cat gcc<br>Ser Asp Ala Asp Thr Glu Asn Glu Ala Val Met Ser Pro Glu His Ala<br>                120                 125                 130 | | 442 |
| atg aga ctt tgg ggc agg ggg gtc aaa tcg ggc cgc agt tcc tgc ctg<br>Met Arg Leu Trp Gly Arg Gly Val Lys Ser Gly Arg Ser Ser Cys Leu<br>            135                 140                 145 | | 490 |
| tca agc cgg tcc aac tcc gcc ctc acc ctg aca gac acg gag cac gag<br>Ser Ser Arg Ser Asn Ser Ala Leu Thr Leu Thr Asp Thr Glu His Glu<br>        150                 155                 160 | | 538 |
| aac agg tcg gac agt gag agc gag caa cct tca aac aac cca ggg caa<br>Asn Arg Ser Asp Ser Glu Ser Glu Gln Pro Ser Asn Asn Pro Gly Gln<br>    165                 170                 175 | | 586 |
| ccc acc ctg cag cct ttg ccg cca tcc cac aag cag cac ccg gcg cag<br>Pro Thr Leu Gln Pro Leu Pro Pro Ser His Lys Gln His Pro Ala Gln<br>180                 185                 190                 195 | | 634 |
| cat cac ccg tcc atc act tcc ctc aat aga aac tcc ctg acc aat aga<br>His His Pro Ser Ile Thr Ser Leu Asn Arg Asn Ser Leu Thr Asn Arg<br>                200                 205                 210 | | 682 |

-continued

| | |
|---|---|
| agg aac cag agt ccg gcc ccg ccg gct gct ttg ccc gcc gag ctg caa<br>Arg Asn Gln Ser Pro Ala Pro Pro Ala Ala Leu Pro Ala Glu Leu Gln<br>215               220                   225 | 730 |
| acc aca ccc gag tcc gtc cag ctg cag gac agc tgg gtc ctt ggc agt<br>Thr Thr Pro Glu Ser Val Gln Leu Gln Asp Ser Trp Val Leu Gly Ser<br>     230                 235                   240 | 778 |
| aat gta cca ctg gaa agc agg cat ttc cta ttc aaa aca ggg aca ggg<br>Asn Val Pro Leu Glu Ser Arg His Phe Leu Phe Lys Thr Gly Thr Gly<br>245                 250                   255 | 826 |
| acg acg cca ctg ttc agt acg gca acc ccg gga tac aca atg gca tct<br>Thr Thr Pro Leu Phe Ser Thr Ala Thr Pro Gly Tyr Thr Met Ala Ser<br>260                 265                   270                   275 | 874 |
| ggc tct gtt tat tct ccg cct acc cgg cca ctt cct aga aac acc cta<br>Gly Ser Val Tyr Ser Pro Pro Thr Arg Pro Leu Pro Arg Asn Thr Leu<br>                 280                 285                   290 | 922 |
| tca aga agt gct ttt aaa ttc aag aag tct tca aag tac tgc agc tgg<br>Ser Arg Ser Ala Phe Lys Phe Lys Lys Ser Ser Lys Tyr Cys Ser Trp<br>                 295                 300                   305 | 970 |
| agg tgc acc gca ctg tgt gct gta ggg gtc tca gtg ctc ctg gcc att<br>Arg Cys Thr Ala Leu Cys Ala Val Gly Val Ser Val Leu Leu Ala Ile<br>                 310                 315                   320 | 1018 |
| ctc ctc tcc tat ttt ata gca atg cat cta ttt ggc ctc aac tgg cac<br>Leu Leu Ser Tyr Phe Ile Ala Met His Leu Phe Gly Leu Asn Trp His<br>325                 330                   335 | 1066 |
| tta cag cag acg gaa aat gac aca ttc gag aat gga aaa gtg aat tct<br>Leu Gln Gln Thr Glu Asn Asp Thr Phe Glu Asn Gly Lys Val Asn Ser<br>340                 345                   350                   355 | 1114 |
| gac acc gtg cca aca aac act gta tcg tta cct tct ggc gac aat gga<br>Asp Thr Val Pro Thr Asn Thr Val Ser Leu Pro Ser Gly Asp Asn Gly<br>                 360                 365                   370 | 1162 |
| aaa tta ggt gga ttt aca cat gaa aat aac acc ata gat tcc gga gaa<br>Lys Leu Gly Gly Phe Thr His Glu Asn Asn Thr Ile Asp Ser Gly Glu<br>                 375                 380                   385 | 1210 |
| ctt gat att ggc cgg aga gca att caa gag gtt ccc ccc ggg atc ttc<br>Leu Asp Ile Gly Arg Arg Ala Ile Gln Glu Val Pro Pro Gly Ile Phe<br>                 390                 395                   400 | 1258 |
| tgg aga tcg cag ctc ttt att gat cag cca cag ttt ctt aag ttc aac<br>Trp Arg Ser Gln Leu Phe Ile Asp Gln Pro Gln Phe Leu Lys Phe Asn<br>405                 410                   415 | 1306 |
| atc tct ctt cag aag gat gca ttg atc gga gtg tac ggc cgg aag ggc<br>Ile Ser Leu Gln Lys Asp Ala Leu Ile Gly Val Tyr Gly Arg Lys Gly<br>420                 425                   430                   435 | 1354 |
| tta ccg cct tcc cat act cag tac gac ttt gtg gaa cta ctg gat ggt<br>Leu Pro Pro Ser His Thr Gln Tyr Asp Phe Val Glu Leu Leu Asp Gly<br>                 440                 445                   450 | 1402 |
| agc agg tta att gcg aga gag cag cgg aac ctg gtg gag tcc gaa aga<br>Ser Arg Leu Ile Ala Arg Glu Gln Arg Asn Leu Val Glu Ser Glu Arg<br>                 455                 460                   465 | 1450 |
| gcc ggg cgg cag gcg aga tct gtc agc ctg cac gaa gct ggc ttc atc<br>Ala Gly Arg Gln Ala Arg Ser Val Ser Leu His Glu Ala Gly Phe Ile<br>                 470                 475                   480 | 1498 |
| cag tac ttg gat tct gga atc tgg cat ctg gct ttt tat aac gac ggg<br>Gln Tyr Leu Asp Ser Gly Ile Trp His Leu Ala Phe Tyr Asn Asp Gly<br>485                 490                   495 | 1546 |
| aaa aac cca gag cag gtc tcc ttt aac acg atc gtt ata gag tct gtg<br>Lys Asn Pro Glu Gln Val Ser Phe Asn Thr Ile Val Ile Glu Ser Val<br>500                 505                   510                   515 | 1594 |
| gtg gaa tgc ccc cga aat tgc cat gga aat gga gag tgt gtt tct gga<br>Val Glu Cys Pro Arg Asn Cys His Gly Asn Gly Glu Cys Val Ser Gly<br>                 520                 525                   530 | 1642 |

```
act tgc cat tgt ttc ccc ggg ttt cta ggt ccg gat tgt tca aga gca      1690
Thr Cys His Cys Phe Pro Gly Phe Leu Gly Pro Asp Cys Ser Arg Ala
            535                 540                 545 gcc tgt ccg gtg ctc tgt agt ggc aac ggg caa tac tcc aag ggc cgc      1738
Ala Cys Pro Val Leu Cys Ser Gly Asn Gly Gln Tyr Ser Lys Gly Arg
        550                 555                 560 tgc ctg tgc ttc agt ggc tgg aag ggc acc gag tgt gac gtg ccg acg      1786
Cys Leu Cys Phe Ser Gly Trp Lys Gly Thr Glu Cys Asp Val Pro Thr
    565                 570                 575 acc cag tgc att gac ccg cag tgc ggg ggt cgt ggg att tgc atc atg      1834
Thr Gln Cys Ile Asp Pro Gln Cys Gly Gly Arg Gly Ile Cys Ile Met
580                 585                 590                 595 ggc tct tgc gct tgt aac tcg gga tac aaa gga gaa aac tgt gag gaa      1882
Gly Ser Cys Ala Cys Asn Ser Gly Tyr Lys Gly Glu Asn Cys Glu Glu
                600                 605                 610 gcg gac tgt cta gac cct gga tgt tct aat cac ggg gtg tgt atc cat      1930
Ala Asp Cys Leu Asp Pro Gly Cys Ser Asn His Gly Val Cys Ile His
            615                 620                 625 ggg gaa tgt cac tgc aat cca ggc tgg ggt ggc agc aac tgt gaa ata      1978
Gly Glu Cys His Cys Asn Pro Gly Trp Gly Gly Ser Asn Cys Glu Ile
        630                 635                 640 ctg aag act atg tgt gca gac cag tgc tca ggc cac ggg act tac ctt      2026
Leu Lys Thr Met Cys Ala Asp Gln Cys Ser Gly His Gly Thr Tyr Leu
    645                 650                 655 caa gaa agc ggc tcc tgc act tgc gac cca aat tgg act ggc ccc gac      2074
Gln Glu Ser Gly Ser Cys Thr Cys Asp Pro Asn Trp Thr Gly Pro Asp
660                 665                 670                 675 tgc tca aat gaa ata tgt tca gtg gac tgc ggc tca cac ggc gtc tgc      2122
Cys Ser Asn Glu Ile Cys Ser Val Asp Cys Gly Ser His Gly Val Cys
                680                 685                 690 atg ggg ggc tcc tgt cgc tgt gaa gaa ggc tgg acc ggc ccg gcg tgt      2170
Met Gly Gly Ser Cys Arg Cys Glu Glu Gly Trp Thr Gly Pro Ala Cys
            695                 700                 705 aat cag aga gct tgc cac cct cgc tgt gct gag cac ggg acg tgc aag      2218
Asn Gln Arg Ala Cys His Pro Arg Cys Ala Glu His Gly Thr Cys Lys
        710                 715                 720 gac ggc aag tgc gag tgc agc caa gga tgg aac gga gag cac tgc aca      2266
Asp Gly Lys Cys Glu Cys Ser Gln Gly Trp Asn Gly Glu His Cys Thr
    725                 730                 735 att gct cac tat ttg gat aag ata gtt aaa gag ggt tgc ccc ggc ttg      2314
Ile Ala His Tyr Leu Asp Lys Ile Val Lys Glu Gly Cys Pro Gly Leu
740                 745                 750                 755 tgc aac agc aat ggg aga tgc aca ctg gac caa aac ggc tgg cac tgc      2362
Cys Asn Ser Asn Gly Arg Cys Thr Leu Asp Gln Asn Gly Trp His Cys
                760                 765                 770 gtt tgc cag cca ggg tgg aga gga gca ggc tgt gac gta gcc atg gag      2410
Val Cys Gln Pro Gly Trp Arg Gly Ala Gly Cys Asp Val Ala Met Glu
            775                 780                 785 acc ctc tgt aca gac agc aaa gac aac gaa gga gac gga ctc att gac      2458
Thr Leu Cys Thr Asp Ser Lys Asp Asn Glu Gly Asp Gly Leu Ile Asp
        790                 795                 800 tgc atg gat cct gat tgc tgc ctc cag agc tcc tgc caa aac cag ccc      2506
Cys Met Asp Pro Asp Cys Cys Leu Gln Ser Ser Cys Gln Asn Gln Pro
    805                 810                 815 tac tgt cgt ggc ttg cct gat cct cag gat atc att agc caa agc ctt      2554
Tyr Cys Arg Gly Leu Pro Asp Pro Gln Asp Ile Ile Ser Gln Ser Leu
820                 825                 830                 835 cag aca cca tct cag caa gct gcc aag tcc ttc tat gac cga atc agt      2602
Gln Thr Pro Ser Gln Gln Ala Ala Lys Ser Phe Tyr Asp Arg Ile Ser
```

```
                     840                 845                 850
ttc ctg att gga tcg gat agc acc cac gtg ctc cct gga gaa agt ccg       2650
Phe Leu Ile Gly Ser Asp Ser Thr His Val Leu Pro Gly Glu Ser Pro
            855                 860                 865 ttc aat aag agt ctt gcg tcc gtc atc aga ggc caa gta cta aca gct       2698
Phe Asn Lys Ser Leu Ala Ser Val Ile Arg Gly Gln Val Leu Thr Ala
            870                 875                 880 gat gga acc cca ctt att ggc gtc aac gtg tcg ttt tta cac tac tcg       2746
Asp Gly Thr Pro Leu Ile Gly Val Asn Val Ser Phe Leu His Tyr Ser
885                 890                 895 gaa tat gga tat acc att acc cgc cag gat gga atg ttt gac ttg gtg       2794
Glu Tyr Gly Tyr Thr Ile Thr Arg Gln Asp Gly Met Phe Asp Leu Val
900                 905                 910                 915 gca aat ggt ggc gct tct ctg act ttg gta ttt gag cgt tcc cca ttc       2842
Ala Asn Gly Gly Ala Ser Leu Thr Leu Val Phe Glu Arg Ser Pro Phe
                920                 925                 930 ctc act cag tac cac act gtg tgg att ccc tgg aat gtc ttt tat gtg       2890
Leu Thr Gln Tyr His Thr Val Trp Ile Pro Trp Asn Val Phe Tyr Val
            935                 940                 945 atg gat acc ctt gtc atg aag aaa gag gag aac gac att ccc agc tgt       2938
Met Asp Thr Leu Val Met Lys Lys Glu Glu Asn Asp Ile Pro Ser Cys
            950                 955                 960 gac ctc agt ggc ttt gtg agg cca agt ccc atc att gtg tct tca ccg       2986
Asp Leu Ser Gly Phe Val Arg Pro Ser Pro Ile Ile Val Ser Ser Pro
965                 970                 975 tta tcc acc ttc ttc agg tct tcc cct gag gac agc ccc atc atc ccc       3034
Leu Ser Thr Phe Phe Arg Ser Ser Pro Glu Asp Ser Pro Ile Ile Pro
980                 985                 990                 995 gag aca cag gtc ctg cat gaa gaa acc aca att cca gga aca gat           3079
Glu Thr Gln Val Leu His Glu Glu Thr Thr Ile Pro Gly Thr Asp
                1000                1005                1010 ttg aaa ctt tcc tac ctg agt tcc aga gcg gca ggg tac aag tca           3124
Leu Lys Leu Ser Tyr Leu Ser Ser Arg Ala Ala Gly Tyr Lys Ser
            1015                1020                1025 gtt ctt aag att acc atg acc cag gcc gtc ata ccg ttt aac ctc           3169
Val Leu Lys Ile Thr Met Thr Gln Ala Val Ile Pro Phe Asn Leu
            1030                1035                1040 atg aag gtc cat ctg atg gtg gcc gtg gtt ggg aga ctc ttc cag           3214
Met Lys Val His Leu Met Val Ala Val Val Gly Arg Leu Phe Gln
            1045                1050                1055 aag tgg ttt cct gcc tcg cca aac ttg gcc tac acg ttc atc tgg           3259
Lys Trp Phe Pro Ala Ser Pro Asn Leu Ala Tyr Thr Phe Ile Trp
            1060                1065                1070 gat aag acg gac gca tat aat cag aaa gtc tac ggc ttg tca gag           3304
Asp Lys Thr Asp Ala Tyr Asn Gln Lys Val Tyr Gly Leu Ser Glu
            1075                1080                1085 gca gtt gtg tcc gtc gga tac gag tac gag tcg tgc ttg gac ctg           3349
Ala Val Val Ser Val Gly Tyr Glu Tyr Glu Ser Cys Leu Asp Leu
            1090                1095                1100 act ctc tgg gaa aag agg act gcc gtt ttg caa ggc tat gag ttg           3394
Thr Leu Trp Glu Lys Arg Thr Ala Val Leu Gln Gly Tyr Glu Leu
            1105                1110                1115 gat gct tcg aac atg ggc ggc tgg acg ttg gac aag cac cat gta           3439
Asp Ala Ser Asn Met Gly Gly Trp Thr Leu Asp Lys His His Val
            1120                1125                1130 ctg gac gtt cag aac ggt ata cta tac aaa gga aat gga gaa aat           3484
Leu Asp Val Gln Asn Gly Ile Leu Tyr Lys Gly Asn Gly Glu Asn
            1135                1140                1145 cag ttc atc tct cag cag cct ccg gtg gtc agc agc atc atg ggt           3529
```

```
      Gln Phe Ile Ser Gln  Gln Pro Val Val  Ser Ser Ile Met Gly
                      1150             1155             1160 aat ggt cgg agg cgt  agc atc tca tgc  cca agt tgc aat ggt caa    3574
Asn Gly Arg Arg Arg  Ser Ile Ser Cys  Pro Ser Cys Asn Gly Gln
                1165             1170             1175 gct gac ggg aac aaa  ctc ctg gca ccc  gtg gcg ctt gcc tgt ggg    3619
Ala Asp Gly Asn Lys  Leu Leu Ala Pro  Val Ala Leu Ala Cys Gly
                1180             1185             1190 atc gac ggc agt cta  tac gta ggg gat  ttc aat tac gtc cgg cgg    3664
Ile Asp Gly Ser Leu  Tyr Val Gly Asp  Phe Asn Tyr Val Arg Arg
                1195             1200             1205 ata ttc ccg tct ggg  aat gtg aca agt  gtt tta gaa cta aga aat    3709
Ile Phe Pro Ser Gly  Asn Val Thr Ser  Val Leu Glu Leu Arg Asn
                1210             1215             1220 aaa gat ttt aga cat  agt agc aac cca  gct cac aga tac tac ctg    3754
Lys Asp Phe Arg His  Ser Ser Asn Pro  Ala His Arg Tyr Tyr Leu
                1225             1230             1235 gct acg gac cca gtc  acc gga gat ttg  tac gtc tct gat act aac    3799
Ala Thr Asp Pro Val  Thr Gly Asp Leu  Tyr Val Ser Asp Thr Asn
                1240             1245             1250 acc cgc aga atc tat  cgg ccg aaa tca  ctc acg gga gcc aaa gac    3844
Thr Arg Arg Ile Tyr  Arg Pro Lys Ser  Leu Thr Gly Ala Lys Asp
                1255             1260             1265 ctg act aaa aac gct  gaa gtg gtg gca  ggg acc ggg gaa cag tgc    3889
Leu Thr Lys Asn Ala  Glu Val Val Ala  Gly Thr Gly Glu Gln Cys
                1270             1275             1280 ctt ccc ttt gac gag  gcc agg tgt ggg  gat gga ggc aag gct gtg    3934
Leu Pro Phe Asp Glu  Ala Arg Cys Gly  Asp Gly Gly Lys Ala Val
                1285             1290             1295 gaa gca acg ctc atg  agt ccc aaa gga  atg gca atc gat aag aac    3979
Glu Ala Thr Leu Met  Ser Pro Lys Gly  Met Ala Ile Asp Lys Asn
                1300             1305             1310 gga ctg atc tac ttt  gtt gat gga acc  atg atc aga aag gtt gat    4024
Gly Leu Ile Tyr Phe  Val Asp Gly Thr  Met Ile Arg Lys Val Asp
                1315             1320             1325 caa aat gga atc ata  tca act ctc ctg  ggc tcc aac gac ctc acg    4069
Gln Asn Gly Ile Ile  Ser Thr Leu Leu  Gly Ser Asn Asp Leu Thr
                1330             1335             1340 tca gct cga cct tta  acc tgt gat act  agc atg cat atc agc cag    4114
Ser Ala Arg Pro Leu  Thr Cys Asp Thr  Ser Met His Ile Ser Gln
                1345             1350             1355 gtg cgt ctg gaa tgg  ccc act gac ctc  gcg atc aac ccc atg gat    4159
Val Arg Leu Glu Trp  Pro Thr Asp Leu  Ala Ile Asn Pro Met Asp
                1360             1365             1370 aac tcc atc tac gtc  ctg gat aat aac  gta gtt tta cag atc act    4204
Asn Ser Ile Tyr Val  Leu Asp Asn Asn  Val Val Leu Gln Ile Thr
                1375             1380             1385 gaa aac cgt cag gtc  cgc atc gct gcc  ggg cgg ccc atg cac tgt    4249
Glu Asn Arg Gln Val  Arg Ile Ala Ala  Gly Arg Pro Met His Cys
                1390             1395             1400 cag gtc cct gga gtg  gaa tac ccg gtg  ggg aag cac gcg gtt cag    4294
Gln Val Pro Gly Val  Glu Tyr Pro Val  Gly Lys His Ala Val Gln
                1405             1410             1415 acc acc ctg gag tca  gcc acg gcc att  gct gtg tcc tac agc ggg    4339
Thr Thr Leu Glu Ser  Ala Thr Ala Ile  Ala Val Ser Tyr Ser Gly
                1420             1425             1430 gtc ctt tac atc acg  gaa act gat gag  aag aag atc aac cga ata    4384
Val Leu Tyr Ile Thr  Glu Thr Asp Glu  Lys Lys Ile Asn Arg Ile
                1435             1440             1445
```

```
agg cag gtc acg aca gac ggg gag atc tcc tta gtg gct ggg ata        4429
Arg Gln Val Thr Thr Asp Gly Glu Ile Ser Leu Val Ala Gly Ile
            1450                1455                1460 cct tcg gaa tgt gac tgc aag aac gac gcc aac tgt gac tgc tac        4474
Pro Ser Glu Cys Asp Cys Lys Asn Asp Ala Asn Cys Asp Cys Tyr
            1465                1470                1475 caa agc gga gac ggc tac gcc aaa gat gcc aaa ctc aat gcg ccg        4519
Gln Ser Gly Asp Gly Tyr Ala Lys Asp Ala Lys Leu Asn Ala Pro
            1480                1485                1490 tcc tcc ctg gcc gcc tcg cca gat ggc act ctg tac att gca gat        4564
Ser Ser Leu Ala Ala Ser Pro Asp Gly Thr Leu Tyr Ile Ala Asp
            1495                1500                1505 ctg gga aat atc agg atc cgg gcc gtt tcg aag aat aaa cct tta        4609
Leu Gly Asn Ile Arg Ile Arg Ala Val Ser Lys Asn Lys Pro Leu
            1510                1515                1520 ctg aac tca atg aac ttt tac gaa gtt gcc tct cca act gat caa        4654
Leu Asn Ser Met Asn Phe Tyr Glu Val Ala Ser Pro Thr Asp Gln
            1525                1530                1535 gag ctc tac atc ttt gac atc aac ggt act cac cag tac acc gtg        4699
Glu Leu Tyr Ile Phe Asp Ile Asn Gly Thr His Gln Tyr Thr Val
            1540                1545                1550 agc ctg gtc acg ggt gac tac cta tat aat ttt agt tac agc aat        4744
Ser Leu Val Thr Gly Asp Tyr Leu Tyr Asn Phe Ser Tyr Ser Asn
            1555                1560                1565 gac aat gac gtc acc gct gta act gac agc aat ggc aac acc ctc        4789
Asp Asn Asp Val Thr Ala Val Thr Asp Ser Asn Gly Asn Thr Leu
            1570                1575                1580 cga atc cga agg gat ccg aat cgg atg ccg gtg cgg gtg gtg tct        4834
Arg Ile Arg Arg Asp Pro Asn Arg Met Pro Val Arg Val Val Ser
            1585                1590                1595 cct gat aac cag gtg ata tgg ttg acc ata ggc acc aac ggg tgt        4879
Pro Asp Asn Gln Val Ile Trp Leu Thr Ile Gly Thr Asn Gly Cys
            1600                1605                1610 ctg aaa agc atg acc gct cag ggc ctg gaa ctg gtt ttg ttt act        4924
Leu Lys Ser Met Thr Ala Gln Gly Leu Glu Leu Val Leu Phe Thr
            1615                1620                1625 tac cat ggc aac agt ggg ctt tta gcc acc aaa agt gac gaa act        4969
Tyr His Gly Asn Ser Gly Leu Leu Ala Thr Lys Ser Asp Glu Thr
            1630                1635                1640 gga tgg aca aca ttt ttt gac tat gac agt gaa ggt cgc ctg acg        5014
Gly Trp Thr Thr Phe Phe Asp Tyr Asp Ser Glu Gly Arg Leu Thr
            1645                1650                1655 aat gtt acc ttc ccc act ggg gtg gtt aca aac ctg cac ggg gac        5059
Asn Val Thr Phe Pro Thr Gly Val Val Thr Asn Leu His Gly Asp
            1660                1665                1670 atg gac aag gct atc acg gtg gac atc gag tca tcc agc aga gag        5104
Met Asp Lys Ala Ile Thr Val Asp Ile Glu Ser Ser Ser Arg Glu
            1675                1680                1685 gaa gat gtc agc atc act tcg aac ttg tcc tcc atc gat tcc ttc        5149
Glu Asp Val Ser Ile Thr Ser Asn Leu Ser Ser Ile Asp Ser Phe
            1690                1695                1700 tac acc atg gtc caa gac cag tta aga aac agt tac cag att ggg        5194
Tyr Thr Met Val Gln Asp Gln Leu Arg Asn Ser Tyr Gln Ile Gly
            1705                1710                1715 tat gat ggc tcc ctt aga atc ttc tat gcc agt ggt ctg gac tct        5239
Tyr Asp Gly Ser Leu Arg Ile Phe Tyr Ala Ser Gly Leu Asp Ser
            1720                1725                1730 cac tac cag aca gag ccc cac gtt ctg gct ggc acg gcg aat ccc        5284
His Tyr Gln Thr Glu Pro His Val Leu Ala Gly Thr Ala Asn Pro
            1735                1740                1745
```

-continued

```
aca gta gcc aaa aga  aac atg act ctt ccc  ggt gag aac ggg cag        5329
Thr Val Ala Lys Arg  Asn Met Thr Leu Pro  Gly Glu Asn Gly Gln
            1750              1755                   1760 aat ctg gtg gag tgg  aga ttc cga aaa gaa  caa gcc cag ggc aaa        5374
Asn Leu Val Glu Trp  Arg Phe Arg Lys Glu  Gln Ala Gln Gly Lys
            1765              1770                   1775 gtc aac gta ttc ggc  cgg aag ctc agg gtc  aat ggg cgc aac cta        5419
Val Asn Val Phe Gly  Arg Lys Leu Arg Val  Asn Gly Arg Asn Leu
            1780              1785                   1790 ctc tca gtg gac ttt  gat cgg acc acc aag  acg gaa aag atc tat        5464
Leu Ser Val Asp Phe  Asp Arg Thr Thr Lys  Thr Glu Lys Ile Tyr
            1795              1800                   1805 gat gac cac cgg aaa  ttt ctc ctg agg atc  gct tac gac acg tcg        5509
Asp Asp His Arg Lys  Phe Leu Leu Arg Ile  Ala Tyr Asp Thr Ser
            1810              1815                   1820 ggg cac ccg act ctc  tgg ctg ccg agt agc  aag cta atg gca gtg        5554
Gly His Pro Thr Leu  Trp Leu Pro Ser Ser  Lys Leu Met Ala Val
            1825              1830                   1835 aac gtc acc tac tca  tcc acc ggt caa att  gcc agc atc cag aga        5599
Asn Val Thr Tyr Ser  Ser Thr Gly Gln Ile  Ala Ser Ile Gln Arg
            1840              1845                   1850 ggg acc acg agc gaa  aag gtg gac tat gac  agc cag ggg agg atc        5644
Gly Thr Thr Ser Glu  Lys Val Asp Tyr Asp  Ser Gln Gly Arg Ile
            1855              1860                   1865 gta tct cgg gtc ttt  gcc gat ggg aaa aca  tgg agt tac acg tac        5689
Val Ser Arg Val Phe  Ala Asp Gly Lys Thr  Trp Ser Tyr Thr Tyr
            1870              1875                   1880 ttg gaa aag tcc atg  gtt ctt ctg ctc cat  agc cag cgg cag tac        5734
Leu Glu Lys Ser Met  Val Leu Leu Leu His  Ser Gln Arg Gln Tyr
            1885              1890                   1895 atc ttc gaa tac gac  atg tgg gac cgc ctg  tcc gcc atc acc atg        5779
Ile Phe Glu Tyr Asp  Met Trp Asp Arg Leu  Ser Ala Ile Thr Met
            1900              1905                   1910 ccc agt gtg gct cgc  cac acc atg cag acc  atc cgg tcc att ggc        5824
Pro Ser Val Ala Arg  His Thr Met Gln Thr  Ile Arg Ser Ile Gly
            1915              1920                   1925 tac tac cgc aac atc  tac aat ccc cca gaa  agc aat gcc tct atc        5869
Tyr Tyr Arg Asn Ile  Tyr Asn Pro Pro Glu  Ser Asn Ala Ser Ile
            1930              1935                   1940 atc acc gac tac aac  gag gaa ggg ctg ctt  ctg caa aca gct ttc        5914
Ile Thr Asp Tyr Asn  Glu Glu Gly Leu Leu  Leu Gln Thr Ala Phe
            1945              1950                   1955 ctg gga acg agt cgg  agg gtc tta ttc aag  tat aga agg cag acc        5959
Leu Gly Thr Ser Arg  Arg Val Leu Phe Lys  Tyr Arg Arg Gln Thr
            1960              1965                   1970 agg cta tca gaa att  tta tac gac agc aca  aga gtc agt ttt acc        6004
Arg Leu Ser Glu Ile  Leu Tyr Asp Ser Thr  Arg Val Ser Phe Thr
            1975              1980                   1985 tac gac gaa aca gcg  gga gtc ctg aaa aca  gta aac ctt cag agt        6049
Tyr Asp Glu Thr Ala  Gly Val Leu Lys Thr  Val Asn Leu Gln Ser
            1990              1995                   2000 gat ggt ttt att tgc  acc att aga tac agg  caa att ggt ccc ctg        6094
Asp Gly Phe Ile Cys  Thr Ile Arg Tyr Arg  Gln Ile Gly Pro Leu
            2005              2010                   2015 att gac aga cag att  ttc cgc ttc agc gag  gat gga atg gta aat        6139
Ile Asp Arg Gln Ile  Phe Arg Phe Ser Glu  Asp Gly Met Val Asn
            2020              2025                   2030 gcg aga ttt gac tat  agc tac gac aac agc  ttt cga gtg acc agc        6184
Ala Arg Phe Asp Tyr  Ser Tyr Asp Asn Ser  Phe Arg Val Thr Ser
```

|   |   |   |   |   |   |   |   |   |   |   |   |   |   |   |   |   |
|---|---|---|---|---|---|---|---|---|---|---|---|---|---|---|---|---|
|   |   | 2035 |   |   |   | 2040 |   |   |   | 2045 |   |   |   |   |   |   |
| atg<br>Met | cag<br>Gln | ggt<br>Gly | gtc<br>Val | atc<br>Ile<br>2050 | aat<br>Asn | gaa<br>Glu | aca<br>Thr | cca<br>Pro | ctg<br>Leu<br>2055 | ccc<br>Pro | att<br>Ile | gat<br>Asp | cta<br>Leu | tac<br>Tyr<br>2060 | | 6229 |
| cag<br>Gln | ttt<br>Phe | gat<br>Asp | gac<br>Asp | atc<br>Ile<br>2065 | tct<br>Ser | ggc<br>Gly | aaa<br>Lys | gtc<br>Val | gag<br>Glu<br>2070 | cag<br>Gln | ttt<br>Phe | gga<br>Gly | aaa<br>Lys | ttc<br>Phe<br>2075 | | 6274 |
| gga<br>Gly | gtg<br>Val | ata<br>Ile | tac<br>Tyr | tac<br>Tyr<br>2080 | gac<br>Asp | atc<br>Ile | aac<br>Asn | caa<br>Gln | atc<br>Ile<br>2085 | att<br>Ile | tcc<br>Ser | acg<br>Thr | gcc<br>Ala | gtg<br>Val<br>2090 | | 6319 |
| atg<br>Met | act<br>Thr | tat<br>Tyr | aca<br>Thr | aag<br>Lys<br>2095 | cac<br>His | ttt<br>Phe | gat<br>Asp | gct<br>Ala | cat<br>His<br>2100 | ggg<br>Gly | cgc<br>Arg | atc<br>Ile | aag<br>Lys | gag<br>Glu<br>2105 | | 6364 |
| atc<br>Ile | caa<br>Gln | tat<br>Tyr | gag<br>Glu | ata<br>Ile<br>2110 | ttt<br>Phe | agg<br>Arg | tca<br>Ser | ctc<br>Leu | atg<br>Met<br>2115 | tac<br>Tyr | tgg<br>Trp | att<br>Ile | aca<br>Thr | att<br>Ile<br>2120 | | 6409 |
| caa<br>Gln | tat<br>Tyr | gat<br>Asp | aat<br>Asn | atg<br>Met<br>2125 | ggc<br>Gly | cgg<br>Arg | gta<br>Val | acc<br>Thr | aag<br>Lys<br>2130 | aga<br>Arg | gag<br>Glu | att<br>Ile | aaa<br>Lys | att<br>Ile<br>2135 | | 6454 |
| ggg<br>Gly | cct<br>Pro | ttt<br>Phe | gcc<br>Ala | aac<br>Asn<br>2140 | act<br>Thr | acc<br>Thr | aaa<br>Lys | tac<br>Tyr | gcg<br>Ala<br>2145 | tac<br>Tyr | gag<br>Glu | tac<br>Tyr | gac<br>Asp | gtc<br>Val<br>2150 | | 6499 |
| gat<br>Asp | gga<br>Gly | cag<br>Gln | ctc<br>Leu | caa<br>Gln<br>2155 | aca<br>Thr | gtt<br>Val | tac<br>Tyr | cta<br>Leu | aac<br>Asn<br>2160 | gaa<br>Glu | aag<br>Lys | atc<br>Ile | atg<br>Met | tgg<br>Trp<br>2165 | | 6544 |
| cgg<br>Arg | tac<br>Tyr | aac<br>Asn | tac<br>Tyr | gac<br>Asp<br>2170 | cta<br>Leu | aat<br>Asn | gga<br>Gly | aac<br>Asn | ctc<br>Leu<br>2175 | cac<br>His | ttg<br>Leu | ctc<br>Leu | aac<br>Asn | ccc<br>Pro<br>2180 | | 6589 |
| agc<br>Ser | agc<br>Ser | agc<br>Ser | gcc<br>Ala | cgc<br>Arg<br>2185 | ctg<br>Leu | acc<br>Thr | cct<br>Pro | ctg<br>Leu | cgc<br>Arg<br>2190 | tat<br>Tyr | gac<br>Asp | ctg<br>Leu | cgc<br>Arg | gac<br>Asp<br>2195 | | 6634 |
| aga<br>Arg | atc<br>Ile | acc<br>Thr | cgc<br>Arg | ctg<br>Leu<br>2200 | ggc<br>Gly | gat<br>Asp | gtt<br>Val | cag<br>Gln | tac<br>Tyr<br>2205 | cgg<br>Arg | ctg<br>Leu | gat<br>Asp | gaa<br>Glu | gat<br>Asp<br>2210 | | 6679 |
| ggt<br>Gly | ttc<br>Phe | ctg<br>Leu | cgt<br>Arg | cag<br>Gln<br>2215 | agg<br>Arg | ggc<br>Gly | act<br>Thr | gaa<br>Glu | att<br>Ile<br>2220 | ttt<br>Phe | gaa<br>Glu | tac<br>Tyr | agc<br>Ser | tcc<br>Ser<br>2225 | | 6724 |
| aaa<br>Lys | ggg<br>Gly | ctt<br>Leu | ctg<br>Leu | act<br>Thr<br>2230 | cga<br>Arg | gtc<br>Val | tac<br>Tyr | agt<br>Ser | aaa<br>Lys<br>2235 | ggc<br>Gly | agt<br>Ser | ggc<br>Gly | tgg<br>Trp | aca<br>Thr<br>2240 | | 6769 |
| gtg<br>Val | atc<br>Ile | tat<br>Tyr | cgg<br>Arg | tac<br>Tyr<br>2245 | gac<br>Asp | ggc<br>Gly | ctg<br>Leu | gga<br>Gly | aga<br>Arg<br>2250 | cgt<br>Arg | gtt<br>Val | tct<br>Ser | agc<br>Ser | aaa<br>Lys<br>2255 | | 6814 |
| acc<br>Thr | agc<br>Ser | ctg<br>Leu | gga<br>Gly | cag<br>Gln<br>2260 | cac<br>His | ctt<br>Leu | cag<br>Gln | ttt<br>Phe | ttc<br>Phe<br>2265 | tac<br>Tyr | gcc<br>Ala | gac<br>Asp | ctg<br>Leu | aca<br>Thr<br>2270 | | 6859 |
| tac<br>Tyr | ccc<br>Pro | acg<br>Thr | aga<br>Arg | att<br>Ile<br>2275 | act<br>Thr | cac<br>His | gtc<br>Val | tac<br>Tyr | aac<br>Asn<br>2280 | cat<br>His | tcc<br>Ser | agt<br>Ser | tca<br>Ser | gaa<br>Glu<br>2285 | | 6904 |
| atc<br>Ile | acc<br>Thr | tcc<br>Ser | ctg<br>Leu | tac<br>Tyr<br>2290 | tat<br>Tyr | gac<br>Asp | ctc<br>Leu | caa<br>Gln | gga<br>Gly<br>2295 | cat<br>His | ctc<br>Leu | ttc<br>Phe | gcc<br>Ala | atg<br>Met<br>2300 | | 6949 |
| gag<br>Glu | atc<br>Ile | agc<br>Ser | agt<br>Ser | ggg<br>Gly<br>2305 | gat<br>Asp | gag<br>Glu | ttc<br>Phe | tac<br>Tyr | atc<br>Ile<br>2310 | gcc<br>Ala | tcg<br>Ser | gac<br>Asp | aac<br>Asn | acg<br>Thr<br>2315 | | 6994 |
| ggg<br>Gly | aca<br>Thr | ccg<br>Pro | ctg<br>Leu | gct<br>Ala<br>2320 | gtt<br>Val | ttc<br>Phe | agc<br>Ser | agc<br>Ser | aac<br>Asn<br>2325 | ggg<br>Gly | ctc<br>Leu | atg<br>Met | ctg<br>Leu | aaa<br>Lys<br>2330 | | 7039 |
| cag<br>Gln | acc<br>Thr | cag<br>Gln | tac<br>Tyr | act<br>Thr | gcc<br>Ala | tat<br>Tyr | ggt<br>Gly | gag<br>Glu | atc<br>Ile | tac<br>Tyr | ttt<br>Phe | gac<br>Asp | tcc<br>Ser | aac<br>Asn | | 7084 |

| | |
|---|---|
| Gln Thr Gln Tyr Thr Ala Tyr Gly Glu Ile Tyr Phe Asp Ser Asn<br>2335                                         2340                           2345 | |
| gtc gac ttt cag ctg gta att gga ttc cac ggg ggc ttg tat gac<br>Val Asp Phe Gln Leu Val Ile Gly Phe His Gly Gly Leu Tyr Asp<br>                2350                         2355                         2360 | 7129 |
| ccg ctc acc aaa cta atc cac ttt gga gaa aga gat tat gac att<br>Pro Leu Thr Lys Leu Ile His Phe Gly Glu Arg Asp Tyr Asp Ile<br>                2365                         2370                         2375 | 7174 |
| ttg gcg gga aga tgg acc aca ccg gac att gaa atc tgg aaa agg<br>Leu Ala Gly Arg Trp Thr Thr Pro Asp Ile Glu Ile Trp Lys Arg<br>                2380                         2385                         2390 | 7219 |
| atc gga aag gac cct gct cct ttt aac ctg tat atg ttt cgg aat<br>Ile Gly Lys Asp Pro Ala Pro Phe Asn Leu Tyr Met Phe Arg Asn<br>                2395                         2400                         2405 | 7264 |
| aac aac ccc gcg agc aaa atc cat gat gtg aaa gat tac atc acg<br>Asn Asn Pro Ala Ser Lys Ile His Asp Val Lys Asp Tyr Ile Thr<br>                2410                         2415                         2420 | 7309 |
| gat gtt aac agc tgg ctg gtg acg ttt ggc ttc cat ctg cac aat<br>Asp Val Asn Ser Trp Leu Val Thr Phe Gly Phe His Leu His Asn<br>                2425                         2430                         2435 | 7354 |
| gct att cct gga ttc cct gtt ccc aaa ttt gat tta act gag cct<br>Ala Ile Pro Gly Phe Pro Val Pro Lys Phe Asp Leu Thr Glu Pro<br>                2440                         2445                         2450 | 7399 |
| tcc tat gag ctt gtg aag agt caa cag tgg gaa gat gtg ccg ccc<br>Ser Tyr Glu Leu Val Lys Ser Gln Gln Trp Glu Asp Val Pro Pro<br>                2455                         2460                         2465 | 7444 |
| atc ttt gga gtt cag cag caa gtg gca agg caa gcc aag gcc ttc<br>Ile Phe Gly Val Gln Gln Gln Val Ala Arg Gln Ala Lys Ala Phe<br>                2470                         2475                         2480 | 7489 |
| ttg tcc ctg ggg aag atg gcc gag gtg cag gtg agc cga cgc aaa<br>Leu Ser Leu Gly Lys Met Ala Glu Val Gln Val Ser Arg Arg Lys<br>                2485                         2490                         2495 | 7534 |
| gct ggc gcc gag cag tcg tgg ctg tgg ttc gcc acg gtc aag tcg<br>Ala Gly Ala Glu Gln Ser Trp Leu Trp Phe Ala Thr Val Lys Ser<br>                2500                         2505                         2510 | 7579 |
| ctc atc ggc aag ggc gtc atg ctg gcc gtg agc caa ggc cgc gtg<br>Leu Ile Gly Lys Gly Val Met Leu Ala Val Ser Gln Gly Arg Val<br>                2515                         2520                         2525 | 7624 |
| cag acc aac gtg ctc aac atc gcc aac gag gac tgc atc aag gtg<br>Gln Thr Asn Val Leu Asn Ile Ala Asn Glu Asp Cys Ile Lys Val<br>                2530                         2535                         2540 | 7669 |
| gcg gcg gtg ctc aac aac gcc ttc tac ctg gag aac ctg cac ttc<br>Ala Ala Val Leu Asn Asn Ala Phe Tyr Leu Glu Asn Leu His Phe<br>                2545                         2550                         2555 | 7714 |
| acc atc gag ggc aag gac aca cac tac ttc atc aag acc acc aca<br>Thr Ile Glu Gly Lys Asp Thr His Tyr Phe Ile Lys Thr Thr Thr<br>                2560                         2565                         2570 | 7759 |
| ccc gag agc gac ctg ggc aca ctg cgg ctg acg agc ggt cgc aag<br>Pro Glu Ser Asp Leu Gly Thr Leu Arg Leu Thr Ser Gly Arg Lys<br>                2575                         2580                         2585 | 7804 |
| gcc ctg gag aac ggg atc aac gtg acc gtg tct cag tcc acc acg<br>Ala Leu Glu Asn Gly Ile Asn Val Thr Val Ser Gln Ser Thr Thr<br>                2590                         2595                         2600 | 7849 |
| gtg gtg aac ggc agg act cgc agg ttc gcc gac gtg gag atg cag<br>Val Val Asn Gly Arg Thr Arg Arg Phe Ala Asp Val Glu Met Gln<br>                2605                         2610                         2615 | 7894 |
| ttc ggt gcc ctg gca ctg cat gtg cgc tat ggc atg acg ctg gac<br>Phe Gly Ala Leu Ala Leu His Val Arg Tyr Gly Met Thr Leu Asp<br>                2620                         2625                         2630 | 7939 |

-continued

```
gag gag aag gcg cgc att ctg gag cag gcg cgc cag cgc gcg ctc      7984
Glu Glu Lys Ala Arg Ile Leu Glu Gln Ala Arg Gln Arg Ala Leu
                2635                2640                2645 gcc cgg gcg tgg gca cgg gag cag cag cgc gtg cgc gac ggc gag      8029
Ala Arg Ala Trp Ala Arg Glu Gln Gln Arg Val Arg Asp Gly Glu
            2650                2655                2660 gag ggt gcg cgc ctc tgg acg gag ggt gag aaa cgg cag ctg ctg      8074
Glu Gly Ala Arg Leu Trp Thr Glu Gly Glu Lys Arg Gln Leu Leu
        2665                2670                2675 agc gct ggc aag gtg cag ggc tac gat ggg tac tac gta ctg tcg      8119
Ser Ala Gly Lys Val Gln Gly Tyr Asp Gly Tyr Tyr Val Leu Ser
    2680                2685                2690 gtg gag cag tac ccc gag ctg gct gac agt gcc aac aac atc cag      8164
Val Glu Gln Tyr Pro Glu Leu Ala Asp Ser Ala Asn Asn Ile Gln
2695                2700                2705 ttc ttg cga caa agt gag atc ggc aag agg taa ccccgggcc            8207
Phe Leu Arg Gln Ser Glu Ile Gly Lys Arg
                2710            2715 accctgtgc agattctcct gtagcacaat ccaaaccgga ctctccaaag agccttccaa  8267
aatgacactg ctctgcagac agacacatcg cagatacaca cgcaacacaa accagaaaca  8327
aagacaactt ttttttttt ctgaatgacc ttaaggtga tcggctttaa agaatatgtt  8387
tacatacgca tatcgctgca ctcaattgga ctggaagtat gagaaaggaa aaaaagcat  8447 taaaaaggc aacgttttgc catgacccct ctgtaccttc gaggcactgt atttaacaaa  8507
ggttttaaaa aggaaaaaaa aatgcgtaca atgtttccag atattactga attgtcgacc  8567
tttgcttaca ggaagtaatc tctacttagg atgtgatata tatagatctg ttcattttaa  8627
aatgtggggc aaagttactg tttatagaac ccaactgctt tcccgtgctg ctttgtaaaa  8687
ggacactggc acaagggacg tctgcttcgg cggggattta ataatggatt ttactaacat  8747
ggcttgccct gggagggaaa aactgacgaa tagaatcctt gtcactgata agcaaggaa   8807 accctgattt ttttgtaaat tatgtgagac aagttgttta tggattttta tatgaattac  8867
aatttactgt acatcaaata ttagtctcag aggagttaat ttatgtaaag tgtttaaaaa  8927
gtttatactt aaaaataaaa tgataaaaac aaaaaaa                          8964

<210> SEQ ID NO 133
<211> LENGTH: 2253
<212> TYPE: DNA
<213> ORGANISM: Homo sapiens
<220> FEATURE:
<221> NAME/KEY: exon
<222> LOCATION: (107)..(1090)
<223> OTHER INFORMATION:

<400> SEQUENCE: 133
gtgccccgga tgtgcccagc tggctcctgg ccccaccccct cgggcctttg ggctggacca   60
gccacctctg cctgagacct ccggtcgccg caagaagctg gagagg atg tac agc     115
                                                  Met Tyr Ser
                                                    1 gtt gac cgt gtg tct gac gac atc cct att cgt acc tgg ttc ccc aag    163
Val Asp Arg Val Ser Asp Asp Ile Pro Ile Arg Thr Trp Phe Pro Lys
        5                   10                  15 gaa aat ctt ttc agc ttc cag aca gca acc aca act atg caa gcg gtg    211
Glu Asn Leu Phe Ser Phe Gln Thr Ala Thr Thr Thr Met Gln Ala Val
 20                  25                  30                  35 ttc agg ggc tac gcg gag agg aag cgc cgg aaa cgg gag aat gat tcc    259
Phe Arg Gly Tyr Ala Glu Arg Lys Arg Arg Lys Arg Glu Asn Asp Ser
                 40                  45                  50
```

```
gcg tct gta atc cag agg aac ttc cgc aaa cac ctg cgc atg gtc ggc      307
Ala Ser Val Ile Gln Arg Asn Phe Arg Lys His Leu Arg Met Val Gly
        55                  60                  65 agc cgg agg gtg aag gcc cag acg ttc gct gag cgc gag cgg agc          355
Ser Arg Arg Val Lys Ala Gln Thr Phe Ala Glu Arg Glu Arg Ser
    70                  75                  80 ttc agc cgg tcc tgg agc gac ccc acc ccc atg aaa gcc gac act tcc      403
Phe Ser Arg Ser Trp Ser Asp Pro Thr Pro Met Lys Ala Asp Thr Ser
85                  90                  95 cac gac tcc cga gac agc agt gac ctg cag agc tcc cac tgc acg ctg      451
His Asp Ser Arg Asp Ser Ser Asp Leu Gln Ser Ser His Cys Thr Leu
100                 105                 110                 115 gac gag gcc ttc gag gac ctg gac tgg gac act gag aag ggc ctg gag      499
Asp Glu Ala Phe Glu Asp Leu Asp Trp Asp Thr Glu Lys Gly Leu Glu
                    120                 125                 130 gct gtg gcc tgc gac acc gaa ggc ttc gtg cca cca aag gtc atg ctc      547
Ala Val Ala Cys Asp Thr Glu Gly Phe Val Pro Pro Lys Val Met Leu
                135                 140                 145 att tcc tcc aag gtg ccc aag gct gag tac atc ccc act atc atc cgc      595
Ile Ser Ser Lys Val Pro Lys Ala Glu Tyr Ile Pro Thr Ile Ile Arg
        150                 155                 160 cgg gat gac ccc tcc atc atc ccc atc ctc tac gac cat gag cac gca      643
Arg Asp Asp Pro Ser Ile Ile Pro Ile Leu Tyr Asp His Glu His Ala
    165                 170                 175 acc ttc gag gac atc ctt gag gag ata gag agg aag ctg aac gtc tac      691
Thr Phe Glu Asp Ile Leu Glu Glu Ile Glu Arg Lys Leu Asn Val Tyr
180                 185                 190                 195 cac aag gga gcc aag atc tgg aaa atg ctg att ttc tgc cag gga ggt      739
His Lys Gly Ala Lys Ile Trp Lys Met Leu Ile Phe Cys Gln Gly Gly
                    200                 205                 210 cct gga cac ctc tat ctc ctc aag aac aag gtg gcc acc ttt gcc aaa      787
Pro Gly His Leu Tyr Leu Leu Lys Asn Lys Val Ala Thr Phe Ala Lys
                215                 220                 225 gtg gag aag gaa gag gac atg att cac ttc tgg aag cgg ctg agc cgc      835
Val Glu Lys Glu Glu Asp Met Ile His Phe Trp Lys Arg Leu Ser Arg
        230                 235                 240 ctg atg agc aaa gtg aac cca gag ccg aac gtc atc cac atc atg ggc      883
Leu Met Ser Lys Val Asn Pro Glu Pro Asn Val Ile His Ile Met Gly
    245                 250                 255 tgc tac att ctg ggg aac ccc aat gga gag aag ctg ttc cag aac ctc      931
Cys Tyr Ile Leu Gly Asn Pro Asn Gly Glu Lys Leu Phe Gln Asn Leu
260                 265                 270                 275 agg acc ctc atg act cct tat agg gtc acc ttc gag tca ccc ctg gag      979
Arg Thr Leu Met Thr Pro Tyr Arg Val Thr Phe Glu Ser Pro Leu Glu
                    280                 285                 290 ctc tca gcc caa ggg aag cag atg atc gag acg tac ttt gac ttc cgg     1027
Leu Ser Ala Gln Gly Lys Gln Met Ile Glu Thr Tyr Phe Asp Phe Arg
                295                 300                 305 ttg tat cgc ctg tgg aag agc cgc cag cac tcg aag ctg ctg gac ttt     1075
Leu Tyr Arg Leu Trp Lys Ser Arg Gln His Ser Lys Leu Leu Asp Phe
        310                 315                 320 gac gac gtc ctg tga ggggcagagg cctccgccca gtcaccatca ggccactccc     1130
Asp Asp Val Leu
            325 tctgcaccgg gacctggggc tgggccgcct cgtgctcccc gggactgtgt agctccggtc   1190 tcgcctggag ccacttcagg gcacctcaga cgttgctcag gttccccctg tgggttccgg   1250 tcctcgctgc acccgtggcc gcagaggctg cagtccctgg gggccgggag gatcccgccc   1310
```

-continued

```
tgtggcccgt ggatgctcag cggccaggca ctgacctgcc atgcctcgcc tggaggctca    1370
gctgtgggca tccctccatg gggttcatag aaataagtgc aatttctaca cccccgaaac    1430
aattcaaagg gaagcagcat ttcttgttaa ctagttaagc actatgctgc tagttacagt    1490
gtaggcaccc cggcccagca gcccagcagc ccacatgtgt tcaggaccct ccctgcccac    1550
cccctccctg ccgtatcgat caccagcacc agggtggccc gtgtgcgtgg ggccagcgtc    1610
gccgggctgc ccagcctggc tctgtctaca ctggccgagt ctctgggtct gtctacactg    1670
gccgagtctc cgactgtctg tgctttcact tacactcctc ttgccacccc ccatccctgc    1730
ttacttagac ctcagccggc gccggacccg gtaggggcag tctgggcagc aggaaggaag    1790
ggcgcagcgt ccctccttc agaggaggct ctgggtgggg cctgctcctc atcccccaa     1850
gcccacccag cactctcatt gctgctgttg agttcagctt ttaccagcct cagtgtggag    1910
gctccatccc agcacacagg cctggggctt ggcaggggcc cagctggggc tgggccctgg    1970
gttttgagaa actcgctggc accacagtgg gcccctggac ccggccgcgc agctggtgga    2030
ctgtaggggc tcctgactgg gcacaggagc tcccagcttt tgtccacggc cagcaggatg    2090
ggctgtcgtg tatatagctg gggcgagggg gcaggccccc cttgtgcaga gccagggggtc   2150
tgagggcacc tggctgtgtt cccagctgag ggagggctgg ggcgggggcc gggcttggaa    2210
cgatgtacga taccctcata gtgaccatta aacctgatcc tcc                      2253
```

<210> SEQ ID NO 134
<211> LENGTH: 2253
<212> TYPE: DNA
<213> ORGANISM: Danio rerio
<220> FEATURE:
<221> NAME/KEY: exon
<222> LOCATION: (1)..(298)
<223> OTHER INFORMATION:

<400> SEQUENCE: 134

```
gtg ccc cgg atg tgc cca gct ggc tcc tgg ccc cac ccc tcg ggc ctt       48
Val Pro Arg Met Cys Pro Ala Gly Ser Trp Pro His Pro Ser Gly Leu
1               5                   10                  15 tgg gct gga cca gcc acc tct gcc tga gac ctc cgg tcg ccg caa gaa       96
Trp Ala Gly Pro Ala Thr Ser Ala     Asp Leu Arg Ser Pro Gln Glu
                20                  25                  30 gct gga gag gat gta cag cgt tga ccg tgt gtc tga cga cat ccc tat      144
Ala Gly Glu Asp Val Gln Arg     Pro Cys Val     Arg His Pro Tyr
            35                      40                  45 tcg tac ctg gtt ccc caa gga aaa tct ttt cag ctt cca gac agc aac      192
Ser Tyr Leu Val Pro Gln Gly Lys Ser Phe Gln Leu Pro Asp Ser Asn
            50                  55                  60 cac aac tat gca agc ggt gtt cag ggg cta cgc gga gag gaa gcg ccg      240
His Asn Tyr Ala Ser Gly Val Gln Gly Leu Arg Gly Glu Glu Ala Pro
            65                  70                  75 gaa acg gga gaa tga ttc cgc gtc tgt aat cca gag gaa ctt ccg caa      288
Glu Thr Gly Glu     Phe Arg Val Cys Asn Pro Glu Glu Leu Pro Gln
            80                  85                  90 aca cct gcg c atggtcggca gccgagggt gaaggcccag acgttcgctg             338
Thr Pro Ala
        95 agcggcgcga gcggagcttc agccggtcct ggagcgaccc cacccccatg aaagccgaca    398
cttcccacga ctcccgagac agcagtgacc tgcagagctc ccactgcacg ctggacgagg    458
ccttcgagga cctggactgg gacactgaga agggcctgga ggctgtggcc tgcgacaccg    518
aaggcttcgt gccaccaaag gtcatgctca tttcctccaa ggtgcccaag gctgagtaca    578
```

```
tccccactat catccgccgg gatgacccct ccatcatccc catcctctac gaccatgagc    638
acgcaacctt cgaggacatc cttgaggaga tagagaggaa gctgaacgtc taccacaagg    698
gagccaagat ctggaaaatg ctgattttct gccagggagg tcctggacac ctctatctcc    758
tcaagaacaa ggtggccacc tttgccaaag tggagaagga gaggacatg attcacttct     818 ggaagcggct gagccgcctg atgagcaaag tgaacccaga gccgaacgtc atccacatca    878
tgggctgcta cattctgggg aaccccaatg gagagaagct gttccagaac ctcaggaccc    938
tcatgactcc ttatagggtc accttcgagt cacccctgga gctctcagcc caagggaagc    998
agatgatcga gacgtacttt gacttccggt tgtatcgcct gtggaagagc cgccagcact    1058
cgaagctgct ggactttgac gacgtcctgt gaggggcaga ggcctccgcc cagtcaccat    1118
caggccactc cctctgcacc gggacctggg gctgggccgc ctcgtgctcc ccgggactgt    1178
gtagctccgg tctcgcctgg agccacttca gggcacctca gacgttgctc aggttccccc    1238
tgtgggttcc ggtcctcgct gcacccgtgg ccgcagaggc tgcagtccct ggggccgggg    1298
aggatcccgc cctgtggccc gtggatgctc agcggccagg cactgacctg ccatgcctcg    1358
cctggaggct cagctgtggg catccctcca tggggttcat agaaataagt gcaatttcta    1418
cacccccgaa acaattcaaa gggaagcagc atttcttgtt aactagttaa gcactatgct    1478
gctagttaca gtgtaggcac cccggcccag cagcccagca gcccacatgt gttcaggacc    1538
ctccctgccc accccctccc tgccgtatcg atcaccagca ccagggtggc ccgtgtgcgt    1598
ggggccagcg tcgccgggct gcccagcctg gctctgtcta cactggccga gtctctgggt    1658
ctgtctacac tggccgagtc tccgactgtc tgtgctttca cttacactcc tcttgccacc    1718
ccccatccct gcttacttag acctcagccg gcgccggacc cggtaggggc agtctgggca    1778
gcaggaagga agggcgcagc gtcccctcct tcagaggagg ctctgggtgg ggcctgctcc    1838 tcatccccc aagcccaccc agcactctca ttgctgctgt tgagttcagc ttttaccagc     1898
ctcagtgtgg aggctccatc ccagcacaca ggcctggggc ttgcagggg cccagctggg     1958 gctgggccct gggttttgag aaactcgctg gcaccacagt gggcccctgg acccggccgc    2018
gcagctggtg gactgtaggg gctcctgact gggcacagga gctcccagct tttgtccacg    2078
gccagcagga tgggctgtcg tgtatatagc tggggcgagg gggcaggccc ccttgtgca     2138 gagccagggg tctgagggca cctggctgtg ttcccagctg agggagggct ggggcgggg     2198 ccgggcttgg aacgatgtac gataccctca tagtgaccat taaacctgat cctcc         2253
```

<210> SEQ ID NO 135
<211> LENGTH: 40
<212> TYPE: PRT
<213> ORGANISM: Artificial Sequence
<220> FEATURE:
<223> OTHER INFORMATION: TCAP 3 General Motif
<220> FEATURE:
<221> NAME/KEY: MISC_FEATURE
<222> LOCATION: (5)..(5)
<223> OTHER INFORMATION: X=G, S or A
<220> FEATURE:
<221> NAME/KEY: MISC_FEATURE
<222> LOCATION: (6)..(6)
<223> OTHER INFORMATION: X=G or R
<220> FEATURE:
<221> NAME/KEY: MISC_FEATURE
<222> LOCATION: (9)..(9)
<223> OTHER INFORMATION: X=L or Q
<220> FEATURE:
<221> NAME/KEY: MISC_FEATURE
<222> LOCATION: (19)..(19)

```
<223> OTHER INFORMATION: X=V or I
<220> FEATURE:
<221> NAME/KEY: MISC_FEATURE
<222> LOCATION: (32)..(32)
<223> OTHER INFORMATION: X=V or I

<400> SEQUENCE: 135

Gln Leu Leu Ser Xaa Xaa Lys Val Xaa Gly Tyr Asp Gly Tyr Tyr Val
 1               5                  10                  15

Leu Ser Xaa Glu Gln Tyr Pro Glu Leu Ala Asp Ser Ala Asn Asn Xaa
            20                  25                  30

Gln Phe Leu Arg Gln Ser Glu Ile
        35                  40

<210> SEQ ID NO 136
<211> LENGTH: 36
<212> TYPE: PRT
<213> ORGANISM: Artificial Sequence
<220> FEATURE:
<223> OTHER INFORMATION: G. gallus TCAP2

<400> SEQUENCE: 136

Thr Gly Arg Val Gln Gly Tyr Glu Gly Tyr Tyr Val Leu Pro Val Glu
 1               5                  10                  15

Gln Tyr Pro Glu Leu Ala Asp Ser Ser Ser Asn Ile Gln Phe Leu Arg
            20                  25                  30

Gln Asn Glu Met
        35
```

METHOD FOR REGULATING NEURITE GROWTH

RELATED APPLICATIONS

This application is a continuation of U.S. application Ser. No. 11/706,375, filed on Feb. 15, 2007, which is a continuation-in-part of U.S. application Ser. No. 10/510,959, filed Aug. 10, 2005, entitled "Teneurin C-Terminal Associated Peptides (TCAP) and Uses Thereof" which was a national phase entry of PCT/CA2003/00622 filed May 2, 2003, which was a non-provisional of U.S. provisional patent application No. U.S. 60/376,879, filed May 2, 2002, and a non-provisional of U.S. provisional patent application No. U.S. 60/377,231, filed May 3, 2002, and a non-provisional of U.S. provisional patent application No. U.S. 60/424,016, filed Nov. 6, 2002. U.S. application Ser. No. 11/706,375 also claims priority from U.S. provisional patent application No., U.S. 60/73,309, filed Feb. 15, 2006, entitled "A Method for Inhibiting Neuronal Cell Death". U.S. application Ser. No. 11/706,375 also claims priority from U.S. provisional patent application No. U.S. 60/783,321, filed Mar. 21, 2005, entitled "Method for Regulating Neurite Growth". All of these references are incorporated in their entirety by reference. Further, all sequence listings enclosed herewith and associated with this file in computer readable form are incorporated herein by reference.

FIELD OF THE INVENTION

This invention relates to a method for regulating neurite growth. In another aspect, it relates to a method for inhibiting neuronal cell death. In another aspect, it further relates to the neuroprotective effects of teneurin C-terminal associate peptides (TCAP) and to methods and uses of TCAP as a neuroprotective agent and/or to inhibit neuronal cell death and to regulate neurite growth. It further relates to the use of TCAP to induce neuronal growth, increase β-tubulin and β-actin levels in neuronal cells and induce fasciculation of neuronal cells, cultures or tissue, such as primary embryonic hippocampal cultures.

BACKGROUND OF THE INVENTION

The teneurins are a family of four vertebrate type II transmembrane proteins preferentially expressed in the central nervous system (Baumgartner et al., 1994). The teneurins are about 2800 amino acids long and possess a short membrane spanning region. The extracellular face consists of a number of structurally distinct domains suggesting that the protein may possess a number of distinct functions (Minet and Chiquet-Ehrismann, 2000; Minet et al., 1999; Oohashi et al., 1999). The gene was originally discovered in *Drosophila* as a pair rule gene and was named tenascin-major (Ten-M) or Odz (Baumgartner et al., 1994; Levine et al., 1994). It is expressed in the *Drosophila* nervous system and targeted disruption of the genes leads to embryonic lethality (Baumgartner et al., 1994). In immortalized mouse cells, expression of the teneurin protein led to increased neurite outgrowth (Rubin et al., 1999).

The extracellular C-terminal region of each teneurin is characterized by a 40 or 41 amino acid sequence flanked by enzymatic cleavage sites, which predicts the presence of an amidated cleaved peptide (Qian et al., 2004; Wang et al., 2005). A synthetic version of this peptide was named teneurin C-terminus associated peptide (TCAP) and is active in vivo and in vitro. The mouse TCAP from teneurin-1 (TCAP-1) can modulate cAMP concentrations and proliferation in mouse hypothalamic cell lines as well as regulate the teneurin protein in a dose dependent manner (Wang et al, 2004). Intracerebroventricular injection of TCAP-1 into rats can induce changes in the acoustic startle response three weeks after administration (Wang et al., 2005). [Also see, PCT/CA2003/000622. filed May 2, 2003, published Nov. 13, 2003, herein incorporated by reference.]

Currently, it is thought that following initial trauma, neurons die by necrosis, apoptosis or a combination of the two (Thompson, 1995; Columbano., 1995; Rosser and Gores, 1995; Watson, 1995). Necrosis has been defined as unprogrammed cell death induced by physiological trauma, such as hypoxia, injury, infection and cancer. The role of pH in the brain during these times of stress depends upon the trauma inflicted as both phenomenon can occur simultaneously depending upon pathological conditions, physiological activators, physical trauma, environmental toxins and carcinogenic chemicals (Wyllie et al., 1980; Arends and Willie, 1991; Buja et al., 1993; Majno and Jorris, 1995). Various neurodegenerative diseases, such as brain ischemia and Huntington's Disease, exist contingent upon various forms of cell death that in turn are mediated by their environments' surrounding pH. Although extracellular pH changes under normal metabolic circumstances, a number of pathological conditions affect pH and lead to cell death.

One of the logistical problems in understanding cell death and its corroborating factors is the ambiguity surrounding cell death. The current research indicates that many characteristics that were once thought to pertain only to apoptosis, now apply to necrosis as well. The current consensus is that following the initial insult such as during brain ischemia, brain cells die by necrosis, apoptosis or a combination of the two and pH plays a pivotal role during these times, specifically alkaline pH (Levine et al., 1992; Robertson, 2002).

Although, the literature on brain acidosis is extensive, brain alkalosis, is not well understood (Robertson, 2002). Intracellular alkalinization has been observed in cells undergoing cytokine deprivation (Khaled, 1999) as well as hypoxia-ischemia (HI) (Robertson, 2002). For example, during brain ischemia, brain pH levels indicated a progression from early acidosis to subacute alkalosis (Levine et al., 1992).

There is a need to counteract the effects of stress, such as pH induced cellular stress on the brain and to develop methods and compounds to protect cells against said effects, accordingly. Further there is a need to regulate neurite growth which may be beneficial in the diagnosis and treatment of various neuronal conditions.

SUMMARY OF THE INVENTION

In one aspect the invention provides a method for inhibiting neuronal cells against cell death. The inventors have surprisingly found that TCAP treated cells survive better in stress conditions, for instance in pH induced stress conditions, and in one aspect in alkaline pH conditions compared to vehicle treated cells.

As such, in one aspect the invention provides a method for inhibiting neuronal cells against cell death by administering an effective amount of TCAP, pharmaceutically acceptable salt or ester thereof or obvious chemical equivalent thereof to the cells. In another embodiment, administration of TCAP to the cells is administration of TCAP to a patient in need thereof comprising said cells. In one aspect the patient in need thereof is a patient who sustained or is suspected to have sustained a physiological trauma. In one aspect, a pharmaceutical composition comprising TCAP, pharmaceutically acceptable salt or ester or obvious chemical equivalent thereof and a pharmaceutically acceptable carrier is administered.

In one aspect, the invention provides a method of inhibiting and/or preventing neuronal cell death comprising administering to the cell an effective amount of TCAP, a pharmaceutical acceptable salt or ester thereof or obvious chemical equivalent thereof.

In one embodiment, inhibiting neuronal cell death comprises inhibiting and/or protecting and/or preventing neuronal cells from cell death under conditions where cell death may occur, such as a result of physiological trauma.

In one embodiment, conditions wherein cell death may occur are conditions conducive to necrosis. As such, in one aspect the invention provides a method of inhibiting, preventing or protecting neuronal cells from cell death by necrosis by administering an effective amount of TCAP, pharmaceutically acceptable salt or ester thereof or obvious chemical equivalent thereof.

In one embodiment, conditions where cell death may occur is stress-induced neuronal cell death, such as pH-induced neuronal cell death. In one aspect, pH-induced neuronal cell death is alkalosis-stress induced neuronal cell death or cell death as a result of high pH conditions. In one aspect, high pH conditions are conditions wherein pH is greater than 7.4. In another aspect, the pH is 8.0 or greater. In another aspect, the pH is from 8.0 to 9.0, 8.0 to 8.5, or 8.0 to 8.4. In another aspect, one condition of pH induced stress is from 6.0 to 7.4 or at pH 6.8.

In another aspect, the physiological trauma is selected from the group consisting of: hypoxia, injury, infection, cytokine deprivation, carcinogenic agents and cancer and/or is related to or the result of a neurodegenerative disease.

In one aspect, the neurodegenerative disease is selected from the group consisting of: Alzheimer's, Parkinson's, Huntington's, Multiple Sclerosis and brain ischemia.

In yet another embodiment, the physiological trauma is selected from the group consisting of: hypothermia, hypoxia, acute ischemia, hypoxia-ischemia, respiratory alkalosis, metabolic alkalosis and brain alkalosis. In another embodiment, it is traumatic injury to the brain or spinal cord or a result of secondary energy failure post the physiological trauma.

In one embodiment, the invention provides a method for using an effective amount of TCAP, pharmaceutical acceptable salt or ester thereof or obvious chemical equivalent thereof in the treatment of a neuronal condition associated with alkaline neuronal cell pH, by administering said TCAP to the patient in need thereof. In one aspect said condition is related to pH conditions greater than 7.4, 8.0 or greater, from 8.0 to 9.0, or from 8.0 to 8.4.

In one embodiment of the aforementioned methods of the invention, the neuronal cell is a immortalized mouse hypothalamic cell.

In one embodiment, the invention provides a method of screening of modulators of the neuronal cell death inhibitory effects of TCAP, comprising administering TCAP to neuronal cells under conditions that would normally induce neuronal cell death if TCAP were not present (e.g. pH induced cell death, alkalosis induced cell death); administering a suspected modulator of said TCAP function and determining the effects of said suspected modulator on TCAP inhibition of neuronal cell death. If said suspected modulator enhances TCAP inhibition of neuronal cell death or decreases TCAP inhibition of neuronal cell death, then it is a modulator of TCAP inhibition of neuronal cell death. In one embodiment, said suspected modulator is administered to the cells prior to, simultaneously with and/or after administration of TCAP. In another embodiment, determining the effects of said modulator comprises comparing the levels of neuronal cell death and/or survival with a control, such as cell death absent the presence of TCAP or modulator; in the presence of TCAP alone or modulator alone, or compared to established baseline effects of neuronal cell death under various conditions.

In another aspect of the invention, the invention provides a method for increasing neuronal cell proliferation under conditions of neutral pH or acidosis pH conditions. In one embodiment, the pH conditions are pH of 7.4 or less. In another embodiment, the pH conditions are 6.8 or less. In yet another embodiment the pH conditions are between 6.8 and 7.4.

In another embodiment, the invention provides a method to regulate neurite growth by administering TCAP to neuronal cells. In another embodiment, the invention provides of a method of inducing neuronal growth by administering an effective amount of TCAP to neuronal cells. In another aspect, the invention provides a use of TCAP to increase β-tubulin and/or β-actin levels in neuronal cells. In one aspect, the invention provides a method for treating conditions related to β-tubulin and/or β-actin levels, such as memory loss, learning disorders, neurodegenerative diseases and necrosis or inflammation resulting from trauma to the central nervous system.

In another aspect, the invention provides a method or use of TCAP to induce fasciculation of neuronal cells, cultures or tissue, such as primary embryonic hippocampal cultures. In yet another embodiment, the invention provides a method for treating a condition that can be treated by increasing fasciculation among neuronal cells, such as in the treatment of physiological or physical trauma to neuronal cells, such brain d injuries.

In another embodiment, the invention provides a method or use of TCAP as a guidance molecule. Axonal guidance and pathfinding is anormal and necessary aspect of neuroregeneration and restoration of function following a trauma. As such, in one aspect, the invention includes a method for axonal guidance or neurogeneration comprising administering an effective amount of TCAP to a neuron or patient in need thereof.

Additional aspects and advantages of the present invention will be apparent in view of the description which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The invention will now be described in relation to the drawings, in which:

FIG. 1A. Cell Morphology of N38 cells at 48 hrs as a function of pH treatment.

FIG. 1B. Cell Morphology of N38 cells at 72 hrs as a function of pH treatment.

FIG. 1C. Example of necrotic cell.

FIG. 1D. Quantification of small crenated (necrotic) cells. The levels of significance were determined by two-way ANOVA using Bonferroni's Post Test.

FIG. 2A. Proliferation of N38 cells a function of pH. TCAP-1($10^{-7}$ M) increased the number of cells post 48 hrs after treatment at pH extremes 6.8, 8.0, 8.4. The level of significance was determined using a two-way analysis of variance (ANOVA).

FIG. 2B. Changes in cell viability, over 48 hours as determined by trypan blue. TCAP increased the number of viable cells at pH 6.8 ($p<0.10$) pH 8.0 ($p<0.001$) and pH 8.4 ($p<0.05$). The level of significance was determined using a two-way analysis of variance (ANOVA).

FIG. 9A illustrates untreated cells at 8 hours. FIG. 9B illustrates cells treated with 100 nM of TCAP-1 at 8 hours. FIG. 9C illustrates percent change in neurite length in control (untreated), 1 nM TCAP-1 and 100 nM TCAP-1 at 0, 4 and 8 hours post TCAP administration. FIG. 9D illustrates percent change of number of neurites in control (untreated), 1 nM TCAP-1 and 100 nM TCAP-1 at 0, 4, and 8 hours post TCAP administration. FIGS. 9E and 9F illustrate the frequency distribution in neurite length of the cell population in untreated (9E) and 100 nM TCAP-1 treated (9F) samples.

FIG. 18 illustrates the results as described in Example 8, wherein FIG. 18A illustrates the presence of the superoxide radical measured indirectly by the conversion of a soluble tetrazolium salt in cells after 48 hours. Absorbance of the substrate is proportional to superoxide radical activity. FIGS. 18B and 18C illustrate the presence of superoxide dismutase directly by western blot (FIG. 18C) and change relative to vehicle treated cells (percent) versus pH (FIG. 18B). FIG. 18D illustrates superoxide dismustase gene expression as measured by real-time PCR, while FIG. 18E illustrate superoxide copper chaperone expression as measured by real-time PCR.

FIG. 19 illustrates the results as described in Example 8.

DETAILED DESCRIPTION OF THE INVENTION

Figure 3:
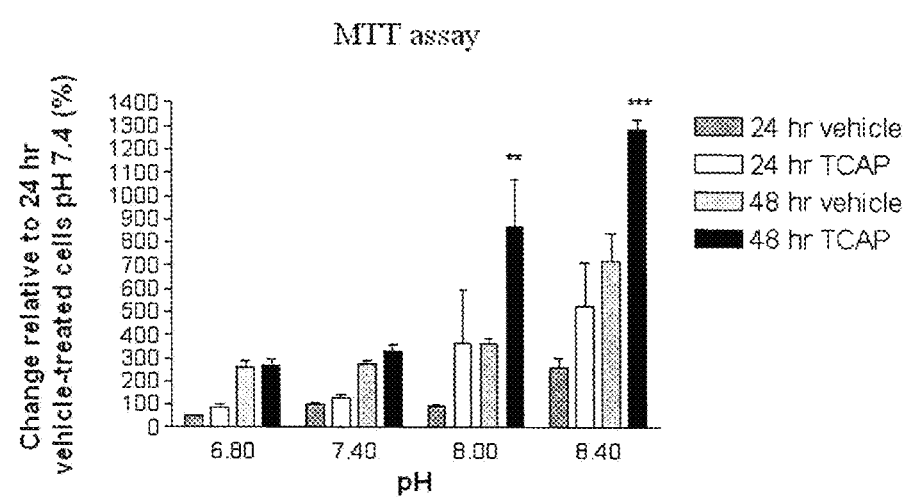
FIG. 3. Changes in mitochondrial metabolism of N38 cells as determined by the MTT assay. TCAP-1 ($10^{-7}$M) increased the number of viable cells post 48 hrs after treatment at pH extremes 8.0 and 8.4. The level of significance was determined using a two-way analysis of variance (ANOVA).

As described herein, teneurin C-terminus associated peptide (TCAP) inhibits neuronal cell death, such as during timed of pH induced cellular stress in the brain. In another aspect, TCAP has a neuroprotective effect, protecting neuronal cells from cell death, such as, during times of pH induced cellular stress in the brain. In one aspect of the invention, such pH induced cellular stress in the brain is related to hypoxia-ischemia and/or brain alkalosis. In the examples described herein, an immortalized hypothalamic mouse cell line (N38) was treated with medium buffered at pHs 6.8, 7.4, 8.0 and 8.4 treated with 100 nM TCAP and examined at 24 and 48 hours. TCAP significantly increased cell proliferation at pH 6.8 and inhibited declines in cell proliferation at pHs 8.0 and 8.4 as determined by direct cell viability assays. TCAP did not significantly alter caspase 8 and 3 activity, nor induce PARP cleavage. TCAPs effects on the S phase of cell cycling were investigated through a bromodeoxyuridine (BrdU) uptake assay, the results showing that TCAP does not have a major effect during the S phase of cell proliferation. The incidence of necrosis was tested via cell viability (Trypan Blue) assay and fluorescence microscopy utilizing fluorophores to Annexin V and Ethidium Homodimer III as well as morphological analyses. The results indicate that TCAP can protect cells from necrosis. In one aspect, TCAP has a neuroprotective role during times of cellular stress, such as induced pH stress. As such, TCAP can be used in the treatment of physiological effects of pH in the brain during trauma, such as hypoxia-ischemia.

In another aspect of the invention, TCAP was shown to enhance neurite length, β-tubulin and β-actin levels in neuronal cells and to enhance fasciculation of neuronal cells in cell culture or tissue. All these can contribute to TCAP's neuronal protective effects against death and to inhibit neuronal cell death. In another aspect, it illustrates the use of TCAP in the treatment neuronal conditions resulting from traumatic or epigenetically associated necrosis. In one aspect, TCAP can regulate neurite and axonal growth. In another aspect, it was shown that TCAP can alter interneuron communication via changes in neurite and axon outgrowth.

Definitions

"Administering to the cell(s)" as used herein means both in vitro and in vivo administration to the cells and can be direct or indirect administration, as long as the cells are at some point exposed to the substance being administered. In the case of a peptide, it can also include methods to increase expression of the peptide or peptides to enhance exposure of the desired target to said peptide.

"Apoptosis" as used herein means "programmed cell death" and is a necessary event of normal development. It is a normal process for eliminating unwanted cells.

"Effective Amount" and "Therapeutically Effective Amount" as used herein means an amount effective, at dosages and for periods of time necessary to achieve the desired results. For example, an effective amount of a substance may vary according to factors such as the disease state, age, sex, and weight of the individual, and the ability of the substance to elicit a desired response in the individual. Dosage regimes may be adjusted to provide the optimum therapeutic response. For example, several divided doses may be administered daily or the dose may be proportionally reduced as indicated by the exigencies of the therapeutic situation.

"Homeostasis" as used herein means the inherent tendency in an organism or cell toward maintenance of physiological stability and making automatic adjustments in relation to its environment. Other wise known as normal stability of the internal environment (Sapolsky, 1992).

"Inhibiting Neuronal Cell Death" as used herein include inhibiting, preventing, and protecting neuronal cells (including rescuing neuronal cells) from, cell death.

"Necrosis" as used herein means unprogrammed cell death induced by physiological trauma, such as hypoxia, injury, infection and cancer/carcinogenic agents.

"Neuronal Cells" as used herein includes immortalized mouse hypothalamic neurons.

"Obvious Chemical Equivalents" as used herein means, in the case of TCAP, any variant that does not have a material effect upon the way the invention works and would be known to a person skilled in the art. For instance, this could include but not necessarily be limited to any salts, esters, conjugated molecules comprising TCAP, truncations or additions to TCAP.

"Pharmaceutically Acceptable Carrier" as used herein means any medium which does not interfere with the effectiveness or activity of an active ingredient and which is not toxic to the hosts to which it is administered. It includes any carrier, excipient, or vehicle, which further includes diluents, binders, adhesives, lubricants, disintegrates, bulking agents, wetting or emulsifying agents, pH buffering agents, and miscellaneous materials such as absorbants that may be needed in order to prepare a particular composition. Examples of carriers, excipient or vehicles include but are not limited to saline, buffered saline, dextrose, water, glycerol, ethanol, and combinations thereof. The use of such media and agents for an active substance is well known in the art (e.g., "Remington: The Sciences and Practice of Pharmacy, $21^{st}$ Edition", (University of the Sciences in Philadelphia, 2005)

"Neuronal condition associated with alkaline neuronal cell pH" as used herein means any neuronal condition that is caused by or causes or results in or is associated with alkaline neuronal cell pH. Such conditions include, but are not limited to brain ischemia, neurodegenerative diseases such as, Alzheimer's, Parkinson's, Huntington's, brain ischemia and multiple sclerosis, and brain injury associated with physiological trauma.

"Stressor" is defined as anything that disrupts physiological balance, be it physical or psychological (Sapolsky, 1992)

"Stress-related brain or neuronal condition" as used herein means any brain neuronal condition associated with neuronal cells not being in a state of homeostasis.

"TCAP" as used herein means a 38-41 amino acid sequence, preferably a 40-41 amino acid sequence from the C-terminal end of a teneurin peptide and all analogs, homologs, fragments, derivatives, salts, esters of the TCAP peptide which have the desired activity, and obvious chemical equivalents thereto, as described in PCT/CA2003/000622. filed May 2, 2003, published Nov. 13, 2003, and which is herein incorporated by reference. For instance, in one embodiment, TCAP includes human or mouse TCAP, such as TCAP 1, such as SEQ. ID. NOs. 37-44 (mouse) or 69-76 (human) of PCT/CA2003/000622 and analogs, homologs, fragments, derivatives, salts, esters and obvious chemical equivalents thereof. In one embodiment the TCAP is mouse TCAP-1 having the amino acid sequence:

QQLLGTGRVQGYDGYFVLSVEQYLELSDSANNI-HFMRQSEI-NH2 (accession number nm 011855) (SEQ. ID. NO. 38).

In one embodiment TCAP is prepared by solid phase synthesis and stored as a lyophilized powder at −80° C. reconstituted by alkalinizing with ammonium hydroxide and dissolved into physiological saline at $10^{-4}$ M stock solution.

"A nucleotide encoding TCAP" as used herein means a nucleotide sequence that encodes TCAP, including DNA and RNA. Such suitable sequences are described in PCT/CA2003/000622, which is herein incorporated by reference.

Applications: The Use of TCAP to Inhibit Neuronal Cell Death

The invention broadly contemplates the use of TCAP, including an isolated TCAP, or a nucleotide encoding TCAP to inhibit neuronal cell death. In another aspect, the invention broadly contemplates the use of TCAP to increase fasciculation of neuronal cells in culture or in tissue, and in another aspect to increase β-tubulin and/or β-actin levels.

(a) Necrosis in Neurodegenerative Diseases

Necrotic cell death in the central nervous system follows acute ischemia or traumatic injury to the brain or spinal cord (Linnik, 1993; Emery, 1998). It occurs in areas that are most severely affected by abrupt biochemical collapse, which leads to the generation of free radicals and excitotoxins (e.g., glutamate, cytotoxic cytokines, and calcium). The histologic features of necrotic cell death are mitochondrial and nuclear swelling, dissolution of organelles, and condensation of chromatin around the nucleus. These events are followed by the rupture of nuclear and cytoplasmic membranes and the degradation of DNA by random enzymatic cuts in the molecule (Martin, 2001). Given these mechanisms and the rapidity with which the process occurs, necrotic cell death is extremely difficult to treat or prevent. The present inventors herein describe a method of treating and/or preventing necrotic cell death using TCAP.

(b) pH in Necrosis

According to Potapenko et al., brain alkalinization induces an increase of $Ca^{2+}$ in neurons due to $Ca^{2+}$ sequestering structures, such as the mitochondria and endoplasmic reticulum, and elevated cytoplasmic $Ca^{2+}$ is implicated in neuronal cell death, more specifically, necrosis during brain ischemia (Yuan et al., 2003). As mentioned previously such excessive rises in $Ca^{2+}$ may be induced by excitotoxicity caused by brain ischemia, subsequently over stimulating postsynaptic glutamate receptors; of these glutamate-gated channels, NMDA receptor channels play a key role in excitotoxicity as they conduct both $Na^+$ and $Ca^{2+}$ (Bonfoco et al. 1995).

(c) Brain Injuries Related to Alkalosis

Insults to the brain can quite often lead to shifts in pH and based on the data presented it appears that TCAP is rescuing neurons from necrosis consistently at high pH extremes, specifically pH 8.0 and 8.4. Dying neurons are a clear indication of many neurodegenerative diseases including Alzheimer's, Parkinson's, Huntington's, brain ischemia and multiple sclerosis (Siao, 2002). These neuro degenerative conditions are characterized by their deleterious effects on brain function resulting from deterioration of neurons. The destruction of neurons in these conditions may be regulated by various forms of cell death and can be caused by damaged mitochondrion, increased levels of excitotoxins such as glutamate, which increases calcium influx into the neurons and activates calcium dependent enzymes such as calpain and caspases (Randall & Thayer, 1992; Brorson et al., 1995) and pH. Brain pH during times of neurodegenerative stress is not well understood, however, calcium and pH are not mutually exclusive, during both respiratory and metabolic alkalosis, increases in calcium occur in rat neurons due to intracellular calcium accumulating structures such as the mitochondrion (Potapenko, 2004), this is also substantiated by the fact that glutamate induced neuron death requires mitochondrial calcium uptake (Stout et al., 1998).

Recent studies on brain energy metabolism using phosphorous and proton magnetic resonance (MR) spectroscopy have allowed an understanding of energy changes within the brain following (HI) (Thornton, 1998; Moon, 1973). A phenomenon named the "secondary energy failure" that occurs some 8-24 hours after the initial insult has been recently discovered, and have correlated the magnitude of this disruption with the eventual neurodevelopmental outcome (Thornton, 1998). A similar relationship between intracellular alkalosis and the severity of brain injury in infants has also found that babies with the most alkaline brain cells had more severe changes on MR imaging within the first 2 weeks of life and the worst neurodevelopmental outcome at one year (Robertson, 2002). Thus, a means of identifying neuropeptides with pH protective properties would be a pivotal finding as it would provide novel therapeutic treatments. The inventors have shown herein that TCAP is a neuroprotective peptide and can inhibit neuronal cell death. As such, it can be used to treat a number of neuronal conditions, such as a neuronal condition associated with alkaline neuronal cell pH.

(d) Neuronal Cell Death Inhibition/Neuroprotective Role of TCAP During Times of Stress The potential for neuropeptides to regulate brain processes during times of stress (e.g. as a result of a stress-related brain or neuronal condition) is an important paradigm in the search for novel ways of coping with neurodegenerative diseases and physiological stress and examples of neuropeptides being connected with therapeutic uses are plentiful. (Gozes et al., 1994; Glazer et al. 1994; Zhang et al., 2001) The teneurin C-terminus associated peptides (TCAP) have a neuroprotective effect from cell death, during times of pH induced cellular stress in the brain such as during hypoxia-ischemia. The present inventors herein describe a method of treatment or use of TCAP in the treatment of such stress-related brain or neuronal conditions and the use of TCAP in the preparation of a medicament for the treatment of such conditions.

(e) Screening for Potential Modulators of TCAP Inhibition of Neuronal Cell Death.

In on embodiment, the invention provides a method for screening compounds that modulate TCAP inhibition of neuronal cell death, comprising, administering TCAP to neuronal cells under conditions that promote inhibition of neuronal cell death in the presence of a potential TCAP modulator and monitoring the affects of said potential modulator on the viability of the neuronal cells. In one embodiment, this can be done in comparison to a control, such as the potential modulator with or without TCAP and/or with TCAP but no potential modulator. In one aspect of the invention the administration of TCAP can occur in a number of ways including, but not necessarily limited to: administering the TCAP in a suitable form of peptide to the cells, administering a substance that will enhance TCAP expression and availability of TCAP to the cell; administration of a nucleic acid encoding TCAP that will result in enhanced TCAP expression to the cell.

(f) The Use of TCAP to Regulate Neurite Growth—TCAP as a Neuroplastic Agent

In one embodiment of the invention, TCAP alters interneuron communication via changes in neurite and axon outgrowth. Synthetic mouse/rat TCAP-1 was used to treat cultured immortalized mouse hypothalamic cells to determine if TCAP-1 could directly regulate neurite and axon growth. TCAP-1 treated cells showed a significant increase in the length of neurites, accompanied by a marked increase in β-tubulin transcription and translation as determined by real-time PCR and western blot analysis, respectively, although changes in α-actinin 4 transcription and β-actin translation were also noted. Immunofluorescence confocal microscopy using β-tubulin antisera showed enhanced resolution of β-tubulin cytoskeletal elements throughout the cell. In order to determine if the effects of TCAP-1 could be reproduced in primary neuronal cultures, primary cultures of day E18 rat hippocampal cells were treated with 100 nM TCAP-1. The TCAP-1 treated hippocampal cultures showed a significant increase in both the number of cells and the presence of large and fasciculated β-tubulin immunoreactive axons. The data indicates the TCAP acts as a functional region of the teneurins to regulate neurite and axonal growth of neurons.

It is also herein shown that TCAP-1 increases neurite length and alters the levels and distribution of key cytoskeletal proteins and genes associated with axon outgrowth in immortalized neuronal cell lines. Moreover, because both TCAP-1 expression (Wang et al., 2005) and teneurin-1 (Zhou et al., 2003) expression is high in hippocampal cells the effects of TCAP-1 was studied on primary cultures of hippocampal cells. In these cultures TCAP-1 dramatically increased the incidence of axon formation, e.g. in primary cultures of hippocampal cells. The TCAP/teneurin system represents a new mechanism in neuroplasticity.

This has implications in the treatment of certain conditions and inducing changes in the brain, such as changes in acoustic startle response, learning, memory, anxiety or other brain or neuronal conditions. TCAP can be used to treat such conditions.

One can screen for modulators of TCAP, neurite growth or neuroplasticity, by administering the suspected modulator to a neuron or neurons or tissue comprising neurons in the presence of TCAP under conditions that promote neurite growth or neuroplasticity and monitoring the effects of the suspected modulator on said activities. The effect can be compared to a control, such as known baseline levels of activity, or a control such as in the presence or absence of TCAP and/or the suspected modulator. In one embodiment, a modulator can enhance the effects of TCAP. In another embodiment, the modulator can diminish the effects of TCAP.

Pharmaceutical Compositions and Modes of Administration

TCAP, pharmaceutically acceptable salts or esters thereof or obvious chemical equivalents thereof can be administered by any means that produce contact of said active agent with the agent's sites of action in the body of a subject or patient to produce a therapeutic effect, in particular a beneficial effect, in particular a sustained beneficial effect. The active ingredients can be administered simultaneously or sequentially and in any order at different points in time to provide the desired beneficial effects. A compound and composition, of the invention can be formulated for sustained release, for delivery locally or systemically. It lies with the capability of a skilled physician or veterinarian to select a form and route of administration that optimizes the effects of the compositions and treatments of the present invention to provide therapeutic effects, in particular beneficial effects, more particularly sustained beneficial effects.

In one embodiment, administration of TCAP includes any mode that produce contact of said active agent with the agent's sites of action in vitro or in the body of a subject or patient to produce the desired or therapeutic effect, as the case may be. As such it includes administration of the peptide to the site of action—directly or through a mode of delivery (e.g. sustained release formulations, delivery vehicles that result in site directed delivery of the peptide to a particular cell or site in the body. It also includes administration of a substance that enhances TCAP expression and leads to delivery of TCAP to a desired cell or site in the body. This would include but is not limited to the use of an oligonucleotide encoding TCAP, e.g. via gene therapy or through a TCAP expression system in vitro or in vivo, as the case may be that results in enhanced expression of TCAP. It can also include administration of a substance to the cell or body that enhances TCAP levels at the desired site.

The above described substances including TCAP and nucleic acids encoding TCAP or other substances that enhance TCAP expression may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals.

Thus in one embodiment, the invention provides the use of TCAP or modulator thereof in the preparation of a medicament for the inhibition of neuronal cell death and/or the treatment of related conditions. In one embodiment, a therapeutically effective amount of TCAP or a pharmaceutical composition as described herein is administered to a patient in need thereof. A patient in need thereof is any animal, in one embodiment a human, that may benefit from TCAP and its effect on inhibition of neuronal cell death or increase neuronal growth, β-tubulin or β-actin levels, increase in fasciculation or as a guidance molecule.

An active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions that may inactivate the compound. In one embodiment, TCAP is administered directly to or proximate to the desired site of action, by injection or by intravenous. If the active substance is a nucleic acid encoding, for example, a TCAP peptide it may be delivered using techniques known in the art.

The compositions described herein can be prepared by per se known methods for the preparation of pharmaceutical acceptable compositions which can be administered to subjects, such that an effective quantity of the active substance is combined in a mixture with a pharmaceutical acceptable vehicle or carrier. Suitable vehicles or carriers are described, for example, in Remington's Pharmaceutical Sciences (Remington's Pharmaceutical Sciences, Mack Publishing Company, Easton, Pa., USA 1985 or Remington's The Sciences and Practice of Pharmacy, $21^{st}$ Edition", (University of the Sciences in Philadelphia, 2005) or Handbook of Pharmaceutical Additives (compiled by Michael and Irene Ash, Gower Publishing Limited, Aldershot, England (1995)). On this basis, the compositions include, albeit not exclusively, solutions of the substances in association with one or more pharmaceutical acceptable vehicles, carriers or diluents, and may be contained in buffered solutions with a suitable pH and/or be iso-osmotic with physiological fluids. In this regard, reference can be made to U.S. Pat. No. 5,843,456.

As will also be appreciated by those skilled, administration of substances described herein may be by an inactive viral carrier. In one embodiment TCAP can be administered in a vehicle comprising saline and acetic acid.

Further, in one embodiment, TCAP may be administered in a form that is conjugated to another peptide to facilitate delivery to a desired site, or in a vehicle, eg. a liposome or other vehicle or carrier for delivery. For instance, in one embodiment TCAP can be conjugated to a brain targeting vector, which is a peptide or peptidomimetic monoclonal antibody (MAb), that is transported into brain from blood via an endogenous blood brain barrier (bBB) transport system, which has shown to significantly reduce stroke volume (e.g. see Zhang et al. (2001)). Thus, in one embodiment, brain ischemia can be treated by neuropeptides, such as TCAP, with noninvasive intravenous administration. In one embodiment, the peptide is conjugated to a BBB drug targeting system such as transferrin, for example as described in Vuisser et al. (2004) or Kang et al. (1994). In another embodiment, TCAP does not require a transport mechanism to cross the blood brain barrier.

The present invention is described in the following Examples, which are set forth to aid in the understanding of the invention, and should not be construed to limit in any way the scope of the invention as defined in the claims which follow thereafter.

EXAMPLES

Example 1—Peptide Synthesis

Mouse TCAP-1 (i.e., SEQ. ID. NO. 38) was prepared by solid phase synthesis as previously described (Qian et al., 2004). The peptide was solubilized in phosphate buffered saline (PBS) at a concentration of $2 \times 10^{-7}$ M before being diluted in the appropriate medium.

More particularly, a mouse paralogue of the putative peptide sequence from teneurin-1 was synthesized on an automated peptide synthesizer, Model Novayn Crystal (NovaBiochem, UK Ltd., Nottingham, UK) on PEG-PS resin using continuous flow Fmoc chemistry (Calbiochem-Novabiochem Group, San Diego, Calif.). Eight times excess diisopropyl ethylamine (Sigma-Aldrich Canada Ltd.) and four times excess Fmoc-amino acid activated with HATU (O-(7-azabenzotriazol)-1-3,3-tetramethyluronium hexyluorophosphate; Applied Biosystems, Foster City, Calif.) at a 1:1 (mol/mol) ratio were used during the coupling reaction. The reaction time was 1 h. A solution of 20% piperidine (Sigma-Aldrich Canada Ltd.) in N,N-dimethylformide (DMF; Caledon Laboratories Ltd., Canada) was used for the deprotection step in the synthesis cycle. The DMF was purified in-house and used fresh each time as a solvent for the synthesis. The cleavage/deprotection of the final peptide was carried out with trifluoroacetic acid (TFA), thioanisole, 1,2 ethandithiol, m-cresole, triisopropylsilane, and bromotrimethyl silane (Sigma-Aldrich Canada Ltd.) at a ratio of 40:10:5:1:1:5. Finally, it was desalted on a Sephadex G-10 column using aqueous 0.1% TFA solution and lyophilized. The peptide was solubilized by exposure to ammonium hydroxide vapors for 2 minutes before dilution in phosphate-buffered saline (PBS) pH 7.4 with 10 nM sodium phosphate.

Example 2—Cell Morphology Analysis

The effect of TCAP-1 on cell morphology was conducted using the N38 cells immortalized mouse hypothalamic cell line (Belsham et al, 2004). Cells were grown in six-well culture plate with 2 ml of Dulbeco's Modified Eagle Medium (DMEM) with high glucose, L-glutamate, 25 mM HEPES buffer, pyridoxine hydrochloride in the absence of sodium pyruvate, 5 ml penicillin with 10% fetal bovine serum (FBS) at pH 7.4 (all from Gibco-Invitrogen, Burlington, Canada).

At 24 and 48 hrs, the medium was replaced with medium buffered at pH 6.8, 7.4, 8.0 or 8.4. Half of the cell groups received ($10^{-7}$M) TCAP-1, whereas the other half received phosphate buffered saline (PBS) pH 7.4 containing 8 g NaCl, 0.2 g KCl, 1.4 g $Na_2HPO_4$, 0.2 g $KH_2PO_4$ in 800 mL $ddH_2O$. For all groups, 4 replicates were run. Digital pictures were taken at 24, 48 and 72 hrs using an Olympus IX&1 inverted microscope at magnification and analyzed using Lab Works 4.0 Image Acquisition and Analysis Software (Ultraviolet Products Ltd., CA)

Results

TCAP did not induce any observable morphological changes in the cells cultured at pH 7.4. However, there was significant increase in the number of small round cell types (necrotic cells) in the vehicle-treated cultures at pH 6.8 ($p<0.05$), 8.0 ($p<0.001$) and 8.4 ($p<0.001$) as compared to the TCAP-treated samples at 48 hrs (F=96.16). At 72 hrs, TCAP significantly decreased the number of rounded cells in pH 8.0 ($p<0.001$) and pH 8.4 ($p<0.001$) (F=51.13) relative to the vehicle-treated cells. (FIGS. 1A-1D).

Example 3—Effect of TCAP on Cell Proliferation and Viability

The effect of TCAP-1 on cell proliferation at each pH was examined by direct counts using a hemocytometer and indirectly by assessing mitochondrial activity using a colorimetric MTT (3-[4,5-dimethylthiazol-2-yl]-2,5-diphenyl tetrazolium bromide) assay on cultured N38 cells. For hemocytometer counts, the cultures were incubated for 24 and 48 hrs. The cells were suspended using 1 ml of 0.25% Trypsin with EDTA (Gibco-Invitrogen, Burlington, Canada), centrifuged at 1600 RPM for 4 min, and resuspended with PBS. The cells in 50 µl aliquots were vortexed and counted on a hemocytometer.

The proportion of viable cells in the samples was determined by measuring Trypan Blue uptake. At 48 hrs, the cells from the four pH treatments were suspended using 1 ml of Trypsin EDTA, centrifuged at 1600 RPM for 4 min and resuspended in 1 ml of BSS (Hank's Balanced Salt Solution) (Sigma, St. Louis). An aliquot of 0.5 ml of 0.04% Trypan Blue solution was transferred to a 1.5 ml tube, 0.03 ml of BSS was added to 0.2 ml of the cell suspension; the samples were mixed thoroughly and the cell suspension-Trypan Blue mixture was allowed to stand for 10 minutes and then counted on a hemocytometer. Separate counts were kept for both viable and non viable cells.

A (3-4,5-dimethylthiazol-2-yl]-2,5-diphenyl tetrazolium bromide) MTT assay was conducted using the In Vitro Toxicology Assay Kit: MIT based (Sigma, St. Louis). The cells were cultured for the MTT assay at 24 and 48 hours and were incubated at 37° C. in 5% $CO_2$ for 3 hrs in the presence of MTT 200 µl/2 ml medium. The samples were mixed by shaking the plate horizontally for 30 min. The background absorbance of the multi-well plates was determined at 690 nm and subtracted from the 570 nm measurement.

Results

There were no significant differences in the total number of cells, as determined by direct hemocytometer counts, between the vehicle- and TCAP-treated cells at 24 hrs under any pH condition (FIG. 2A). There was a marked reduction in the number of total cells at pH 8.0 and 8.4 in the vehicle-treated cells at both 24 and 48 hrs. However, TCAP inhibited the decrease in total cell numbers relative to the vehicle-treated cells at pH 6.8 ($P<0.001$) 8.0 ($P<0.001$) and 8.4 ($P<0.01$) (F=38.10) after 48 hrs of incubation.

A Trypan Blue stain was conducted in order to estimate the proportion of viable cells in a population (FIG. 2B). TCAP-1 treatment caused a significant decrease in the number of cells that took up the trypan blue stain at 48 hrs in cells cultured at pH 6.8 ($p<0.05$), pH 8.0 ($p<0.0001$) and at pH 8.4 ($p<0.001$) ($F=58.27$) but not pH 7.4. Although TCAP did not induce a significant effect on MTT activity at pH 7.4 or pH 6.8 there was a significant increase in optical density at 48 hrs in TCAP-1-treated samples cultured in pH 8.0 ($p<0.01$) and pH 8.4 ($p<0.001$) ($F=21.19$) (FIG. 3).

Example 4—Fluorescent Microscopy of Necrosis and Apoptosis Markers

N38 cells were cultured on poly-D-Lysine treated coverslips (VWR, Mississauga) in each of the four pH condition, and cells were washed twice with PBS, each fluorochrome was added to each well: 5 µl Fluorescein (FITC)-Annexin V in Tris EDTA buffer containing 0.1% BSA (Bovine serum albumin) and 0.1% NaN3, pH 7.5, 5 µl rhodamine EtD-III 200 µM in PBS and 5 µl 4',6-Diamidino-2-phenylindole (DAPI) Hoechst 33342 5 µg/mL in PBS (Biotium, Inc. Hayward). The samples were incubated in the dark for 15 min, then washed before being placed on slides. The cells were viewed under a LEICA DM 4500 inverted fluorescent microscope and digitally analyzed using OpenLab software.
Results Annexin V labelled with fluorescein (FITC) was used to identify apoptotic cells in green. Ethidium homodimer III (EtD-III) is a positively charged nucleic acid probe, which is impermeable to live or apoptotic cells but stains necrotic cells with red fluorescence (rhodamine) and Hoechst 3342 (4',6-Diamidino-2-phenylindole (DAPI) emits bright blue fluorescence upon binding to DNA in living cells.

Figure 4A:
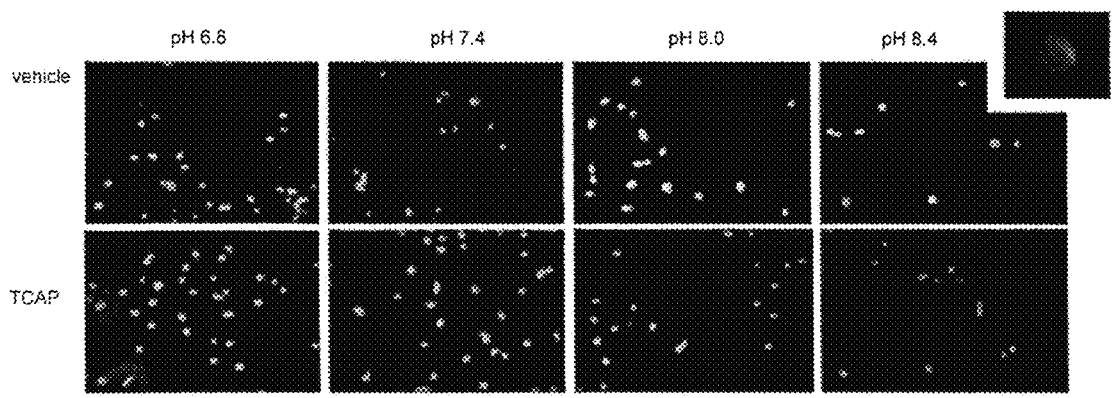
FIG. 4A. Apoptotic, necrotic and healthy cells fluorescent microscopy quantification analyses post 48 hrs. Cell types are characterized by colour: apoptosis (green) necrosis (red) healthy (blue).
Figure 4B:
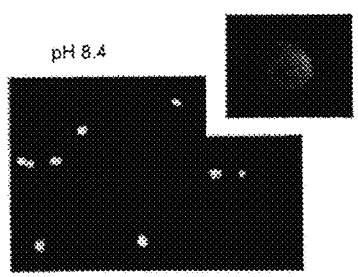
FIG. 4B. Example of apoptotic cell.
Figure 4C:
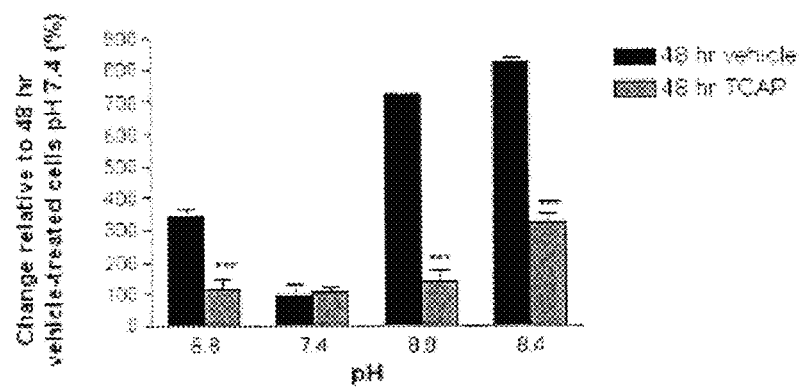
FIG. 4C. Apoptotic, necrotic and healthy cells fluorescent microscopy quantification analyses. TCAP significantly decreased the amount of necrotic cells post 48 hrs at pH extremes 6.8 ($P<0.0001$), 8.0 ($P<0.0001$), 8.4 ($P<0.0001$). A two way ANOVA was used to determine levels of significance.

TCAP-1 decreased the number of rhodamine-fluorescing cells at pH 6.8 ($p<0.001$), 8.0 ($p<0.001$) and 8.4 ($p<0.001$) ($F=348.2$) but not in the pH 7.4 samples (FIGS. 4A and 4C). There were nominal amounts of FITC-labelled cells located intermittently throughout samples where only a total of 3 green cells were counted (see inset, FIG. 4B and inset).

Summary of Examples 3 and 4—Necrosis

Necrosis occurs when cells are exposed to extreme variance from physiological conditions such as hypothermia and hypoxia, which may result in damage to the plasma membrane (Majno and Jorris, 1995). Necrosis begins with an impairment of the cell's ability to maintain homeostasis, leading to an influx of water and extracellular ions. Intracellular organelles, most notably the mitochondria, and the entire cell swell and rupture (cell lysis) (Linnik et al, 1993). Due to the ultimate degeneration of the plasma membrane, the cytoplasmic contents including lysosomal enzymes are released into the extracellular fluid. Therefore, in vivo, necrotic cell death is often associated with extensive tissue damage resulting in an intense inflammatory response (Emery et al, 1993). Necrosis was determined as the form of cell death occurring based on expected morphological alterations affecting the plasma membrane including massive production of small surface evaginations (bubbles) caused by the cells inability to control water influx through the plasma membrane (Rello et al., 2005). The Trypan Blue Stain (Example 3) is based on an acid dye that contains two azo chromophores. The reactivity of this dye is dependent on the negatively charged chromophore binding to cytoplasmic material when the membrane is damaged. Staining facilitates the visualization of cell morphology since it is only the dead cells that take up the dye, thus identifying cells that are necrotic or are in the very late stages of apoptosis. The fluorescent microscopy study (Example 4) also solidifies this assumption as TCAP decreases the number of necrotic cells and not apoptotic cells. These findings are significant as necrosis plays an integral role in neurodegenerative diseases.

Example 5—Apoptosis (Caspase and PARP) Markers

Apoptosis, otherwise known as "programmed cell death" is a necessary event of normal development. The apoptotic pathway is mediated by a family of death proteins, caspases, These signaling proteins are proteolytic enzymes that when inactive, lay dormant as zymogens until they are activated by various triggers (Hengartner, 2000). Upon activation of caspase 3 certain nuclear proteins are cleaved such as Poly ADP-ribose polymerase (PARP). PARP, a 116 kDa nuclear polymerase, is involved in DNA repair usually in response to environmental stress (Hengartner, 2000; Willie, 1980; Kerr, 1972). The protein can be cleaved by many interleukin-converting enzyme-like (ICE-like) proteases (Willie, 1980; Liu, 1997). (PARP) was one of the first proteins reported to be cleaved during apoptosis, and is a target of the Yama/CPP32 protease, caspase-3 (Kaufmann, 1989; Kaufman et al, 1993). Cleavage products occurring due to apoptosis result in western blot bands at 89 KDa. The following experiments were conducted to determine whether TCAP works through the apoptotic pathway.
(a) Colorimetric Caspase Assays Caspase 8 and 3 colorimetric assays were performed on the N38 cells at all pH conditions. The assay was based on the detection of the chromophore pNA after cleavage from the labeled substrate IETD-pNA and DEVD-pNA for caspase 8 and 3, respectively. Comparison of the pNA absorbance from the suspected apoptotic sample was compared to the uninduced neutral pH sample. Caspase 8 and 3 were analysed using the Caspase-3 Colorimetric Activity Assay (Chemicon, Temecula USA) and Caspase-8 Colorimetric Activity Assay (Chemicon, Temecula USA). The cells from each pH treatment described previously at 24 and 48 hrs were removed using a cell scraper and centrifuged at 1500 rpm for 10 minutes. The cells were resuspended in 350 µl of chilled cell lysis buffer containing 500 µl PBS, 5 µl 1% Triton ×100 (Sigma, St. Louis), 25 µl proteinase inhibitor cocktail set III (VWR, Mississauga), 0.5 µl 1M dithiothreitol (DTT) (Sigma, St. Louis) and 2.5 µl phenylmethylsulphonylfluoride (PMSF) diluted in 1 mL of methanol (EM Science, Gibbstown), then incubated on ice for 10 min and centrifuged for 5 minutes at 10,000 rpm. The supernatant, consisting of cytosolic extracts, was transferred to a new tube and a bicinchoninic acid (BCA) protein assay (Pierce, Rockford) was conducted to determine total protein concentration. The absorbance of each sample was measured on a SPECTRAmax Microplate spectrophotometer at 405 nm after an incubation period of 2 hours at 37° C. Changes in caspase 3 activity were determined by comparing the absorbance reading from the induced sample with the level of the uninduced control. Background readings from the buffer were subtracted from the reading of both the induced (pH 6.8, 8.0, 8.4) and uninduced (pH 7.4) samples before calculating changes in caspase 3 activity. The same was done for the detection of caspase 8. As a control, N38 cells were cultured with pH 7.4 DMEM and incubated for 4 days, apoptosis was then induced using 10 µM/ml etoposide and lysed according to the above protocol and used a control for all subsequent caspase 3 detection. All assays were performed with 4 replications.

(b) Caspase 3 and Poly(ADP-Ribose)Polymerase (PARP) Cleavage by Immunoblot

Detection of caspase 3 cleavage was determined at 48 hrs. The samples at each pH and control (see above) were lysed using total protein isolation lysis buffer (described above). An aliquot of 25 µl of each sample was combined with 25 µl of 2×20% sodium dodecyl sulphate (SDS) sample buffer and loaded onto a 4-10% HCL-Tris pre cast polyacrylamide gel (BioRad, Mississauga). The gel was run at 200 v for 35 min and proteins were electrotransfered to a Hybond-C nitrocellulose membrane (Amersham, Baie d'Urfé) for 75 min at 100 v. After transfer, the membrane was washed with 10 ml of PBS with 0.05% Tween 20 (PBST) for 5 min at room temperature (RT) and the membrane was incubated in 10 ml of PBST-milk for one hour at RT followed by 3 times for 5 min washes with 10 ml of PBST. The membrane was then incubated with cleaved caspase 3 primary antiserum (Cell Signaling Technology, Beverly) at a titre of 1:500 in 6 ml of PBST-milk with gentle agitation overnight at 4° C. The membranes were washed 3 times for 5 min with 10 ml of PBST followed by membrane incubation with anti-rabbit horseradish peroxidase (HRP)-conjugated secondary antibody (Amersham, Baie d'Urfé) at 1:3000 in 6 ml of PBST-milk with gentle agitation for 1 hr at RT. The membranes were then washed 3 times for 5 min with 10 ml of PBST then exposed to Kodak X-OMAT Blue scientific imaging film (Perkin Elmer Canada Inc, Vaudreuil-Dorion) for 30 min.

Using the same protocol, changes in PARP expression were determined at 48 hrs. The membrane was incubated with PARP primary antibody (Cell Signaling Technology, Beverly) at a titre of 1:100. The membranes were washed 3 times for 5 min with 10 ml of PB ST followed by membrane incubation with anti-rabbit horseradish peroxidase (HRP)-conjugated secondary antibody (Amersham, Baie d'Urfé) at 1:3000 in 6 ml of PBST-milk with gentle agitation for 1 hr at RT. The membranes were then washed 3 times for 5 min with 10 ml of PBST then exposed to Kodak X-OMAT Blue scientific imaging film (Perkin Elmer Canada Inc, Vaudreuil-Dorion) for 30 min. Total optical density of the blots, were quantified using LabWorks 4.0 Image Acquisition and Analysis Software from Ultra-Violet Products Ltd. (UVP).

Results

Figure 5A:
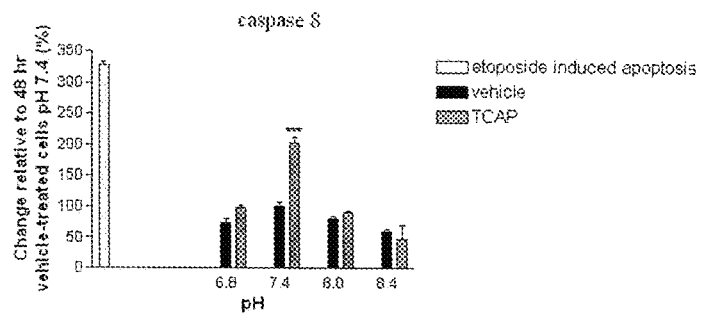
FIG. 5A. Caspase 8 colorimetric assay at pH extremes.
Figure 5B:
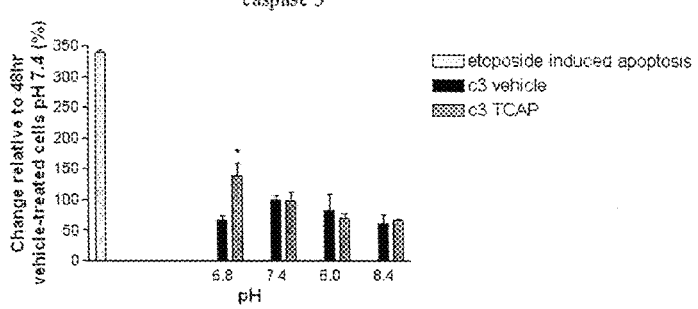
FIG. 5B. Caspase 3 colorimetric assay at pH extremes.
Figure 5C:
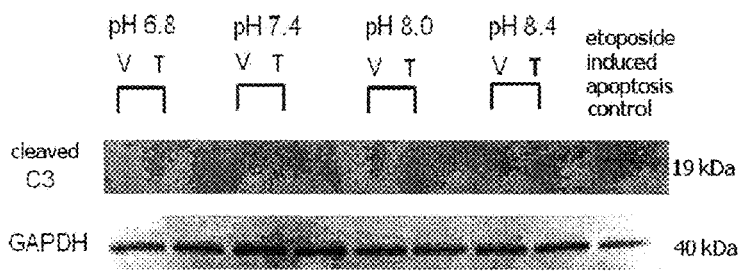
FIG. 5C. Caspase 3 western blot.

Etoposide was used to determine the amount of caspase 8 (FIG. 5A) and 3 (FIG. 5B) activation under apoptotic conditions. Etoposide induced a greater than 3-fold increase in caspase 8 and 3.5-fold increase in caspase-3 relative to the vehicle-treated cells at pH 7.4. Although TCAP-1 increased caspase 8 activity in pH 7.4 samples (P<0.001) (F=20.80) and increased caspase 3 activity in pH 6.8 samples (P<0.05) (F=2.117), the relative level of caspase activity was about 70% and 40% of the etoposide-induced increase for caspase 8 and 3 respectively. There were no significant differences in caspase 8 and 3 activity between the TCAP-1- and vehicle-treated cells at pH 8.0 and 8.4. As a further determination of caspase 3 activity, four replicates of western blots were conducted on pH treated N38 cells at the 48 hr mark in order to detect the cleaved and activated caspase 3 (17/19 kDa) (FIG. 5C). The caspase 3 cleavage product was clearly visible in the protein extracts of the etoposide-treated cell but could not be observed in any of the TCAP-1 or vehicle-treated cells at any of the pH conditions.

Figure 6A:
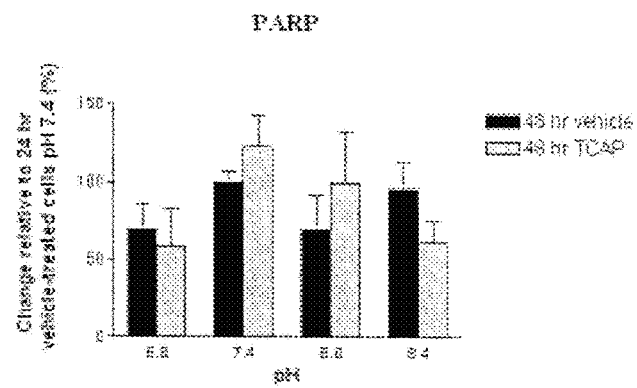
FIG. 6A. PARP quantification using transformed data.
Figure 6B:
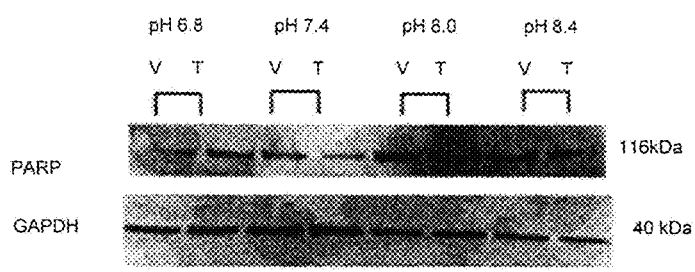
FIG. 6B. PARP western blot detection at pH extremes. Post 48 hrs TCAP-1 ($10^{-7}$M).
Figure 6C:
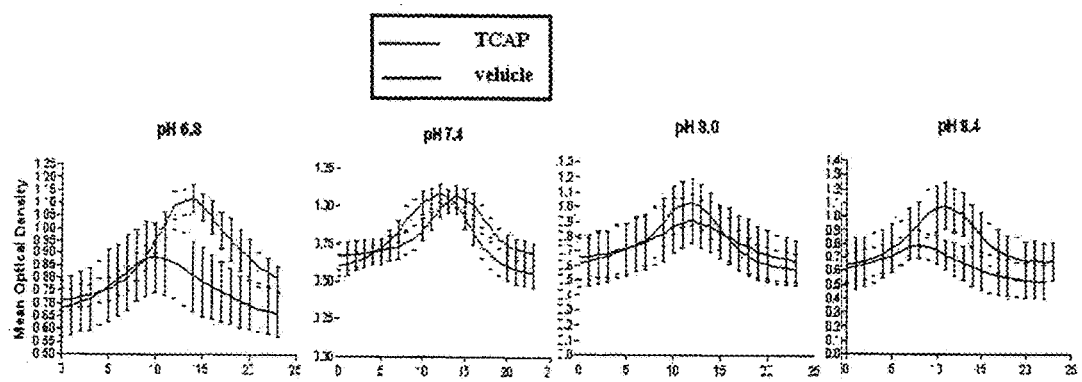
FIG. 6C PARP optical density quantification.

Four replicates of western blots were conducted on pH treated N38 cells at the 48 hour mark in order to detect endogenous levels of full length PARP, as well as the large fragment (89 kDa) and small fragment (24 kDa) of PARP resulting from caspase cleavage. The western blot (FIG. 6B) revealed endogenous PARP at all pH treatments as well as vehicles samples and based on a two way ANOVA using Bonferroni's Post Test, there were no significant differences between vehicle and TCAP treated samples (FIGS. 6A and 6C).

Based on the studies conducted and described in Example 5, TCAP is not protecting neuronal cells by inhibiting the apoptotic pathway.

Example 6—Kinase B/Akt Cell Survival Pathway

Protein kinase B or Akt (PKB/Akt) is a serine/threonine kinase, which functions to promote cell survival by inhibiting apoptosis by means of its ability to phosphorylate and inactivate several targets including BAD and forkhead transcription factors (Crowder, 1998). AKT, also referred to as PKB or Rac, plays a critical role in controlling the balance between cell survival and cell death in neurons (Dudek, 1997). The present example was conducted to determine whether TCP acts through this particular survival pathway.

Western blots using Akt and phosphorylated Akt (P-Akt) primary antibodies were conducted on all conditions of the cultured N38 cells to determine whether TCAP was preventing cell death by phosphorylation. The same western blot procedure outlined above was repeated with an Akt primary antibody (Cell Signalling, Beverly) at a titer of 1:500, followed by membrane incubation with anti-rabbit HRP-conjugated secondary antibody (Amersham, Baie d'Urfé) at 1:3000, followed by exposure on Kodak X-OMAT Blue film (Perkin Elmer Canada Inc, Vaudreuil-Dorion) for 30 min. Phospho Akt expression at 48 hrs was determined using the method described above with a PAkt primary antibody (Cell Signalling 9271) at 1:1000 followed by membrane incubation with anti-rabbit HRP-conjugated secondary antibody (Amersham, Baie d'Urfé) at 1:2000 followed by exposure on Kodak X-OMAT Blue film (Perkin Elmer Canada Inc, Vaudreuil-Dorion) overnight. Cultured N38 cells were serum-starved for 48 hours in order to induce phosphorylation and following the same protocol above were loaded as a control. Total optical density of the blots, were quantified using LabWorks 4.0 Image Acquisition and Analysis Software from Ultra-Violet Products Ltd. (UVP).

Results

Figure 7A:
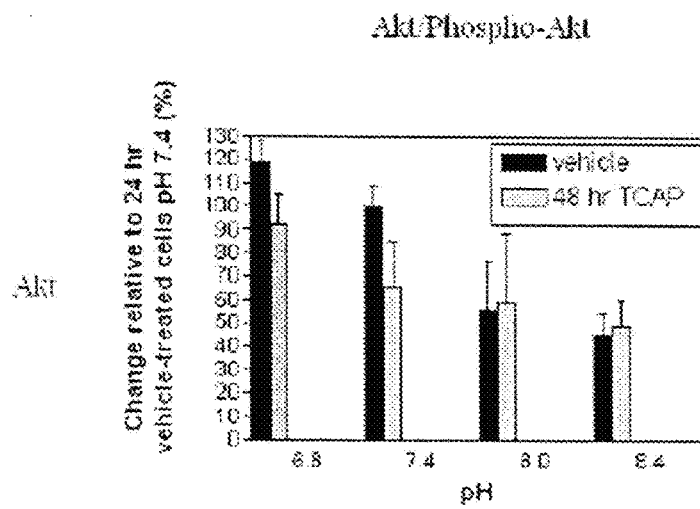
FIG. 7A. Akt quantification using transformed data.
Figure 7B:
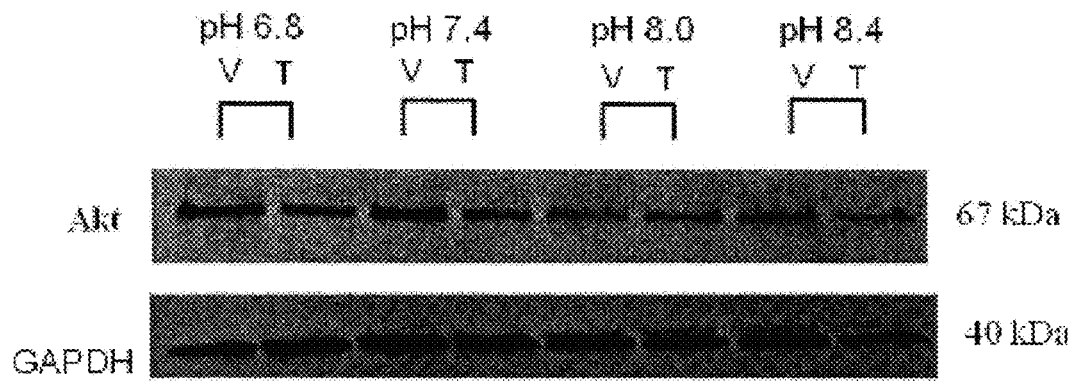
FIG. 7B. Akt western blot detection at pH extremes. Post 48 hrs TCAP-1 ($10^{-7}$M).

Western blots were conducted using an Akt antibody, which detected total levels of endogenous Akt (FIG. 7B). The blot revealed endogenous Akt in all treatments as well as the vehicle, however according to a two way ANOVA using Bonferroni's Post Test, there appears to be no difference in endogenous Akt between vehicle and TCAP treated samples (FIG. 7A). Total optical density of the blots were quantified using LabWorks 4.0 Image Acquisition and Analysis Software from Ultra-Violet Products Ltd. (UVP).

Figure 7C:
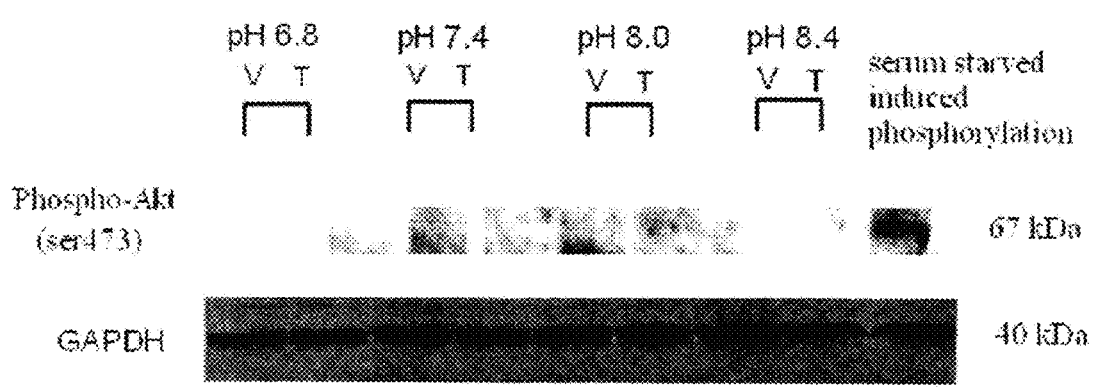
FIG. 7C. Phospho-Akt western blot detection at pH extremes. There was no indication of AKT phosphorylation in any sample except for the control, thus TCAP is not rescuing cells through the AKT cell survival pathway.

Western blots were conducted using a Phospho-Akt antibody, which detected total levels of endogenous Akt1 only when phosphorylated at serine 473. The blot revealed no bands in any samples, thus phosphylation of Akt is not occurring. Phsophorylation of cells was induced by serum starvation and loaded as a control, the blot revealed a band, however no other bands were detected (FIG. 7C).

Example 7—The Effect of TCAP on Cell Cycling: Bromodeoxyuridine (BrdU) Incorporation Assay The evaluation of cell cycle progression is important when assessing the viability of a cell population. The cell cycle is a sequence of stages that a cell passes through between one division and the next. The cell cycle oscillates between mitosis and the interphase, which is divided into G, S, and G 2. In the G phase there is a high rate of biosynthesis and growth; in the S phase there is the doubling of the DNA content as a consequence of chromosome replication; in the G 2 phase the final preparations for cell division (cytokinesis) are made (Raza, 1985). In order to determine whether TCAP was increasing cell cycle efficiency, a bromodeoxyuridine (BrdU) non-isotopic enzyme immunoassay was conducted (Calbiochem, Canada). BrdU incorporation into newly synthesized DNA of actively proliferating cells enables one to quantify cell cycle progression and the population of cells entering the S phase (Gratzner, 1982; Raza, 1985).

N38 cells were grown in a 96-well culture plate using 100 µl at an initial density of $2 \times 10^5$ cells/ml. Controls consisted of a blank, one well containing only DMEM with no cells and background, and one well with cells but with no BrdU label added. A working stock of BrdU was prepared by diluting the BrdU label 1:2000 into fresh DMEM, 20 µl of the working stock was added to each well to be labelled, the BrdU was allowed to incubate with the cells for 2 hrs at 37° C. The contents of the wells were then removed and 200 µl of the enclosed Fixative/Dentauring solution was added to each well and incubated for 30 min at Room Temperature (RT). The contents of the wells were removed and Anti-BrdU Antibody (1:100) was added to each well and incubated for 1 hr at RT. Wells were washed 3 times with wash buffer, the plate was then gently blotted on paper towel. The conjugate was prepared by diluting the reconstituted in (1×PBS) peroxidase goat anti-Mouse IgG HRP conjugate in the enclosed conjugate diluent and loaded onto a syringe filter through 0.2 µm filter and a 100 µl aliquot of this solution was transferred to each well and incubated for 30 min at RT. The wells were washed with wash buffer, the entire plate was then flooded with double deonized water and the contents of the wells were removed. An aliquot of 100 µl of BrdU substrate solution was added to each well, the plate was then incubated in the dark at RT for 15 min. 100 µl of stop solution containing 2.5N sulphuric acid was added to each well in the same order as the previously added substrate solution. Absorbance was measured on a SPECTRAmax Microplate spectrophotometer at dual wavelengths at 450-540 nm.

Results

Figure 8:
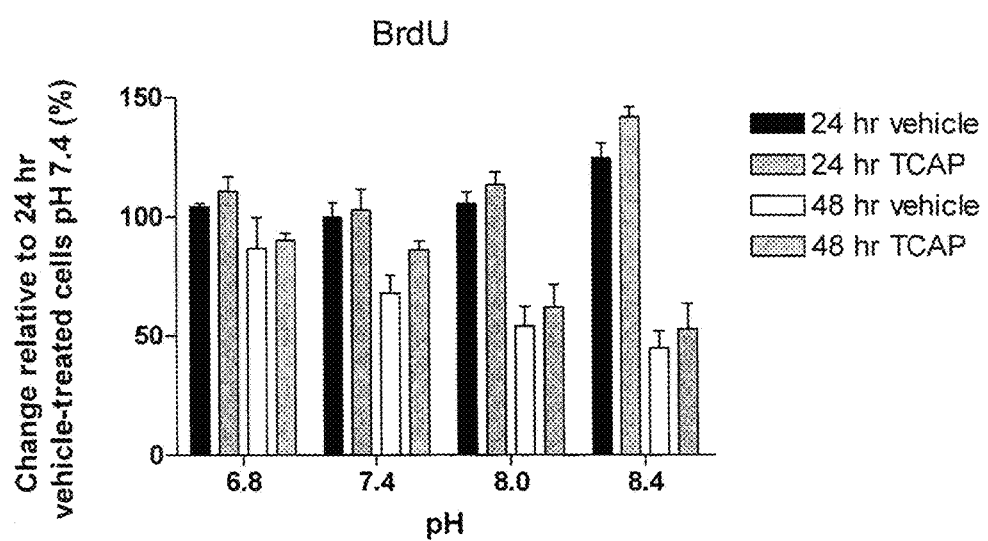
FIG. 8. BrdU colorimetric assay at pH extremes.

Based on a two way ANOVA using Bonferroni's Post Test there were no significant results at 24 or 48 hrs (FIG. 8).

This investigation indicates that synthetic TCAP-1 has a neuroprotective effect on immortalized hypothalamic mouse cells. The data described in this study suggest a significant neuroprotective role for TCAP during times of pH induced cellular stress. Several lines of evidence point to this. Based on haemocytometer counts and an MTT assay conducted on pH stressed N38 cell samples, TCAP has a positive affect on cell viability during pH induced cellular stress, suggesting that TCAP could be inhibiting cells from undergoing apoptosis, acting through a cell survival pathway or rescuing cells from necrosis. The Examples herein indicate that this neuroprotective effect occurs by the inhibition of mechanisms regulating necrosis and to a lesser extent by regulating apoptotic, survival, or cell cycle pathways.

Example 8—TCAP Modulates Neurite Length in Immortalized Hypothalamic N38 Cells

Figure 9:
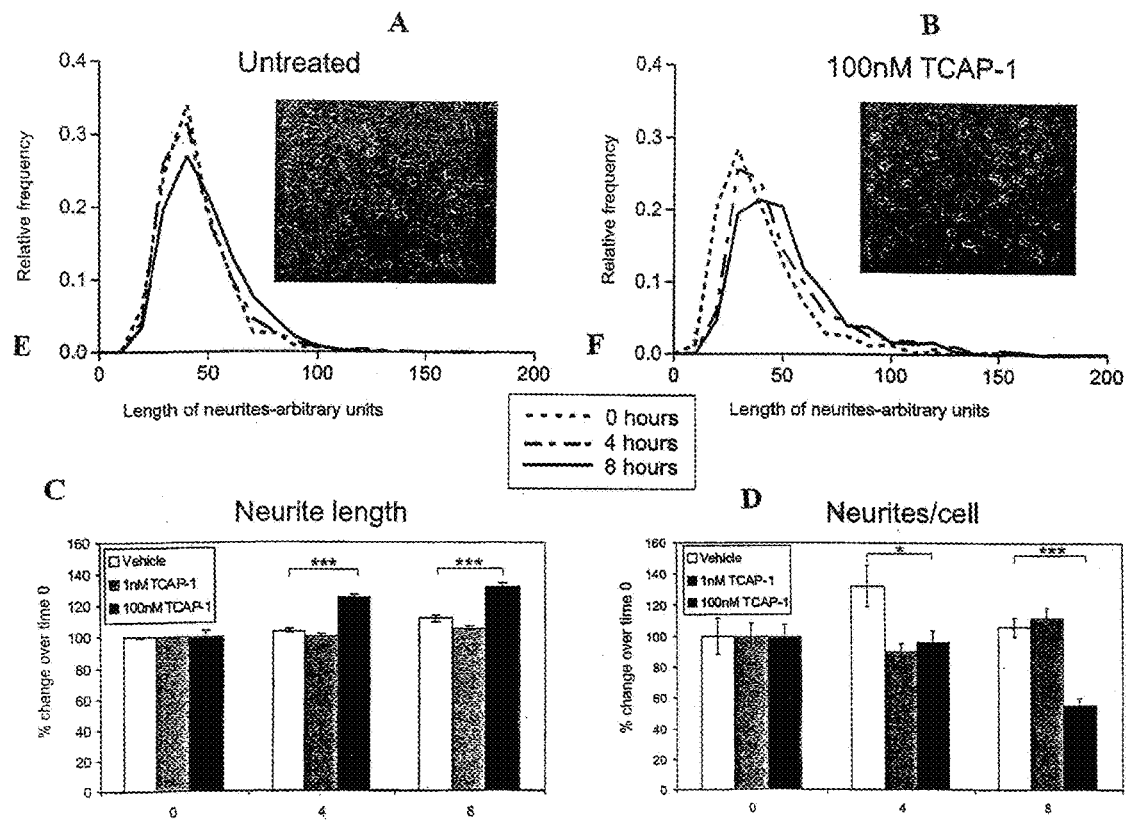
FIG. 9 illustrates immortalized mouse hypothalamic N38 cells treated with 1 nM and 100 nM mouse TCAP-1 and measurements of neurite lengths.

Immortalized mouse hypothalamic N38 cells were treated with 1 nM and 100 nM mouse TCAP-1 and measurements of neurite lengths were taken over 8 hours post TCAP administration. FIG. 9A illustrates untreated cells at 8 hours. FIG. 9B illustrates cells treated with 100 nM of TCAP-1 at 8 hours. FIG. 9C illustrates percent change in neurite length in control (untreated), 1 nM TCAP-1 and 100 nM TCAP-1 at 0, 4 and 8 hours post TCAP administration. FIG. 9D illustrates the percent change of number of neuritis in control (untreated), 1 nM TCAP-1 and 100 nM TCAP-1 at 0, 4, and 8 hours post TCAP administration. FIGS. 9E and 9F illustrate the frequency distribution in neurite length of the cell population in untreated (9E) and 100 nM TCAP-1 treated (9F) samples.

Results

The results of these experiments illustrate that TCAP is useful in enhancing neurite length. TCAP-1 induced 25% and 31% increase (p<0.001, one way ANOVA with Bonferroni's post-test, n=4) in neurite length at 100 nM, at 4 hr and 8 hr, respectively, relative to the length at the beginning of treatment. After 8 hrs, 100 nM TCAP-1 induced about a 45% (p<0.001) reduction in the number of neurites per cell. A frequency distribution of the neurite length indicated that 100 nM TCAP-1 promoted longer but fewer neurites per cell.

Example 9—TCAP Upregulates β-Tubulin and β-Actin Levels In Immortalized N38 Cells β-tubulin and β-actin expression levels in immortalized mouse N38 cells were studied.

Materials and Methods

Primary Antisera

All antisera used in this study are rabbit polyclonal antisera. β-Actin and GAPDH were purchased from Abcam (Cambridge, Mass.). α-actinin 4 antisera were purchased from Alexis Biochemicals (Lausen, Switzerland). The β-tubulin antisera was purchased from Neomarkers, Lab Vision (Fremont, Calif.) and β-tubulin III was purchased from Sigma-Aldrich Canada (Oakville, ON).

Morphological Analyses of Immortalized Neurons

N-38 immortalized mouse hypothalamic cells were cultured in quadruplet in 6 well tissue culture plates until 70% confluent at which time fresh DMEM with 10% fetal bovine serum (Invitrogen Canada, Burlington, ON) containing 1 nM TCAP-1, 100 nM TCAP-1 or vehicle (PBS) was added. Each well was digitally imaged twice at 0, 4 and 8 hours using an inverted Zeiss Axiovert 200M. A minimum of 90 cells were analyzed per condition using Labworks V4.0.0.8 (UVP, Upland, Calif.) and scored for number of neurites per cell, neurite length and cell size.

Quantitative Real Time-PCR

Total RNA from N-38 cells was isolated by the guanidinium thiocyanate phenol chloroform extraction method (Chomczynski and Sacchi, 1987). First strand cDNA was synthesized from 1 µg deoxyribonuclease I-treated RNA, using SuperScript reverse transcriptase (RT) and random primers (Invitrogen, Carlsbad, Calif.), as described in the Superscript cDNA Synthesis Kit (Invitrogen, Carlsbad, Calif.). The specificity of each amplification reaction was monitored in control reactions, where amplification was carried out on samples in which the RT was omitted (RT−). Quantitative "real time" RTPCR was performed as described in the SYBR Green PCR Master Mix and PCR Protocol (Applied Biosystems, Foster City, Calif.). Briefly, cDNA was synthesized from 1 µg total RNA in a total volume of 20 ul. 50-100 ng cDNA as template was amplified with SYBR Green Master Mix (Applied Biosystems) and 300 nM primers in a 10 µl reaction for 40 cycles (15 sec at 95 C, 1 min 60 C). The primers used for RT-PCR are: 18s rRNA; gtaacccgttgaaccccatt, ccatccaatcggtagtagcg: α-actinin 4; gagaagcagcagcgcaaga, ccgaagatgagagttgcacca: β-actin; ggccaaccgtgaaaagatga, cacagcctggatggctacgt: β-catenin; agcagtttgtggagggcgt, cgagcaaggatgtggagagc: α-tubulin 1; acaggattcgcaagctggc, ccaagaagccctggagacc: and β-tubulin 4; tgaggccacaggtggaaactatgt, aagttgtctggccgaaagatctgg. All primers were designed using Primer Express software (Applied Biosystems) and synthesized by ACGT Corp. (Toronto, ON) or Integrated DNA Technologies, Inc. (Coralville, Iowa). Data was represented as mean quantity, defined as the average of the replicate group (n>3), analyzed using ABI Prism 7000 SDS software package (Applied Biosystems). Copy number of amplified gene was standardized to 18S rRNA levels. The final fold differences in expression were relative to the vehicle treatment at each individual timepoint.

Western Blot Analysis of Cytoskeletal Proteins

N38 immortalized hypothalamic cells were cultured as described previously (Belsham et al, 2004) in Dulbecco's Modified Eagle Medium (DMEM) with 5% fetal bovine serum (Invitrogen Canada, Burlington, ON). At 70% confluency, cells were treated with medium containing 1 nM TCAP-1, 100 nM TCAP-1 or vehicle (phosphate buffered saline (PBS) pH 7.4) for 0.5, 1, 4 or 8 hours after which total cell proteins were extracted. Briefly, cells were removed in the presence of cold PBS and centrifuged. The cells were resuspended in PBS containing 1% Triton X-100 (Sigma), 1 mM dithiothreitol (DTT) and protease inhibitors ((5% Protease inhibitor cocktail set III (Calbiochem, EMD Biosciences, San Diego, Calif.) and 1 mM phenylmethyl sulfonyl fluoride (PMSF, EM Science)). Following vortex mixing, the cells were spun for 15 minutes at 15,300 g at 4° C. The supernatant containing total proteins was stored at −20 C.° until further analysis. The protein concentration was determined using a BCA protein assay kit (Pierce Chemical Co, Rockford, Ill.). For SDS PAGE, the appropriate μg loading volumes were determined for each antiserum. Samples were mixed with sample buffer containing SDS and boiled for 5 minutes at 90 C.° and were run in duplicate to test for glyceraldehyde-3-phosphate dehydrogenase (GAPDH) as a loading control. The proteins were resolved on 4-20% Tris-HCl Ready gels (Bio-Rad, Hercules, Calif.) using a Mini-PROTEAN 3 Cell (Bio-Rad) electrophoresis unit for 35 minutes at 200V. Transfers were performed using the Mini Trans-Blot Electrophoretic Transfer cell (Bio-Rad) with Hybond C Nitrocellulose membranes (GE Healthcare, Piscataway, N.J.) at 100V for 2 hours. Membranes were blocked in 0.2% PBS-Tween 20(v/v) containing 5% nonfat milk (w/v) and probed with primary antiserum overnight at 4 C.° at the appropriate dilution. The dilutions are as follows: β-actin, 1:4000; β-3-tubulin, 1:500; α-actinin-4, 1:5000. The secondary antibody conjugated to horse radish peroxidase was used at a concentration of 1:5000. For all analyses the GAPDH antiseraum was used at a dilution of 1:2000. A ECL Western Blotting Analysis System (GE Healthcare, Piscataway, N.J.) was used to detect the proteins using X OMAT Blue XB1 film. Blots were scanned and optical density was determined using an Epi Chemi II Darkroom and Lab works V4.0.0.8 (UVP, Upland, Calif.).

Gene and Protein Expression and Confocal Studies

Gene Expression

Figure 10:
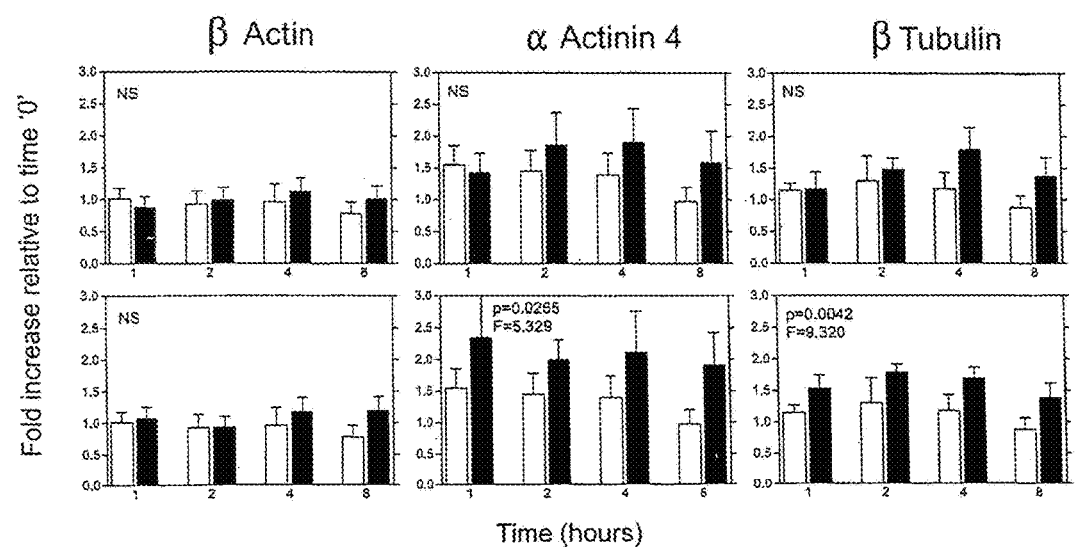
FIG. 10: Analysis of gene expression following TCAP stimulation. N-38 immortalized neurons were treated with 1 or 100 nM TCAP or vehicle over a 8 h timecourse. Total RNA was isolated at the indicated timepoints. Real-time RT-PCR was performed for β-actin; α-actinin 4; and β-tubulin. All genes were normalized to 18S rRNA levels as a loading control. Statistical significance was determined using a two way analysis of variance (n=5-8).

Significant changes in mRNA expression, as determined by real-time PCR were not observed in any of the 1 nM TCAP treatments (FIG. 10). However there were indications of expression increase in α-actinin-4 and β-tubulin mRNA after 4 hours, although these changes were not statistically significant. In contrast, at a concentration of 100 nM TCAP, there was a significant increase in synthesis as determined by a two-way analysis of variance (ANOVA) for β-catenin (p=0.0158; F=6.192), α-actinin-4 (p=0.0265; F=5.329) and β-tubulin (p=0.0042; F=9.320). Expression of mRNA for β-catenin and α-actinin-4 showed increases between 30 and 40% within 1 hr of treatment and remained high for 8 h. β-tubulin expression was more modest with a maximal increase of 25 to 30%, although inter-experimental variability as assessed by standard errors were low.

Protein Expression

Figure 11:
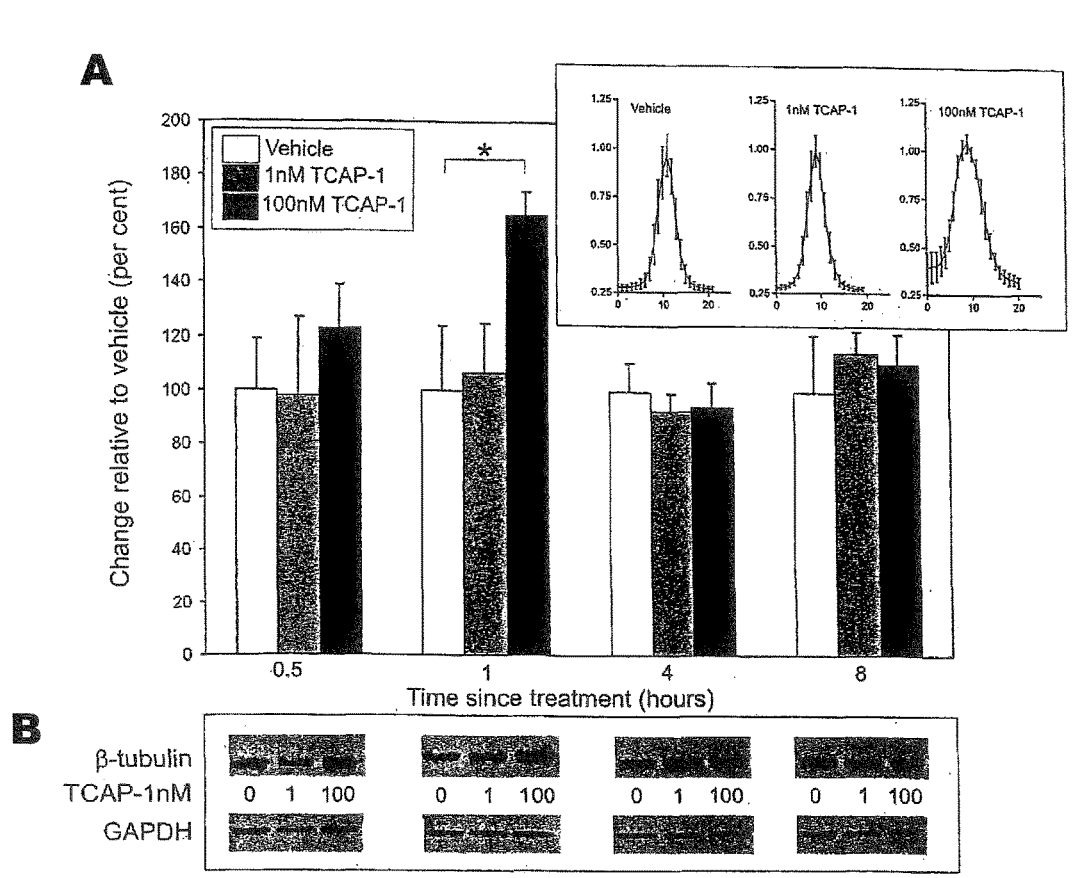
FIG. 11: β-tubulin protein expression is increased after 1 hour of 100 nM TCAP-1 treatment. A. Protein levels in N38 cells were assayed using western blotting. 100 nM TCAP-1 induced a significant increase at 1 hour (two-way ANOVA with Bonferroni's post-hoc test $p<0.05$) B. Representative blots for the different time-points C. Mean and SE of the optical density of the blots at 1 hour.
Figure 12:
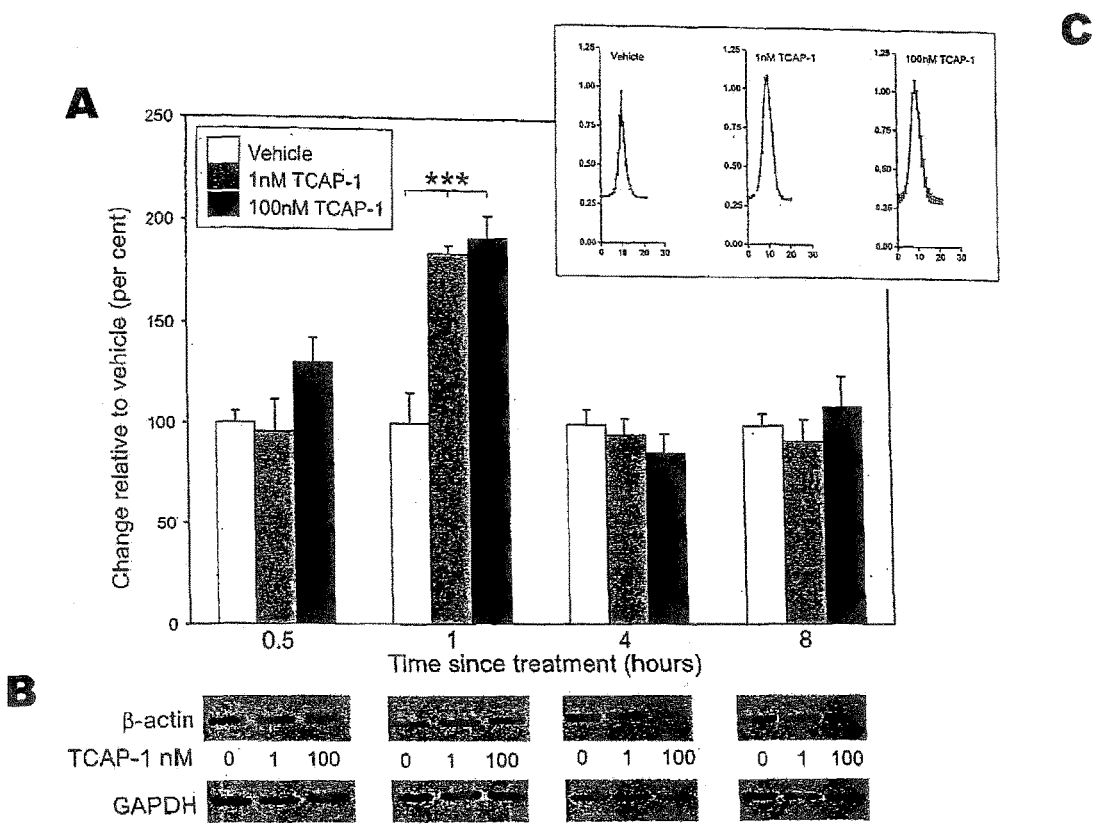
FIG. 12: Cytoskeletal β-actin protein expression is upregulated in N38 cells after 1 hour of TCAP-1 treatment. A. 1 and 100 nM TCAP-1 induces a significant increase in β-actin levels in cells treated for one hour (two way ANOVA with Bonferroni's post-hoc test $p<0.001$) B. Representative blots for the different time points C. Mean and SE of the optical density of the blots at 1 hour.
Figure 13:
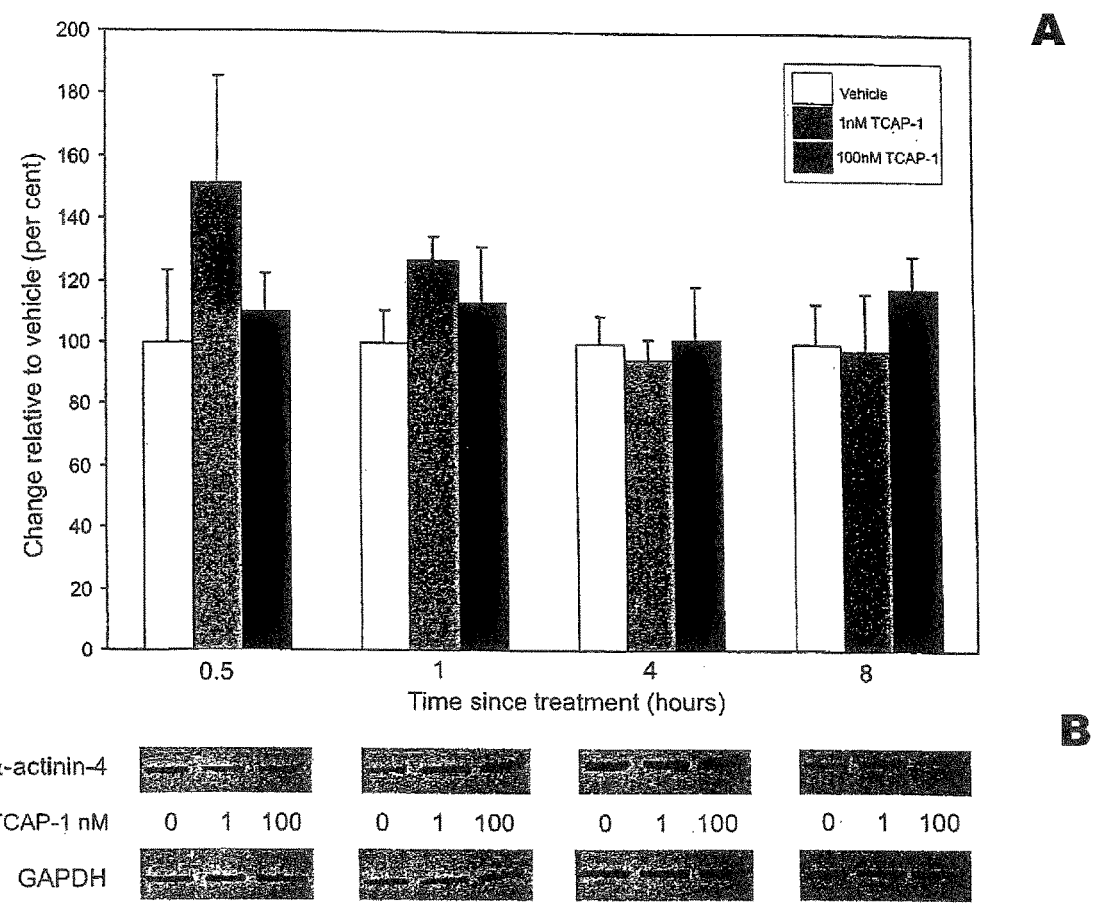
FIG. 13 Effect of TCAP-1 treatment on α-actinin-4 protein levels. A. TCAP-1 treatment did not cause any real change over 8 hours. B. Representative western blots.

Treatment of cells with 1 nM TCAP-1 did not result in any significant changes in β-tubulin protein levels over 8 hours (FIG. 11A-C). In contrast, cells treated with 100 nM showed a significant increase of 60% at 1 hour in β-tubulin relative to the vehicle treated cells at the same time point (two-way ANOVA with Bonferroni post-test, p<0.05, F=1.48). TCAP-1 treated cells also experienced a significant change with regards to β-actin expression (FIG. 12A-C). A concentration of 1 nM TCAP-1 showed an expression level of 184±4.1% of vehicle at 0.5 hrs. Similarly 100 nM TCAP-1 induced an expression level of 192±10.5%. No significant effects were noted at any other time points or on α-actinin-4 (FIG. 13A and B). Due to the consistent high levels of both β-tubulin mRNA and protein levels, βtubulin immunoreactivity was used as a marker to examine subsequent TCAP induced effects on cellular morphology.

Immunofluorescence Confocal Microscopy

In one study, a confocal analysis of 100 nM TCAP-1 effects on localization of B-tubulin in N38 cells was conducted.

Figure 14:
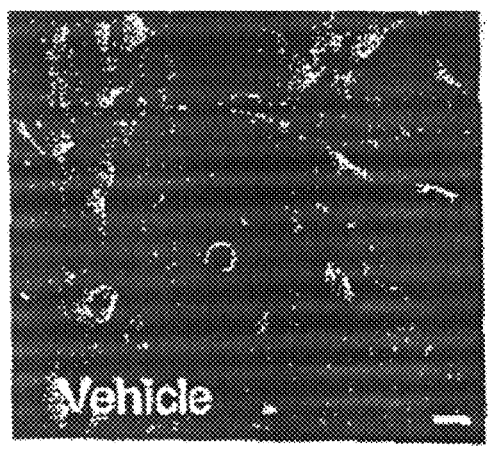
FIG. 14: Confocal immunofluorescence of beta tubulin in N38 cells Confocal analysis of 100 nM TCAP-1 effects on localization of β-tubulin in N38 cells. Immunofluorescence analysis of cells treated with 1 hour TCAP-1 show an increase in β-tubulin expression both in the perinuclear and the whole cell region. A. Ten central cells from each image was analyzed for the number of pixels at maximal intensity (149) and expressed as a ratio of total pixels in B. the perinuclear region and C. the whole cell (Student's t-test with Welch's correction for unequal variances p=0.05, minimum 30 cells per group). Perinuclear region and cell size not different in control and treated cells. Bar=20 µm.
Figure 14:
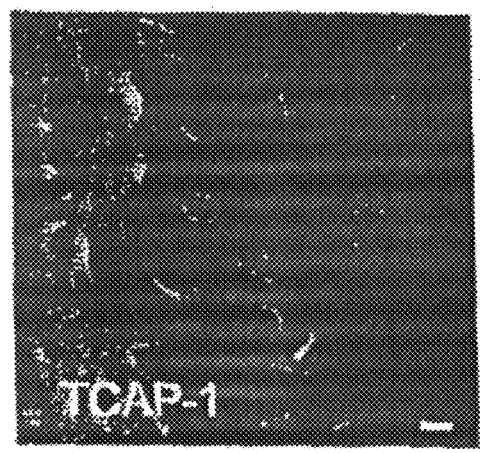
Figure 14:
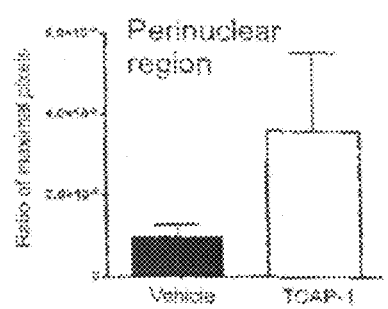
Figure 14:
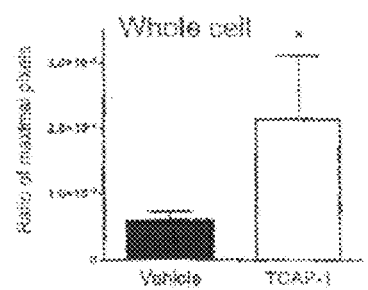

FIG. 14A show B-tubulin immunoreactivity with Alexa fluor 488 in vehicle and TCAP-1 treated cells after 1 hour post-vehicle or mouse TCAP-1 treatment, respectively. Ten central cells from each image were then analyzed for number of pixels at maximal intensity (149) and expressed as a ratio of total pixels in the perinuclear region (FIG. 14B) and the whole cell (FIG. 14C) (Student's t-test with Welch's correction for unequal variances P=0.05; bar=20 μm). Perinuclear region and cell size were not different in 30 cells per group.

Results

Overall, the TCAP-treated cells were characterized by greater clarity and number of observable β-tubulin strands in the cells and the neuritis (FIG. 14A). The 100 nM TCAP-1 treatment resulted in a significant increase in whole cell immunofluorescence (FIG. 14B).

The results indicate that cells treated with TCAP show an increased expression of B-tubulin in the cell and perinuclear region of neuronal cells and increase in B-tubulin protein levels. The results further illustrate that cytoskeletal B-actin is upregulated in TCAP-treated cells. Actin synthesis and expression is a normal and required component of neuron function, migration and axon elongation. Regulation of actin synthesis and expression is required for restoration of function following necrotic or inflammatory degenerative conditions.

Example 10—TCAP Induces Repulsion in Growing Axons

Figure 15:
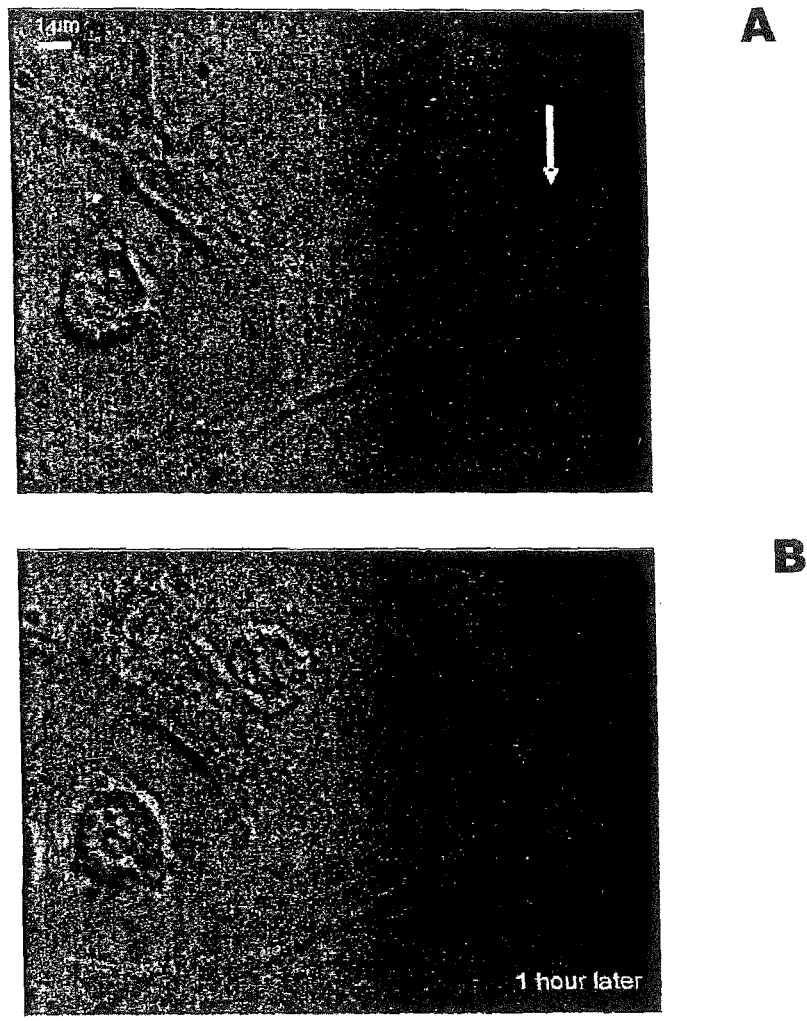
FIG. 15 illustrates that 100 nM TCAP administered to a developing axon of an N38 cell in the direction of the arrow (A) causes expansion of the growth cone area followed by repulsion away from the source of TCAP (B). Bar=1 µm.

100 μM TCAP-1 was puffed on the neurite of an N38 cell in the direction of the arrow in FIG. 15A. The neurite was imaged over one hour. TCAP caused expansion of the growth cone area followed by repulsion away from the source of TCAP (FIG. 15B). Bar—1 um.

Results

The images clearly show that TCAP induce repulsion in growing axons and can be used as a guidance molecule for neuronal growth and potentially fasciculation.

Example 11—Increases Growth and Fasciculation of Primary Embryonic Hippocampal Cultures This example illustrates the immunohistochemistry of β-tubulin III in primary hippocampal E18 cultures treated with vehicle or 100 nM TCAP-1 for seven days.

Timed-pregnant Sprague-Dawley rats (Charles River, Boston, Mass.) on day 18 (E18) of gestation were euthanized in a CO2 chamber. The uteri were surgically removed and embryos were collected in Hank's balanced salts solution (HBSS) with 15 mM HEPES and 10 mM sodium bicarbonate (Sigma-Aldrich Canada, Oakville, ON). The embryos were decapitated the hippocampi dissected. The hippocampi were trypsinized for 15 minutes at 37 C.°, centrifuged for 5 minutes at 1600 rpm and the pellets washed two times in HESS. The cell pellets were suspended in Neurobasal medium supplemented with B27, 0.5 mM Glutamax, and penicillin/streptomycin and this medium was subsequently used for culturing. Following trituration with a fire polished glass pipette, 300 000 cells were plated into 6-well plates containing 12 mm glass coverslips coated with poly-D-lysine (VWR, Mississauga, ON). After 24 hours, fresh medium containing 100 nM TCAP or vehicle was used. The medium was replaced twice a week. On the eighth day of culture, coverslips were processed.

The coverslips with cells were rinsed with PBS (pH 7.4) twice before fixing with 1 ml 4% paraformaldehyde for 15 minutes. Following two washes for 5 minutes, cells were permeabilized by addition with 0.2% Triton X100 solution in PBS for 90 seconds. After washing twice for 2 minutes, the cells were incubated with 0.5% normal goat serum (NGS) in PBS. A 1:100 dilution of β-tubulin III antiserum in 0.5% NGS was applied to the coverslips and incubated at room temperature for 1 hour. The detection and staining was done according to instructions provided by the Vectastain ABC kit (Vector Laboratories, Burlington, ON, Canada). The biotinylated goat anti-rabbit serum was applied at 1:200 dilution in serum for 1 hour as well. The Vectastain reagents, avidin DH and biotinylated horse radish peroxidase H were mixed and incubated with the cells for 30 minutes before washing for 5 minutes with PBS. The DAB substrate (Vector Laboratories) was then added for 8 minutes and cells washed with distilled water for 5 minutes. The cells were dehydrated with ethanol, cleared with Xylene and the coverslip mounted on a slide using Vectamount mounting medium (Vector Laboratories). The stained cells were visualized using an Olympus (BX60) microscope and imaged with a CCD CoolSNAP camera (Photometrics, Tuscon, Ariz.).

Results

Figure 16:
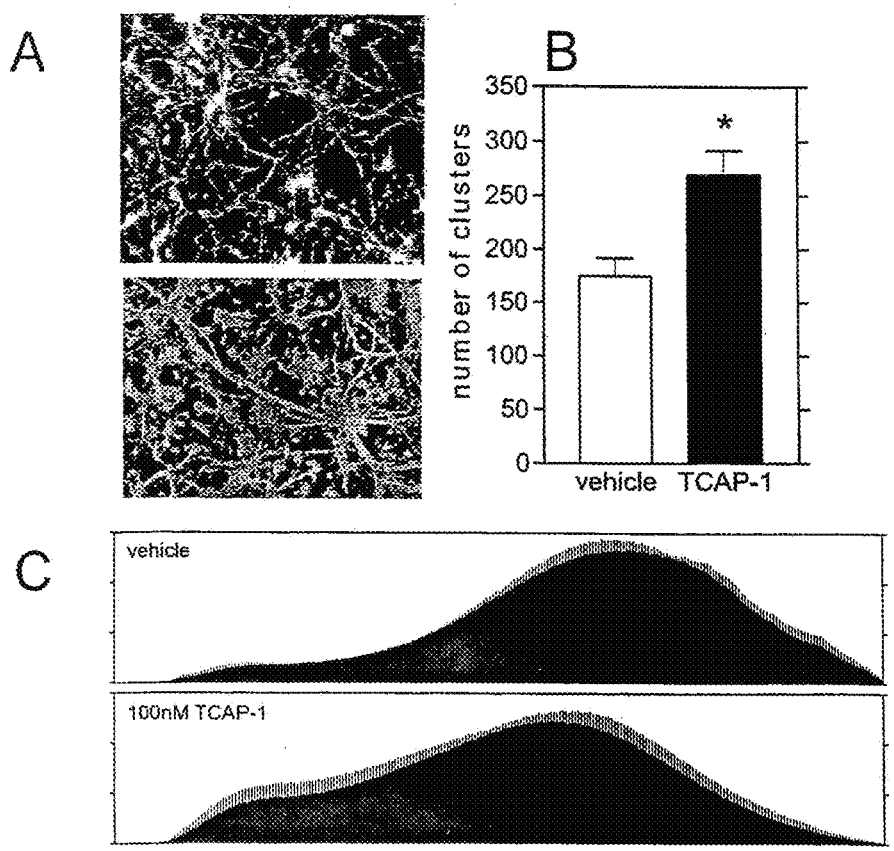
FIG. 16. Effect of TCAP-1 on primary cultures of hippocampal cells. A. Reverse image of hippocampal cultures. Top panel, vehicle treated cells, bottom panel TCAP treated cells. B. There were significantly ($p<0.01$) greater number of cells and cell clusters in the TCAP-1 treated cultures (n=4, two way students t test). C. Histograms of mean pixel intensity (n=4). Standard error of the mean is indicated.
Figure 17:
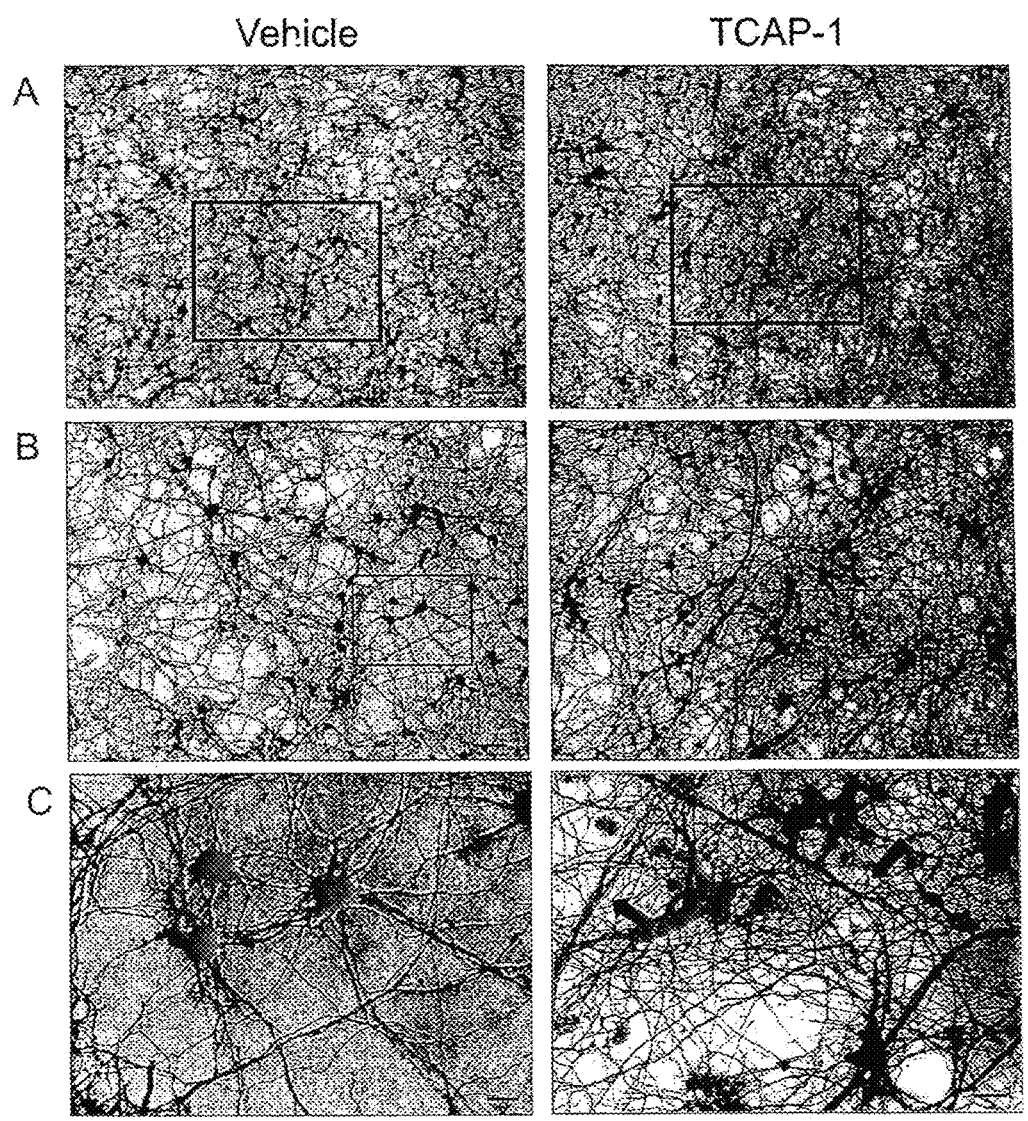
FIG. 17: TCAP-1 in culture medium caused an increase in dendritic density and fasciculation in primary E18 hippocampal cultures. Anti-β-tubulin III immunocytochemistry cultured in the presence of vehicle or 100 nM TCAP-1 for seven days. Boxes indicate regions shown in the subsequent image. A. ×40 magnification, bar=0.25 mm B. ×100 magnification, bar=100 µm C. ×4000 magnification, arrows point to areas of fasciculation, bar=25 µm.

The results shown in FIGS. 16 and 17 clearly show that TCAP caused an increase in dendritic density and fasciculation compared to control.

The β-tubulin-III immunoreactivity in primary hippocampal cultures treated with 100 nM TCAP-1 was enhanced (FIG. 16A-C). A frequency distribution of pixel intensity indicated a significant ($p<0.05$) effect of TCAP-1 using a Chi square test for trends (FIG. 16C. The increase in immunoreactivity was due to both an increase in total number of cells and cell processes as indicated by the increase in the number of pixels in the dark gray to black regions (FIG. 16A). TCAP-1 treated cultures show a significantly greater ($p=0.0142$) mean number of cell clusters (270±22) over the vehicle treated cells (175±17) as determined by a two-tailed Students t-test (FIG. 16B). A much denser mesh of cell processes were observed in TCAP treated cells.

TCAP treated hippocampal cells showed a much greater incidence in the number of large axons and axon bundles relative to the vehicle treated cells. Higher magnification of both groups of cultures revealed that the TCAP treated cells showed a much greater tendency for fasciculation along with a greater incidence of neural processes outgrowth (FIG. 17).

The results further illustrate that TCAP can be used to increase fasciculation among neurons and in addition to supporting the effects of TCAP on inhibiting neuronal cell death, it illustrates that TCAP may be used in the treatment of a number of conditions, such as brain injury, especially if administered with 8 or 24 hours of said injury to minimize any secondary injury effects.

TCAP 1 is a novel putative neuropeptide that bears the structural hallmarks of a bioactive peptide. TCAP-1 can modulate cell growth and anxiety-related behaviors. The present study shows that TCAP-1 has the ability to stimulate neurite outgrowth in part by increasing the synthesis of components of the cytoskeleton. The TCAP-1 mediated neurite outgrowth is coupled with an increase in the synthesis and translation off β-tubulin and possibly the enhanced translation of β-actin. In primary hippocampal cultures, the increase in β-tubulin expression is associated with an increase in the number of immunoreactive β-tubulin cells and large axonal processes. Because many long term behavioural effects are associated with changes in neuronal circuitry, the effects observed with TCAP can be explained by changes in the morphological properties of neurons.

The morphological characteristics of cells treated with TCAP were examined. An immortalized hypothalamic cell line (N38) previously known to be responsive to TCAP-1 (Belsham et al, 2004; Wang et al, 2005) was used in the Examples. Cell cultures were held at 70-80% confluency as a maximal as beyond that, the cells went into a stress response. TCAP-1 treated cells showed a dose-dependent increase in the number of longer neurites and a decrease in the number of shorter neurites.

Together, the present studies with the N38 cell line indicate that TCAP 1 stimulates neurite outgrowth and increases the synthesis and translation of β-tubulin while enhancing β-actin translation only. TCAP induced an increase in the incidence of axon formation and fasciculation. In one embodiment, TCAP and the teneurins can be used to regulate neuronal process outgrowth in the hippocampus and in the potentiation of learning and memory.

In one embodiment, the Examples indicate that TCAP may exert its effects at least in part by inducing changes in axonal and dendritic outgrowth. Changes in dendritic morphology are important since they are the mechanism behind many diseases and disorders. Specifically, the hippocampus is a neuroplastic part of the brain whose cells when exposed to effectors can undergo morphological changes associated with disorders such as stress and depression (McEwen, 1999). The present Examples also indicate that the TCAP and teneurin system is associated with neuroplasticity, learning and anxiety.

Example 12—Superoxide Dismutase-Catalase Data

Superoxide Dismutase Detection and Measurement

Figure 18:
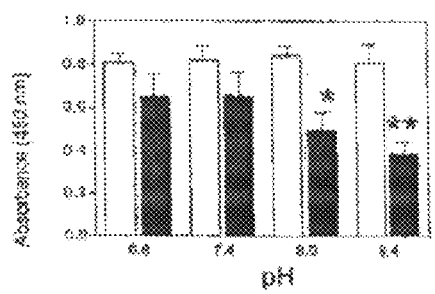
Figure 18:
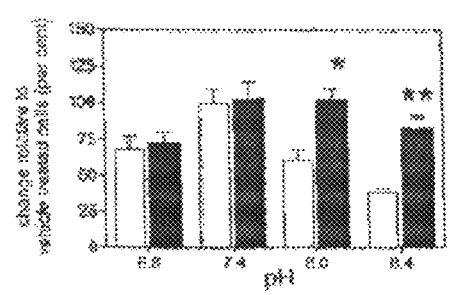
Figure 18:
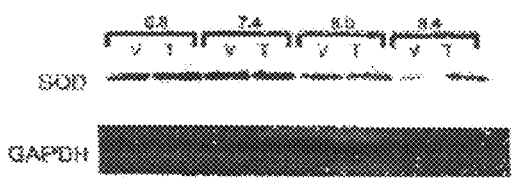
Figure 18:
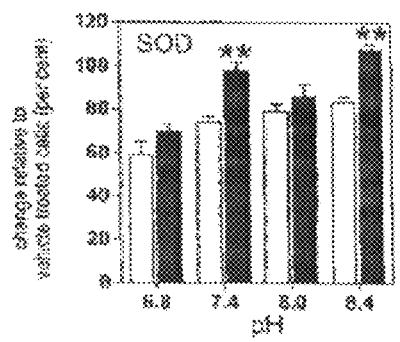
Figure 18:
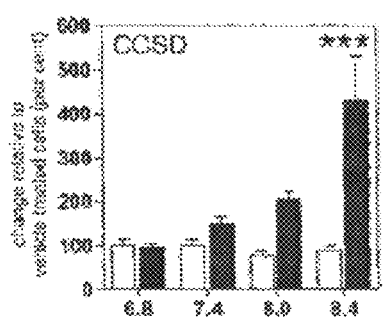

Examination of the superoxide dismutase-associated system was investigated as a possible mechanism for necrosis after the apoptotic, survival and cell cycle experiments did not show a robust effect. The presence of the superoxide radical was measured indirectly by the conversion of a soluble tetrazolium salt in cells after 48 hours (FIG. 18A). The TCAP-1 treated cells showed a 40% ($p<0.05$) and 60% ($p<0.01$) decrease in the absorbance of the substrate, which is proportional to superoxide radical activity, at pHs 8.0 and 8.4, respectively. However, because this method shows only the indirect presence of the superoxide radical, and by inference, the presence of superoxide dismutase, we also examined the presence of this enzyme protein directly by western blot (FIG. 18B,C). Relative to the vehicle-treated cells at pH 7.4, superoxide dismutase levels in the vehicle-treated cells showed a significant ($p<0.05$) decrease as a function of pH, as determined by a one-way ANOVA. There were no significant differences in the expression of the superoxide dismutase protein at pHs 6.8 and 7.4. In contrast, at pH 8.0 and 8.4, TCAP-1 significantly ($p<0.05$ and $p<0.01$, respectively) reduced the pH-induced decline in superoxide dismutase levels. The superoxide dismutase expression levels at pH 8.0 and 8.4 were not significantly different than that of the vehicle-treated cells at pH 7.4.

Superoxide dismustase gene expression as measured by real-time PCR indicated a significant ($p<0.01$) increase over the vehicle treated cells at pH 7.4 and 8.4 (FIG. 18D). A greater effect on gene expression was noted in superoxide copper chaperone (CCSD) expression where CCSD expression levels in the TCAP-1 treated cells at pH 8.4 was increased almost 4.5 fold over the vehicle treated cells (FIG. 18E).

$H_2O_2$ Toxicity and Catalase Activity

Figure 19A:
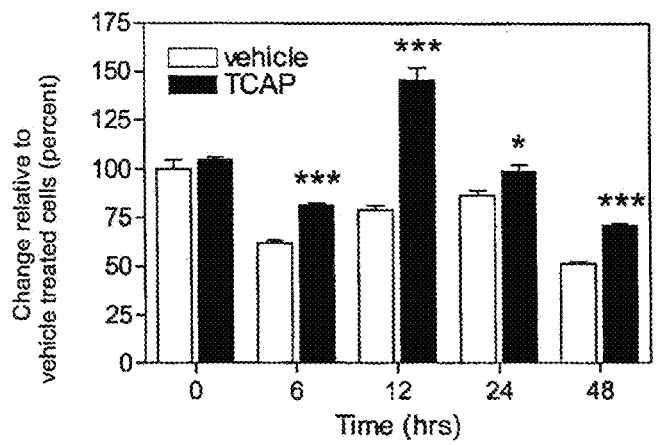
FIG. 19A illustrates that TCAP-1 showed a significant increase in MIT activity relative to the vehicle-treated at 6-48 hours in cells treated with 50 uM H2O2.

TCAP-1 showed a significant increase in MTT activity relative to the vehicle-treated at 6 to 48 hours in cells treated with 50 µM H2O 2 (FIG. 19A). The results indicate that TCAP-1 significantly increased mitochondrial activity at 6, 12 and 48 hours ($p<0.001$) ($F=168.2$) as compared with the vehicle-treated cells. There was also a less significant effect at 24 hours ($p<0.05$) and no effect at 0 hours.

Figure 19B:
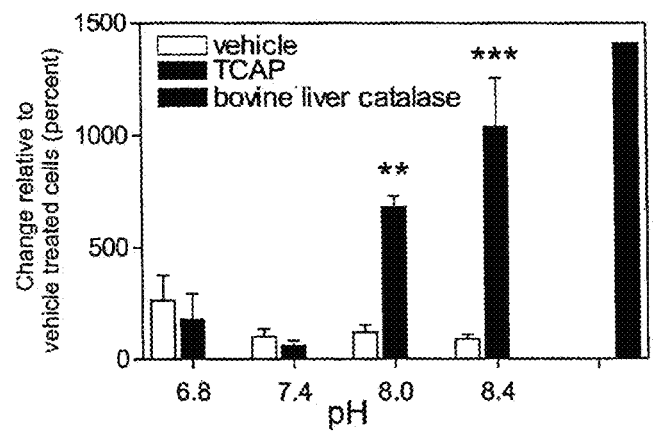
FIG. 19B illustrates the results of a catalase assay on pH treated cells.
Figure 19C:
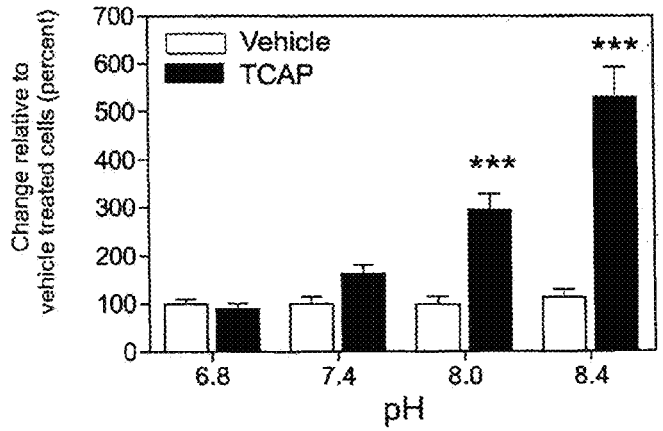
FIG. 19C illustrates catalase gene expression as determined by real-tie PCR.

A catalase assay was performed on the pH treated cells in order to determine whether TCAP-1 was conferring survivability to the cells via upregulation of catalase and thus increasing H2O 2 breakdown into H2O and O2 (FIG. 19B). The results indicate that TCAP-1 significantly increased catalase levels at pH 8.4 ($p<0.001$) ($F=24.42$) as compared to the vehicle treated cells according to a two-way ANOVA with a Bonferroni's post hoc test. There was also a significant TCAP-1 effect at pH 8.0 ($p<0.01$) but no significant effects at either pH 6.8 or pH 7.4 compared to the vehicle treated cells. Bovine liver was also assayed as a positive control. Catalase gene expression, as determined by real-time PCR indicated that TCAP induced mRNA levels by 3 fold ($p<0.001$) and 5 fold ($p<0.001$) at pHs 8.0 and 8.4, respectively (FIG. 19C).

Superoxide dismutase is an enzyme that is responsible for catalyzing the highly reactive oxygen radical, superoxide (O2-) into hydrogen peroxide (H2O2). Hydrogen peroxide is in turn, catalysed to water by the enzyme catalase. Superoxide dismutase is bound to copper atoms for full activity. The protein superoxide dismutase copper chaperone acts to effect the transfer of copper to superoxide dismutase. Together, these three proteins act to protect the cells from the toxic effects of reactive oxygen species (ROS). High concentrations of ROS have been implicated in the destruction of cellular membranes and proteins and play a significant role in the onset of neurodegenerative disorders. The findings that TCAP enhances the activity and expression of the superoxide dismutase-catalase system is indicative that TCAP inhibits cellular necrosis.

While the foregoing invention has been described in some detail for purposes of clarity and understanding, it will be appreciated by one skilled in the art, from a reading of the disclosure, that various changes in form and detail can be made without departing from the true scope of the invention in the appended claims.

All publications, patents, and patent applications are herein incorporated by reference in their entirety to the same extent as if each individual publication, patent or patent application was specifically and individually indicated to be incorporated by reference in its entirety.

REFERENCES

1. Akbar M, Calderon F, Wen Z, Kim H Y. Docosahexaenoic acid: A positive modulator of Akt signaling in neuronal survival. Proc Natl Acad Sci USA. 2005 Jul. 22; [Epub ahead of print]
2. Arends, M. and Willie A H. Apoptosis: mechanisms and role in pathology. Int Rev. Exp. Pathol. 32(1991):223-254.
3. Baumgartner, S., Martin, D., Hagios, C. & R. Chiquet-Ehrismann, Tenm, a *Drosophila* gene related to tenascin, is a new pair rule gene. EMBO J. 13 (1994) 3728-3740.
4. Belsham, D., Cai, F., Cui, H., Smukler, S., Salapatek, A., Shkreta, L. Generation of a Phenotypic Array of Hypothalamic Neuronal Cell Models to Study Complex Neuroendocrine Disorders. Endocrinology 145 (2004): 393-400.
5. Brenneman, D., J. M. Hill, G. W. Glazner, I. Gozes and T. W. Phillips. Interleukin-1 alpha and vasoactive intestinal peptide: enigmatic regulation of neuronal survival. Int. J. Dev. Neurosci. 13(1995):187-210.
6. Buja, L M., Eigenbrodt M L and Eigenbrodt E H. Apoptosis and necrosis: basic types and mechanisms of cell death. Arch. Pathol. Lab. Med. 117(1993):1208-1214.
7. Casiano C, Ochs R, Tan, E Distinct cleavage products of nuclear proteins in apoptosis and necrosis revealed by autoantibody probes. Cell Death and Differentiation. 5(1998): 183-190.
8. Columbano A. Cell death: current difficulties in discriminating apoptosis from necrosis in the context of pathological processes in vivo. J. Cell. Biochem. 58(1995):181-190.
9. Chomczynski P, Sacchi N (1987) Single-step method of RNA isolation by acid guanidinium thiocyanate-phenol-chloroform extraction. Analytical Biochem 162:156-159.
10. Crowder R J, Freeman R S. Phosphatidylinositol 3-kinase and Akt protein kinase are necessary and sufficient for the survival of nerve growth factor-dependent sympathetic neurons. J Neurosci 18(1998): 2931-2943.
11. Dudek H, Datta, S., Franke, T., Birnbaum, M., Yao R, Cooper, G., Segal, R., Kaplan, D., Greenberg, M. Regulation of neuronal survival by the serine-threonine protein kinase Akt. Science. 275(1997): 661-5
12. Emery E., Aldanap, P., Bunge, M B. Apoptosis after traumatic human spinal cord injury. J. Neurosurg 89(1998)911-20.
13. Gennari, J. Goldstein, M & W. Schwartz, The nature of the renal adaptation to chronic hypocapnia. J Clin Invest. 1972 July; 51(7): 1722-1730.
14. Giffard R G, Weiss J H, Choi D W. Extracellular alkalinity exacerbates injury of cultured cortical neurons. Stroke. 23(1992): 1817-1821.

15. Glazer, R., and I. Gozes. Diurnal oscillation in vasoactive intestinal peptide gene expression independent of environmental light entraining. Brain Res. 644(1994): 164-168.
16. Gozes, I. and D. E. Brenneman. Activity-dependent neurotrophic factor (ADNF): An extracellular neuroprotective chaperonin? J. Molec. Neurosci. 7(1996):235-244.
17. Gratzner, H. G. Monoclonal antibody to 5-bromo- and 5-iododeoxyuridine: A new reagent for detection of DNA replication. Science 218(1982):474-5.
18. Hengartner M O. The biochemistry of apoptosis. Nature. (2000); 407(6805):770-6.
19. Kaufmann, S H. Induction of endonucleolytic DNA cleavage in human acute myelogenous leukemia cells by etoposide, camptothecin and other cytotoxic anticancer drugs: a cautionary note. Cancer Res. 49(1989):5870-5878.
20. Kaufmann, S H., Desnoyers, S., Ottaviano, Y., Davidson N E and Poirier, G G. Specific proteolytic cleavage of poly(ADP-ribose) polymerase: an early marker of chemotherapy-induced apoptosis. Cancer Res. 53(1993): 3976-3985.
21. Khaled, A., Bulavin, D., Kittipatarin, C., Li, W., Alvarez, M., Kim, K., Young, H., Formace, A., Durum, S. Cytokine-driven cell cycling is mediated through Cdc25A. J Cell Biol 169(1999): 755-763.
22. Levine, A., Bashan-Ahrend, O., Budai-Hadrian, D., Gartenberg, S., Menasherow, R., Wides, R. Odd Oz: a novel *Drosophila* pair rule gene. Cell. (1994): 587-598.
23. Levine, R., Helpern, J., Welch, A., Vande Linde, A., Sawaya, K., Brown, E., Ramadan, N., Deveshwar, R., Ordidge, R. Human focal cerebral ischemia: evaluation of brain pH and energy metabolism with P-31 NMR spectroscopy. Radiology 185. (1992): 537-544.
24. Linnik, M D., Zobrist R H., Hatfield M D. Evidence supporting a role for programmed cell death in focal cerebral ischemia in rats. Stroke 24(1993)2002-2009.
25. Liu, X., Zhou, H., Slaughter, C., Wang X. DEF, a heterodimeric protein that functions downstream of caspase-3 to trigger DNA fragmentation during apoptosis. Cell 89(1997):175-84.
26. Mabe H, Blomqvist P, Siesjo B K. Intracellular pH in the brain following transient ischaemia. J Cereb Blood Flow Metab. 3(1993): 109-114.
27. Majno G and Jorris L. Apoptosis, oncosis and necrosis: an overview of cell death. Amer J. Pathol. 146(1995):3-15.
28. Minet, A. and Chiquet-Ehrismann, R. Phylogenetic analysis of teneurin genes and comparison to the rearrangement hot spot elements of *E. Coli*. Gene. 257(2000): 87-89.
29. Minet, A., Rubin, B., Tucker, R., Baumgartner, S., Chiquet-Ehrismann, R. Teneurin-1, a vertebrate homologue of the *Drosophila* pair-rule gene Ten-m, is a neuronal protein with a novel type of heparin-binding domain. Journal of Cell Science 112 (1999): 2019-2032.
30. Moon R B, Richards J H. Determination of intracellular pH by 31P MR. J Biol Chem 1973; 248: 7276-7278.
31. Oohashi, T., Zhou, K., Feng, B., Richter, M., Morgelin, M., Perez, W., Su, R., Chiquet-Ehrismann, R., Rauch, U., Fassler, R. Mouse ten-m/Odz is a new family of dimeric type II transmembrane proteins expressed in many tissues. J. Cell Biol. 145(1999):563-577.
32. Ostermann M E, Girgis-Hanna Y, Nelson S R, Eastwood J B, Metabolic alkalosis in patients with renal failure. Nephrol Dial Transplant. 18(2003):2442-8.
33. Pawloski, J., Kraft, A. Bax induced apoptotic cell death. PNAS. 97(2000):529-531.
34. Potapenko E, Kostyuk E, Voitenko N, Kostyuk P. Alkalinization-induced changes in intracellular calcium in rat spinal cord neurons. Neurochem Res. 2004 September; 29(9):1659-65.
35. Priest, J. M, Fischbeck, K. H., Nouri, N & B. J., Keats, A locus for axonal motorsensory neuropathy with deafness and mental retardation maps to Xq24-q26. Genomics 29 (1995) 409-412.
36. Qian X, Barsyte-Lovejoy D, Wang L, Chewpoy B, Gautam N, Al Chawaf A, D. A Lovejoy, Cloning and characterization of teneurin C-terminus associated peptide TCAP)-3 from the hypothalamus of an adult rainbow trout (*Oncorhynchus mykiss*). Gen Comp Endocrinol. 137(2004):205-16.
37. Raza, A., Ukar, K., Preisler, H D. Double labeling and in vitro versus in vivo incorporation of bromodeoxyuridine in patients with acute nonlymphocytic leukemia. Cytometry 6(1985):633-40.
38. Rello, S., Stockert, J., Moreno, V., Gamez, A., Pacheco, M., Juarranz, A., Canete, M., Villanueva, A. Morphological criteria to distinguish cell death induced by apoptotic and necrotic treatments. Apoptosis. 10(2005):201-208.
39. Robertson N J, Cowan F M, Cox I J, Edwards A D Brain alkaline intracellular pH after neonatal encephalopathy. Ann. Neurol. 52(2002):732-742.
40. Rosser B G and Gores G J. Liver cell necrosis: cellular mechanisms and clinical implications. Gastroenterology. 108(1995):252-275.
41. Rubin, B., Tucker, P., Martin, D., Chiquet-Ehrismann, R. Teneurins: a novel family of neuronal cell surface proteins in vertebrates, homologous to the *Drosophila* pair-rule gene product, Ten-m. Dev Biol. 216 (1999): 195-209.
42. Sapolsky, R. M. (1992) Stress, the aging brain and the mechanisms of neuronal death. MIT Press. Cambridge Mass. 428 pages.
43. Stout, A., Raphael, H., Kanterewicz, B., Klann, E., Reynolds, I. Glutamate-induced neuron death requires mitochondrial calcium uptake. Nature Neuroscience. 1 (1998): 366-373.
44. Thornton J S, Ordidge R J, Penrice J, Cady E B, Amess P N, Punwani S, Clemence M, Wyatt J S, Temporal and anatomical variations of brain water apparent diffusion coefficient in perinatal cerebral hypoxic-ischemic injury: relationships to cerebral energy metabolism. Magn Reson. Med. 39 (1998):920-927.
45. Thompson, C B. Apoptosis in the pathogenesis and treatment of disease. Science 267(1995):1465-1462.
46. Traynelis S, Cull-Candy S. Proton inhibition of NMDA receptors in cerebellar neurons. Nature. 356(1990): 347-349.
47. Vornov J J, Thomas A G, Jo D. Protective effects of extracellular acidosis and blockade of sodium/hydrogen ion exchange during recovery from metabolic inhibition in neuronal tissue culture. J Neurochem. 67(1996): 2379-2389.
48. Wang, L. S. Rotzinger, A. AiChawaf, R. B. Chewpoy D. Barsyte-Lovejoy, X. Qian, C. F. Elias, N. C. Wang, J. C. Bittencourt, A. De Cristefaro, D. Belsham, F. Vaccarino, D. A. Lovejoy, Teneurin proteins possess a carboxy terminal (CRF)-like sequence that modulates emotionality and neuronal growth, Submitted to Molecular Brain Research (2004).
49. Watson, A J M. Necrosis and apoptosis in the gastrointestinal tract. Gut 37(1995):165-167.

50. Willie, A H. Glucocorticoid-induced thymocyte apoptosis is associated with endogenous endonuclease activation. Nature 284(1980):555-6.
51. Willie, A.H., Kerr, J F R and Currie A C. Cell death: the significance of apoptosis. Int. Rev. Cytol. 68 (1980):251-305.
52. Xu L, Glassford A J M, Giaccia A J, Giffard R G. Acidosis reduces neuronal apoptosis. Neuroreport. 9(1998): 875-879.
53. Zhang Y, Pardridge W M. Conjugation of brain-derived neurotrophic factor to a blood-brain barrier drug targeting system enables neuroprotection in regional brain ischemia following intravenous injection of the neurotrophin. Brain Res 889(2001): 49-56.
54. Zhou X H, Brandau O, Feng K, Oohashi T, Ninomiya Y, Rauch U, Fassler R (2003) The murine Ten-m/Odz genes show distinct by overlapping expression patterns during development and in adult brain. Gene Expression Patterns 3:397-405. 21

What is claimed is:

1. A method of inhibiting neuronal necrosis and inducing neurite growth in vitro comprising administering to neuronal cells an effective amount of a teneurin c-terminal associated peptide (TCAP peptide), or a pharmaceutically acceptable salt thereof, wherein the amino acid sequence of said TCAP peptide consists essentially of:
   (i) an amino acid sequence having at least 95% identity to an amino acid sequence selected from the group consisting of SEQ ID NOs: 37, 38, 69, 70, and 101; or optionally wherein:
   (a) the carboxy terminal end of said TCAP peptide is amidated or comprises an amidation signal sequence; or
   (b) when the amino terminal amino acid of said TCAP peptide is glutamine, it is in the form of pyroglutamic acid.

2. The method of claim 1, wherein the neuronal cells sustained a physiological trauma.

3. A method of claim 1 for increasing fasciculation in neuronal cells.

4. The method of claim 1 wherein the amino acid sequence of said TCAP peptide or pharmaceutically acceptable salt thereof consists essentially of an amino acid sequence having at least 95% sequence identity to an amino acid sequence selected from the group consisting of SEQ ID NOs: 69 and 70, optionally wherein:
   (a) the carboxy terminal end of said TCAP peptide is amidated or comprises an amidation signal sequence; or
   (b) when the amino terminal amino acid of said TCAP peptide is glutamine, it is in the form of pyroglutamic acid.

5. The method of claim 4 wherein the amino acid sequence of said TCAP peptide or pharmaceutically acceptable salt thereof consists essentially of an amino acid sequence having at least 95% sequence Identity to an amino acid sequence selected from the group consisting of SEQ ID NOs: 70, optionally wherein:
   (a) the carboxy terminal end of said TCAP peptide is amidated or comprises an amidation signal sequence; or
   (b) when the amino terminal amino acid of said TCAP peptide is glutamine, it is in the form of pyroglutamic acid.

6. The method of claim 1 wherein the amino acid sequence of said TCAP peptide or pharmaceutically acceptable salt thereof consists essentially of an amino acid sequence having at least 95% sequence Identity to an amino acid sequence selected from the group consisting of SEQ ID NO: 37, 38 and 101 optionally wherein:
   (a) the carboxy terminal end of said TCAP peptide is amidated or comprises an amidation signal sequence; or
   (b) when the amino terminal amino acid of said TCAP peptide is glutamine, it Is in the form of pyroglutamic acid.

7. The method of claim 1 wherein the amino acid sequence of said TCAP peptide or pharmaceutically acceptable salt thereof consists essentially of an amino acid sequence having at least 95% sequence identity to an amino acid sequence of SEQ ID NO: 38, optionally wherein:
   (a) the carboxy terminal end of said TCAP peptide is amidated or comprises an amidation signal sequence; or
   (b) when the amino terminal amino acid of said TCAP peptide is glutamine, it is in the form of pyroglutamic acid.

8. A method for increasing β-tubulin and/or β-actin levels in neuronal cells in vitro comprising administering to the cells an effective amount of a teneurin c-terminal associated peptide (TCAP peptide), or a pharmaceutically acceptable salt thereof, wherein the amino acid sequence of said TCAP peptide consists essentially of:
- (i) an amino acid sequence having at least 95% identity to an amino acid sequence selected from the group consisting of SEQ ID NOs: 37, 38, 69, 70, and 101; or optionally wherein:
  - (a) the carboxy terminal end of said TCAP peptide is amidated or comprises an amidation signal sequence; or
  - (b) when the amino terminal amino acid of said TCAP peptide is glutamine, it is in the form of pyroglutamic acid.

9. The method of claim 8 wherein the amino acid sequence of said TCAP peptide or pharmaceutically acceptable salt thereof consists essentially of an amino acid sequence having at least 95% sequence identity to an amino acid sequence selected from the group consisting of SEQ ID NOs: 69, and 70, optionally wherein:
- (a) the carboxy terminal end of said TCAP peptide is amidated or comprises an amidation signal sequence; or
- (b) when the amino terminal amino acid of said TCAP peptide is glutamine, it is in the form of pyroglutamic acid.

10. The method of claim 9 wherein the amino acid sequence of said TCAP peptide or pharmaceutically acceptable salt thereof consists essentially of an amino acid sequence having at least 95% sequence identity to an amino acid sequence selected from the group consisting of SEQ ID NOs: 70, optionally wherein:
- (a) the carboxy terminal end of said TCAP peptide Is amidated or comprises an amidation signal sequence; or
- (b) when the amino terminal amino acid of said TCAP peptide is glutamine, it is in the form of pyroglutamic acid.

11. The method of claim 9 wherein the amino acid sequence of said TCAP peptide or pharmaceutically acceptable salt thereof consists essentially of an amino acid sequence having at least 95% sequence identity to an amino acid sequence selected from the group consisting of SEQ ID NO: 37, 38 and 101 optionally wherein:
- (a) the carboxy terminal end of said TCAP peptide is amidated or comprises an amidation signal sequence; or
- (b) when the amino terminal amino acid of said TCAP peptide is glutamine, it is in the form of pyroglutamic acid.

12. The method of claim 9 wherein the amino acid sequence of said TCAP peptide or pharmaceutically acceptable salt thereof consists essentially of an amino acid sequence having at least 95% sequence identity to an amino acid sequence of SEQ ID NO: 38, optionally wherein:
- (a) the carboxy terminal end of said TCAP peptide is amidated or comprises an amidation signal sequence; or
- (b) when the amino terminal amino acid of said TCAP peptide is glutamine, it is in the form of pyroglutamic acid.

13. A method of inhibiting neuronal necrosis and inducing neurite growth comprising administering to neuronal cells in vitro an effective amount of a teneurin c-terminal associated peptide-1 (TCAP-1 peptide), or a pharmaceutically acceptable salt thereof, wherein the amino acid sequence of said TCAP-1 peptide consists essentially of: SEQ ID NO: 70 or 38 or peptides having substitutions thereof at the first and fifth amino acid positions of the peptide, optionally wherein:
- (a) the carboxy terminal end of said TCAP peptide is amidated or comprises an amidation signal sequence; or
- (b) when the amino terminal amino acid of said TCAP peptide is glutamine, it is in the form of pyroglutamic acid.

* * * * *